(12) United States Patent
Hung et al.

(10) Patent No.: US 11,452,775 B2
(45) Date of Patent: Sep. 27, 2022

(54) DETECTION OF ARGININE METHYLATION OF EGFR FOR PREDICTION OF RESISTANCE TO THERAPY

(71) Applicant: Board of Regents, The University of Texas System, Austin, TX (US)

(72) Inventors: Mien-Chie Hung, Houston, TX (US); Hsin-Wei Liao, Houston, TX (US); Jung-Mao Hsu, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 469 days.

(21) Appl. No.: 16/703,841

(22) Filed: Dec. 4, 2019

(65) Prior Publication Data

US 2020/0093926 A1 Mar. 26, 2020

Related U.S. Application Data

(62) Division of application No. 15/036,797, filed as application No. PCT/US2014/066418 on Nov. 19, 2014, now Pat. No. 10,537,635.

(60) Provisional application No. 61/906,150, filed on Nov. 19, 2013.

(51) Int. Cl.
| | |
|---|---|
| A61K 39/395 | (2006.01) |
| A61K 45/06 | (2006.01) |
| G01N 33/574 | (2006.01) |
| A61K 38/19 | (2006.01) |
| A61K 31/7076 | (2006.01) |
| G01N 33/566 | (2006.01) |
| C07K 16/32 | (2006.01) |
| A61K 39/00 | (2006.01) |

(52) U.S. Cl.
CPC .... *A61K 39/39558* (2013.01); *A61K 31/7076* (2013.01); *A61K 38/19* (2013.01); *A61K 45/06* (2013.01); *C07K 16/32* (2013.01); *G01N 33/566* (2013.01); *G01N 33/57492* (2013.01); *A61K 2039/505* (2013.01); *C07K 2317/24* (2013.01); *G01N 2333/82* (2013.01); *G01N 2800/52* (2013.01)

(58) Field of Classification Search
None
See application file for complete search history.

(56) References Cited

U.S. PATENT DOCUMENTS

2006/0235037 A1 10/2006 Purandare et al.
2013/0059892 A1 3/2013 Baiocchi et al.

OTHER PUBLICATIONS

Hsu et al. (Nature Cell Biology, vol. 13, No. 2, Feb. 2011, cited on IDS filed Mar. 7, 2021) (Year: 2011).*
Hsu et al. supplemental data (Nature Cell Biology, vol. 13, No. 2, Feb. 2011, cited on IDS filed Mar. 7, 2021) (Year: 2011).*
Bedford and Richard, "Arginine methylation: an emerging regulator of protein function," *Mol. Cell*, 18:263-272, 2005.
Berg and Soreide, "EGFR and downstream genetic alterations in KRAS/BRAF and PI3K/AKT pathways in colorectal cancer: implications for targeted therapy," *Discov. Med.*, 14:207-214, 2012.
Boisvert et al., "The GAR motif of 53BP1 is arginine methylated by PRMT1 and is necessary for 53BP1 DNA binding activity," *Cell Cycle*, 4:1834-1841, 2005.
Chung et al., "Spatial control of EGF receptor activation by reversible dimerization on living cells," *Nature*, 464:783-787, 2010.
Custodio and Feliu, "Prognostic and predictive biomarkers for epidermal growth factor receptor-targeted therapy in colorectal cancer: beyond KRAS mutations," *Crit. Rev. Oncol. Hematol.*, 85:45-81, 2013.
De Roock et al., "Association of KRAS p.G13D mutation with outcome in patients with chemotherapy-refractory metastatic colorectal cancer treated with cetuximab," *JAMA*, 304:1812-1820, 2010.
De Roock et al., "KRAS wild-type state predicts survival and is associated to early radiological response in metastatic colorectal cancer treated with cetuximab," *Ann. Oncol.*, 19:508-515, 2008.
Fabian and Berkovcova, "Molecular predictive markers of EGFR-targeted therapy in metastatic colorectal cancer," *Cesk. Fatal.*, 47:154-158, 2011.
Ferguson et al., "EGF activates its receptor by removing interactions that autoinhibit ectodomain dimerization," *Mol. Cell*, 11:507-517, 2003.
Gill et al., "Monoclonal anti-epidermal growth factor receptor antibodies which are inhibitors of epidermal growth factor binding and antagonists of epidermal growth factor binding and antagonists of epidermal growth factor-stimulated tyrosine protein kinase activity," *J. Biol. Chem.*, 259:7755-7760, 1984.
Hsieh et al., "Epidermal growth factor receptor R521K polymorphism shows favorable outcomes in KRAS wild-type colorectal cancer patients treated with cetuximab-based chemotherapy," *Cancer Sci.*, 103:791-796, 2012.
Hsu et al., "Crosstalk between Arg 1175 methylation and Tyr 1173 phosphorylation negatively modulates EGFR-mediated ERK activation," *Nat. Cell Biol.*, 13(2):174-181, 2011.
Laurent-Puig et al. "Analysis of PTEN, BRAF, and EGFR status in determining benefit from cetuximab therapy in wild-type KRAS metastatic colon cancer," *J. Clin. Oncol.*, 27:5924-5930, 2009.
Le Romancer et al., "Regulation of estrogen rapid signaling through arginine methylation by PRMT1," *Mol. Cell*, 31:212-221, 2008.
Li et al., "Structural basis for inhibition of the epidermal growth factor receptor by cetuximab," *Cancer Cell*, 7:301-311, 2005.
Lievre et al., "KRAS mutations as an independent prognostic factor in patients with advanced colorectal cancer treated with cetuximab," *J. Clin. Oncol.*, 26:374-379, 2008.

(Continued)

*Primary Examiner* — Meera Natarajan
(74) *Attorney, Agent, or Firm* — Parker Highlander PLLC

(57) ABSTRACT

This invention provides biomarkers (e.g., methylation of R198 or R200 of EGFR or the presence of an arginine at position 497 of EGFR) for the prediction of resistance to cetuximab therapy. This invention also provides methods for the selection of patients for combination therapy with cetuximab and PRMT inhibitors.

15 Claims, 36 Drawing Sheets

Specification includes a Sequence Listing.

(56) References Cited

OTHER PUBLICATIONS

Mao et al., "KRAS p.G13D mutation and codon 12 mutations are not created equal in predicting clinical outcomes of cetuximab in metastatic colorectal cancer: A systematic review and meta-analysis," *Cancer*, 119:714-721, 2013.
Mathioudaki et al., "The PRMT1 gene expression pattern in colon cancer," *Br. J. Cancer*, 99:2094-2099, 2008.
Messner et al., "KRAS p.G13D mutations are associated with sensitivity to anti-EGFR antibody treatment in colorectal cancer cell lines," *J. Cancer Res. Clin. Oncol.*, 139:201-209, 2013.
Morton and Hammond, "ASCO Provisional Clinical Opinion: KRAS, Cetuximab, and Panitumumab-Clinical Implications in Colorectal Cancer," *J. Oncol. Pract.*, 5:71-72, 2009.
Office Action issued in U.S. Appl. No. 15/036,797, dated Jul. 2, 2018.
Office Action issued in U.S. Appl. No. 15/036,797, dated May 16, 2019.
Office Action issued in U.S. Appl. No. 15/036,797, dated Nov. 16, 2018.
Ogiso et al., "Crystal structure of the complex of human epidermal growth factor and receptor extracellular domains," *Cell*, 110:775-787, 2002.
Papadokostopoulou et al., "Colon cancer and protein arginine methyltransferase 1 gene expression," *Anticancer Res.*, 29:1361-1366, 2009.
PCT International Preliminary Report on Patentability issued in International Application No. PCT/US2014/066418, dated May 24, 2016.
PCT International Search Report and Written Opinion issued in International Application No. PCT/US2014/066418, dated Feb. 19, 2015.
Pirker et al., "EGFR expression as a predictor of survival for first-line chemotherapy plus cetuximab in patients with advanced non-small-cell lung cancer: analysis of data from the phase 3 FLEX study," *Lancet Oncol.*, 13:33-42, 2012.
Scartozzi et al., "Epidermal growth factor receptor (EGFR) gene promoter methylation and cetuximab treatment in colorectal cancer patients," *British Journal of Cancer*, 104:1786-1790, 2011.
Silvestris et al., "KRAS mutations and sensitivity to anti-EGFR monoclonal antibodies in metastatic colorectal carcinoma: an open issue," *Expert Opin. Biol. Ther.*, 9:565-577, 2009.
Stoehlmacher-Williams et al., "Polymorphisms of the epidermal growth factor receptor (EGFR) and survival in patients with advanced cancer of the head and neck (HNSCC)," *Anticancer Res.*, 32(2):421-425, 2012.
Tejpar et al., "Association of KRAS G13D tumor mutations with outcome in patients with metastatic colorectal cancer treated with first-line chemotherapy with or without cetuximab," *J. Clin. Oncol.*, 30:3570-3577, 2012.
Van Houdt et al., "Oncogenic KRAS desensitizes colorectal tumor cells to epidermal growth factor receptor inhibition and activation," *Neoplasia*, 12:443-452, 2010.
Yang and Bedford, "Protein arginine methyltransferases and cancer," *Nat. Rev. Cancer*, 13:37-50, 2013.
Yonesake et al., "Activation of ERBB2 signaling causes resistance to the EGFR-directed therapeutic antibody cetuximab," *Sci. Transl. Med.*, 3(99):1-11, 2011.
Yu et al., "The MRE11 GAR motif regulates DNA double-strand break processing and ATR activation," *Cell Res.*, 22:305-320, 2012.

\* cited by examiner

| PRMT1 substrate | GAR motif | SEQ ID NO: |
|---|---|---|
| EGFR | 196-SGRCRGKSP-204 | 4 |
| p53 | 331-QIRGRERFE-339 | 5 |
| p80 coilon | 411-GMRGRGRGR-419 | 6 |
| Sm D1 | 98-RGRGRGRGR-106 | 7 |
| Sm D3 | 110-RGRGRGMGR-118 | 8 |
| Histone H4 | 1-MSGRG KGG-8 | 9 |
| Histone H3 | 7-TARKSTGGK-15 | 10 |

FIG. 2D a
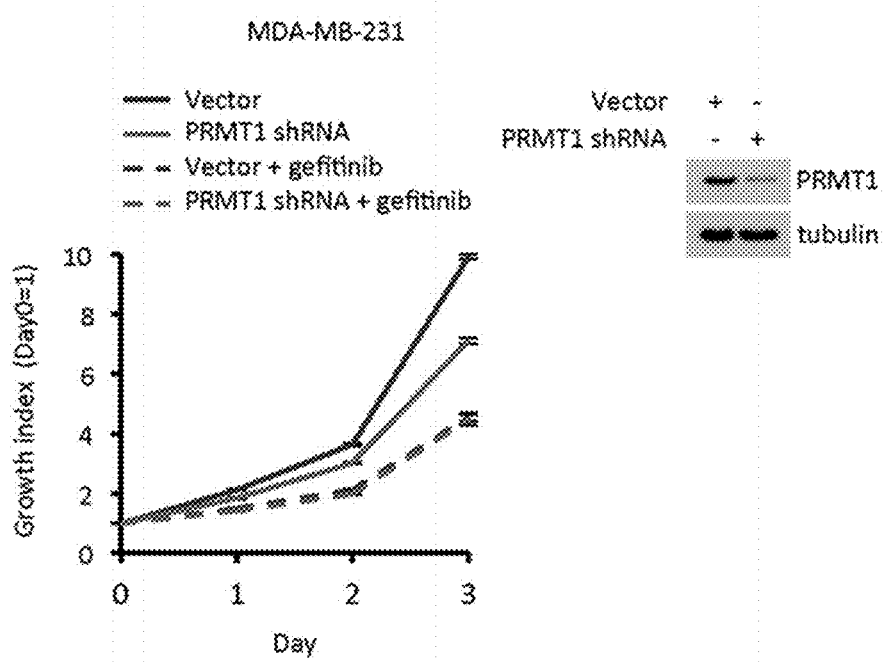
b
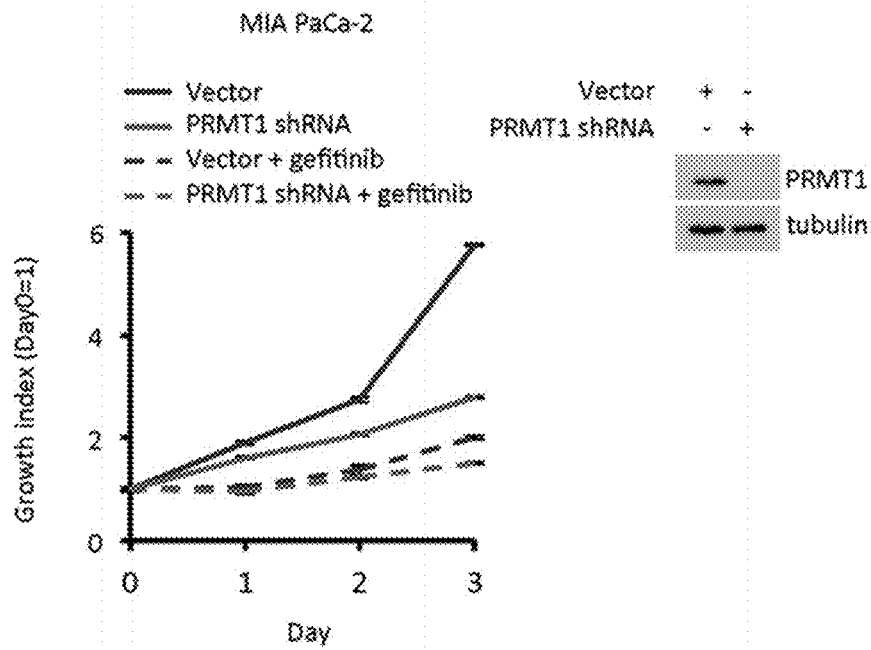
FIGS. 5A-B

FIGS. 7A-B

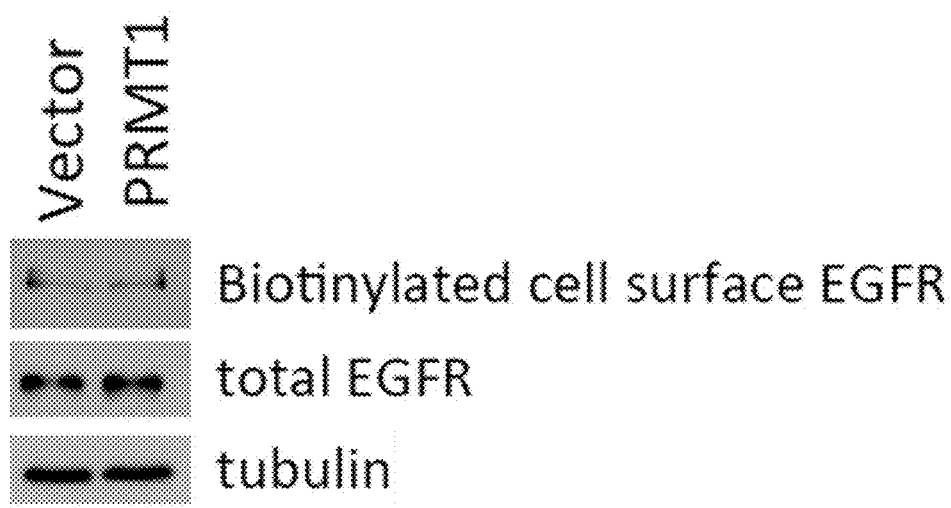
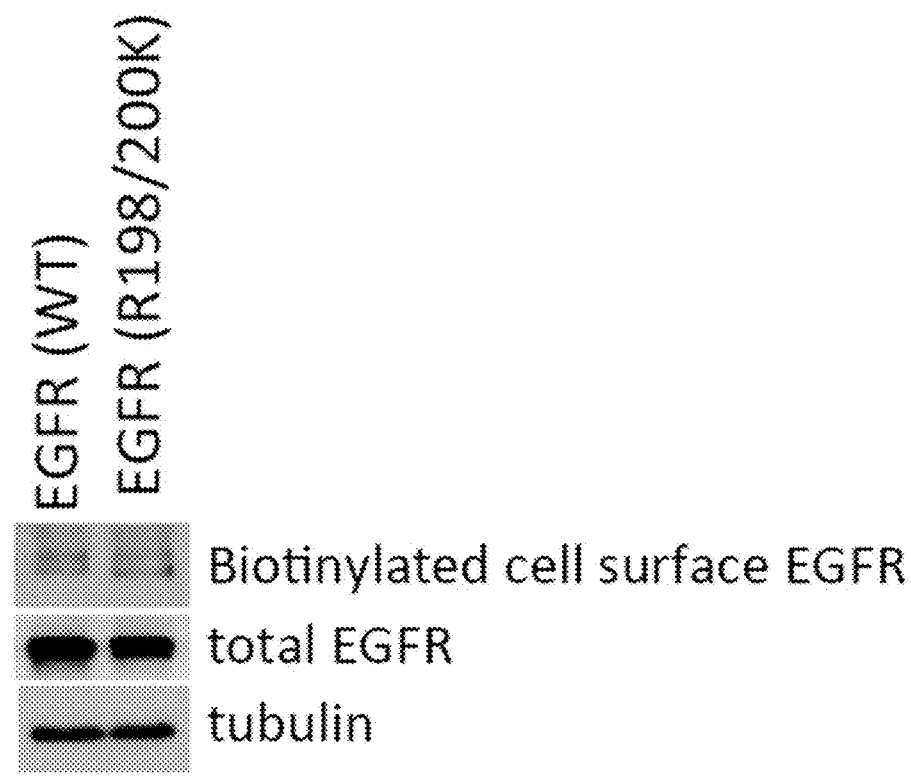
FIGS. 10A-B

SEQUENCE LISTING

<160> NUMBER OF SEQ ID NOS: 20

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Gln Cys Ser Gly Arg Cys Arg Gly Lys Ser Pro Ser Asp Cys
1               5                   10

<210> SEQ ID NO 2
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 2
ccggccggca gtacaaagac tacaactcga gttgtagtct ttgtactgcc ggttttttg     58

<210> SEQ ID NO 3
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 3
ccgggcaagt gaagcggaat gactactcga gtagtcattc cgcttcactt gcttttttg     58

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Ser Gly Arg Cys Arg Gly Lys Ser Pro
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Gln Ile Arg Gly Arg Glu Arg Phe Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Gly Met Arg Gly Arg Gly Arg Gly Arg
1               5

-continued

```
<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Arg Gly Arg Gly Arg Gly Arg Gly Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Arg Gly Arg Gly Arg Gly Met Gly Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Met Ser Gly Arg Gly Lys Gly Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Thr Ala Arg Lys Ser Thr Gly Gly Lys
1               5

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: METHYLATION
<220> FEATURE:
<221> NAME/KEY: MOD_RES
<222> LOCATION: (12)..(12)
<223> OTHER INFORMATION: METHYLATION

<400> SEQUENCE: 11

Ile Ile Cys Ala Gln Gln Cys Ser Gly Arg Cys Arg Gly Lys
1               5                   10

<210> SEQ ID NO 12
<211> LENGTH: 1210
<212> TYPE: PRT
<213> ORGANISM: Homo sapiens
<220> FEATURE:
<221> NAME/KEY: SIGNAL
```

```
<222> LOCATION: (1)..(24)
<220> FEATURE:
<221> NAME/KEY: mat_peptide
<222> LOCATION: (25)..(1210)

<400> SEQUENCE: 12
```

| | | | | | | | | | | | |
|---|---|---|---|---|---|---|---|---|---|---|---|
| Met | Arg | Pro | Ser | Gly | Thr | Ala | Gly | Ala | Ala | Leu | Leu | Ala | Leu | Leu | Ala |
| | | | | -20 | | | | | -15 | | | | | -10 | |

Met Arg Pro Ser Gly Thr Ala Gly Ala Ala Leu Leu Ala Leu Leu Ala
                -20                 -15                 -10

Ala Leu Cys Pro Ala Ser Arg Ala Leu Glu Glu Lys Lys Val Cys Gln
            -5              -1  1               5

Gly Thr Ser Asn Lys Leu Thr Gln Leu Gly Thr Phe Glu Asp His Phe
             10              15              20

Leu Ser Leu Gln Arg Met Phe Asn Asn Cys Glu Val Val Leu Gly Asn
 25                  30                  35                  40

Leu Glu Ile Thr Tyr Val Gln Arg Asn Tyr Asp Leu Ser Phe Leu Lys
                 45                  50                  55

Thr Ile Gln Glu Val Ala Gly Tyr Val Leu Ile Ala Leu Asn Thr Val
             60                  65                  70

Glu Arg Ile Pro Leu Glu Asn Leu Gln Ile Ile Arg Gly Asn Met Tyr
             75                  80                  85

Tyr Glu Asn Ser Tyr Ala Leu Ala Val Leu Ser Asn Tyr Asp Ala Asn
 90                  95                 100

Lys Thr Gly Leu Lys Glu Leu Pro Met Arg Asn Leu Gln Glu Ile Leu
105                 110                 115                 120

His Gly Ala Val Arg Phe Ser Asn Asn Pro Ala Leu Cys Asn Val Glu
                125                 130                 135

Ser Ile Gln Trp Arg Asp Ile Val Ser Ser Asp Phe Leu Ser Asn Met
                140                 145                 150

Ser Met Asp Phe Gln Asn His Leu Gly Ser Cys Gln Lys Cys Asp Pro
                155                 160                 165

Ser Cys Pro Asn Gly Ser Cys Trp Gly Ala Gly Glu Glu Asn Cys Gln
            170                 175                 180

Lys Leu Thr Lys Ile Ile Cys Ala Gln Gln Cys Ser Gly Arg Cys Arg
185                 190                 195                 200

Gly Lys Ser Pro Ser Asp Cys Cys His Asn Gln Cys Ala Ala Gly Cys
                205                 210                 215

Thr Gly Pro Arg Glu Ser Asp Cys Leu Val Cys Arg Lys Phe Arg Asp
                220                 225                 230

Glu Ala Thr Cys Lys Asp Thr Cys Pro Pro Leu Met Leu Tyr Asn Pro
                235                 240                 245

Thr Thr Tyr Gln Met Asp Val Asn Pro Glu Gly Lys Tyr Ser Phe Gly
            250                 255                 260

Ala Thr Cys Val Lys Lys Cys Pro Arg Asn Tyr Val Val Thr Asp His
265                 270                 275                 280

Gly Ser Cys Val Arg Ala Cys Gly Ala Asp Ser Tyr Glu Met Glu Glu
                285                 290                 295

Asp Gly Val Arg Lys Cys Lys Lys Cys Glu Gly Pro Cys Arg Lys Val
                300                 305                 310

Cys Asn Gly Ile Gly Ile Gly Glu Phe Lys Asp Ser Leu Ser Ile Asn
            315                 320                 325

Ala Thr Asn Ile Lys His Phe Lys Asn Cys Thr Ser Ile Ser Gly Asp
            330                 335                 340

Leu His Ile Leu Pro Val Ala Phe Arg Gly Asp Ser Phe Thr His Thr
345                 350                 355                 360

```
Pro Pro Leu Asp Pro Gln Glu Leu Asp Ile Leu Lys Thr Val Lys Glu
            365                 370                 375
Ile Thr Gly Phe Leu Leu Ile Gln Ala Trp Pro Glu Asn Arg Thr Asp
        380                 385                 390
Leu His Ala Phe Glu Asn Leu Glu Ile Ile Arg Gly Arg Thr Lys Gln
            395                 400                 405
His Gly Gln Phe Ser Leu Ala Val Val Ser Leu Asn Ile Thr Ser Leu
        410                 415                 420
Gly Leu Arg Ser Leu Lys Glu Ile Ser Asp Gly Asp Val Ile Ile Ser
425                 430                 435                 440
Gly Asn Lys Asn Leu Cys Tyr Ala Asn Thr Ile Asn Trp Lys Lys Leu
                445                 450                 455
Phe Gly Thr Ser Gly Gln Lys Thr Lys Ile Ile Ser Asn Arg Gly Glu
        460                 465                 470
Asn Ser Cys Lys Ala Thr Gly Gln Val Cys His Ala Leu Cys Ser Pro
            475                 480                 485
Glu Gly Cys Trp Gly Pro Glu Pro Arg Asp Cys Val Ser Cys Arg Asn
        490                 495                 500
Val Ser Arg Gly Arg Glu Cys Val Asp Lys Cys Asn Leu Leu Glu Gly
505                 510                 515                 520
Glu Pro Arg Glu Phe Val Glu Asn Ser Glu Cys Ile Gln Cys His Pro
                525                 530                 535
Glu Cys Leu Pro Gln Ala Met Asn Ile Thr Cys Thr Gly Arg Gly Pro
            540                 545                 550
Asp Asn Cys Ile Gln Cys Ala His Tyr Ile Asp Gly Pro His Cys Val
        555                 560                 565
Lys Thr Cys Pro Ala Gly Val Met Gly Glu Asn Asn Thr Leu Val Trp
570                 575                 580
Lys Tyr Ala Asp Ala Gly His Val Cys His Leu Cys His Pro Asn Cys
585                 590                 595                 600
Thr Tyr Gly Cys Thr Gly Pro Gly Leu Glu Gly Cys Pro Thr Asn Gly
                605                 610                 615
Pro Lys Ile Pro Ser Ile Ala Thr Gly Met Val Gly Ala Leu Leu Leu
            620                 625                 630
Leu Leu Val Val Ala Leu Gly Ile Gly Leu Phe Met Arg Arg Arg His
        635                 640                 645
Ile Val Arg Lys Arg Thr Leu Arg Arg Leu Leu Gln Glu Arg Glu Leu
        650                 655                 660
Val Glu Pro Leu Thr Pro Ser Gly Glu Ala Pro Asn Gln Ala Leu Leu
665                 670                 675                 680
Arg Ile Leu Lys Glu Thr Glu Phe Lys Lys Ile Lys Val Leu Gly Ser
                685                 690                 695
Gly Ala Phe Gly Thr Val Tyr Lys Gly Leu Trp Ile Pro Glu Gly Glu
            700                 705                 710
Lys Val Lys Ile Pro Val Ala Ile Lys Glu Leu Arg Glu Ala Thr Ser
        715                 720                 725
Pro Lys Ala Asn Lys Glu Ile Leu Asp Glu Ala Tyr Val Met Ala Ser
    730                 735                 740
Val Asp Asn Pro His Val Cys Arg Leu Leu Gly Ile Cys Leu Thr Ser
745                 750                 755                 760
Thr Val Gln Leu Ile Thr Gln Leu Met Pro Phe Gly Cys Leu Leu Asp
                765                 770                 775
Tyr Val Arg Glu His Lys Asp Asn Ile Gly Ser Gln Tyr Leu Leu Asn
```

```
              780             785             790
Trp Cys Val Gln Ile Ala Lys Gly Met Asn Tyr Leu Glu Asp Arg Arg
            795             800             805
Leu Val His Arg Asp Leu Ala Ala Arg Asn Val Leu Val Lys Thr Pro
            810             815             820
Gln His Val Lys Ile Thr Asp Phe Gly Leu Ala Lys Leu Leu Gly Ala
825             830             835             840
Glu Glu Lys Glu Tyr His Ala Glu Gly Gly Lys Val Pro Ile Lys Trp
            845             850             855
Met Ala Leu Glu Ser Ile Leu His Arg Ile Tyr Thr His Gln Ser Asp
            860             865             870
Val Trp Ser Tyr Gly Val Thr Val Trp Glu Leu Met Thr Phe Gly Ser
            875             880             885
Lys Pro Tyr Asp Gly Ile Pro Ala Ser Glu Ile Ser Ser Ile Leu Glu
            890             895             900
Lys Gly Glu Arg Leu Pro Gln Pro Pro Ile Cys Thr Ile Asp Val Tyr
905             910             915             920
Met Ile Met Val Lys Cys Trp Met Ile Asp Ala Asp Ser Arg Pro Lys
            925             930             935
Phe Arg Glu Leu Ile Ile Glu Phe Ser Lys Met Ala Arg Asp Pro Gln
            940             945             950
Arg Tyr Leu Val Ile Gln Gly Asp Glu Arg Met His Leu Pro Ser Pro
            955             960             965
Thr Asp Ser Asn Phe Tyr Arg Ala Leu Met Asp Glu Glu Asp Met Asp
            970             975             980
Asp Val Val Asp Ala Asp Glu Tyr Leu Ile Pro Gln Gln Gly Phe Phe
985             990             995             1000
Ser Ser Pro Ser Thr Ser Arg Thr Pro Leu Leu Ser Ser Leu Ser
            1005            1010            1015
Ala Thr Ser Asn Asn Ser Thr Val Ala Cys Ile Asp Arg Asn Gly
            1020            1025            1030
Leu Gln Ser Cys Pro Ile Lys Glu Asp Ser Phe Leu Gln Arg Tyr
            1035            1040            1045
Ser Ser Asp Pro Thr Gly Ala Leu Thr Glu Asp Ser Ile Asp Asp
            1050            1055            1060
Thr Phe Leu Pro Val Pro Glu Tyr Ile Asn Gln Ser Val Pro Lys
            1065            1070            1075
Arg Pro Ala Gly Ser Val Gln Asn Pro Val Tyr His Asn Gln Pro
            1080            1085            1090
Leu Asn Pro Ala Pro Ser Arg Asp Pro His Tyr Gln Asp Pro His
            1095            1100            1105
Ser Thr Ala Val Gly Asn Pro Glu Tyr Leu Asn Thr Val Gln Pro
            1110            1115            1120
Thr Cys Val Asn Ser Thr Phe Asp Ser Pro Ala His Trp Ala Gln
            1125            1130            1135
Lys Gly Ser His Gln Ile Ser Leu Asp Asn Pro Asp Tyr Gln Gln
            1140            1145            1150
Asp Phe Phe Pro Lys Glu Ala Lys Pro Asn Gly Ile Phe Lys Gly
            1155            1160            1165
Ser Thr Ala Glu Asn Ala Glu Tyr Leu Arg Val Ala Pro Gln Ser
            1170            1175            1180
Ser Glu Phe Ile Gly Ala
            1185
```

<210> SEQ ID NO 13
<211> LENGTH: 1186
<212> TYPE: PRT
<213> ORGANISM: Homo sapiens

<400> SEQUENCE: 13

```
Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
```

-continued

```
            370                 375                 380
Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
                435                 440                 445

Asn Thr Ile Asn Trp Lys Lys Leu Phe Gly Thr Ser Gly Gln Lys Thr
            450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
                500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser Ile Ala Thr
            610                 615                 620

Gly Met Val Gly Ala Leu Leu Leu Leu Val Val Ala Leu Gly Ile
625                 630                 635                 640

Gly Leu Phe Met Arg Arg Arg His Ile Val Arg Lys Arg Thr Leu Arg
                645                 650                 655

Arg Leu Leu Gln Glu Arg Glu Leu Val Glu Pro Leu Thr Pro Ser Gly
            660                 665                 670

Glu Ala Pro Asn Gln Ala Leu Leu Arg Ile Leu Lys Glu Thr Glu Phe
            675                 680                 685

Lys Lys Ile Lys Val Leu Gly Ser Gly Ala Phe Gly Thr Val Tyr Lys
            690                 695                 700

Gly Leu Trp Ile Pro Glu Gly Glu Lys Val Lys Ile Pro Val Ala Ile
705                 710                 715                 720

Lys Glu Leu Arg Glu Ala Thr Ser Pro Lys Ala Asn Lys Glu Ile Leu
                725                 730                 735

Asp Glu Ala Tyr Val Met Ala Ser Val Asp Asn Pro His Val Cys Arg
                740                 745                 750

Leu Leu Gly Ile Cys Leu Thr Ser Thr Val Gln Leu Ile Thr Gln Leu
            755                 760                 765

Met Pro Phe Gly Cys Leu Leu Asp Tyr Val Arg Glu His Lys Asp Asn
            770                 775                 780

Ile Gly Ser Gln Tyr Leu Leu Asn Trp Cys Val Gln Ile Ala Lys Gly
785                 790                 795                 800
```

Met Asn Tyr Leu Glu Asp Arg Arg Leu Val His Arg Asp Leu Ala Ala
                805                 810                 815

Arg Asn Val Leu Val Lys Thr Pro Gln His Val Lys Ile Thr Asp Phe
            820                 825                 830

Gly Leu Ala Lys Leu Leu Gly Ala Glu Glu Lys Glu Tyr His Ala Glu
            835                 840                 845

Gly Gly Lys Val Pro Ile Lys Trp Met Ala Leu Glu Ser Ile Leu His
        850                 855                 860

Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
                885                 890                 895

Ser Glu Ile Ser Ser Ile Leu Glu Lys Gly Glu Arg Leu Pro Gln Pro
            900                 905                 910

Pro Ile Cys Thr Ile Asp Val Tyr Met Ile Met Val Lys Cys Trp Met
            915                 920                 925

Ile Asp Ala Asp Ser Arg Pro Lys Phe Arg Glu Leu Ile Ile Glu Phe
        930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
                965                 970                 975

Leu Met Asp Glu Glu Asp Met Asp Asp Val Val Asp Ala Asp Glu Tyr
            980                 985                 990

Leu Ile Pro Gln Gln Gly Phe Phe Ser Ser Pro Ser Thr Ser Arg Thr
            995                 1000                1005

Pro Leu Leu Ser Ser Leu Ser Ala Thr Ser Asn Asn Ser Thr Val
        1010                1015                1020

Ala Cys Ile Asp Arg Asn Gly Leu Gln Ser Cys Pro Ile Lys Glu
        1025                1030                1035

Asp Ser Phe Leu Gln Arg Tyr Ser Ser Asp Pro Thr Gly Ala Leu
        1040                1045                1050

Thr Glu Asp Ser Ile Asp Asp Thr Phe Leu Pro Val Pro Glu Tyr
        1055                1060                1065

Ile Asn Gln Ser Val Pro Lys Arg Pro Ala Gly Ser Val Gln Asn
        1070                1075                1080

Pro Val Tyr His Asn Gln Pro Leu Asn Pro Ala Pro Ser Arg Asp
        1085                1090                1095

Pro His Tyr Gln Asp Pro His Ser Thr Ala Val Gly Asn Pro Glu
        1100                1105                1110

Tyr Leu Asn Thr Val Gln Pro Thr Cys Val Asn Ser Thr Phe Asp
        1115                1120                1125

Ser Pro Ala His Trp Ala Gln Lys Gly Ser His Gln Ile Ser Leu
        1130                1135                1140

Asp Asn Pro Asp Tyr Gln Gln Asp Phe Phe Pro Lys Glu Ala Lys
        1145                1150                1155

Pro Asn Gly Ile Phe Lys Gly Ser Thr Ala Glu Asn Ala Glu Tyr
        1160                1165                1170

Leu Arg Val Ala Pro Gln Ser Ser Glu Phe Ile Gly Ala
        1175                1180                1185

<210> SEQ ID NO 14
<211> LENGTH: 628

```
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: mat_peptide
<222> LOCATION: (25)..(628)

<400> SEQUENCE: 14

Met Arg Pro Ser Gly Thr Ala Gly Ala Ala Leu Leu Ala Leu Leu Ala
                -20             -15                 -10

Ala Leu Cys Pro Ala Ser Arg Ala Leu Glu Glu Lys Lys Val Cys Gln
            -5              -1  1               5

Gly Thr Ser Asn Lys Leu Thr Gln Leu Gly Thr Phe Glu Asp His Phe
             10              15              20

Leu Ser Leu Gln Arg Met Phe Asn Asn Cys Glu Val Val Leu Gly Asn
 25              30              35                          40

Leu Glu Ile Thr Tyr Val Gln Arg Asn Tyr Asp Leu Ser Phe Leu Lys
                 45              50                  55

Thr Ile Gln Glu Val Ala Gly Tyr Val Leu Ile Ala Leu Asn Thr Val
             60              65              70

Glu Arg Ile Pro Leu Glu Asn Leu Gln Ile Ile Arg Gly Asn Met Tyr
             75              80              85

Tyr Glu Asn Ser Tyr Ala Leu Ala Val Leu Ser Asn Tyr Asp Ala Asn
 90              95              100

Lys Thr Gly Leu Lys Glu Leu Pro Met Arg Asn Leu Gln Glu Ile Leu
105             110             115                         120

His Gly Ala Val Arg Phe Ser Asn Asn Pro Ala Leu Cys Asn Val Glu
             125             130             135

Ser Ile Gln Trp Arg Asp Ile Val Ser Ser Asp Phe Leu Ser Asn Met
             140             145             150

Ser Met Asp Phe Gln Asn His Leu Gly Ser Cys Gln Lys Cys Asp Pro
             155             160             165

Ser Cys Pro Asn Gly Ser Cys Trp Gly Ala Gly Glu Glu Asn Cys Gln
             170             175             180

Lys Leu Thr Lys Ile Ile Cys Ala Gln Gln Cys Ser Gly Arg Cys Arg
185             190             195                         200

Gly Lys Ser Pro Ser Asp Cys Cys His Asn Gln Cys Ala Ala Gly Cys
             205             210             215

Thr Gly Pro Arg Glu Ser Asp Cys Leu Val Cys Arg Lys Phe Arg Asp
             220             225             230

Glu Ala Thr Cys Lys Asp Thr Cys Pro Pro Leu Met Leu Tyr Asn Pro
             235             240             245

Thr Thr Tyr Gln Met Asp Val Asn Pro Glu Gly Lys Tyr Ser Phe Gly
             250             255             260

Ala Thr Cys Val Lys Lys Cys Pro Arg Asn Tyr Val Val Thr Asp His
265             270             275                         280

Gly Ser Cys Val Arg Ala Cys Gly Ala Asp Ser Tyr Glu Met Glu Glu
             285             290             295

Asp Gly Val Arg Lys Cys Lys Lys Cys Glu Gly Pro Cys Arg Lys Val
             300             305             310

Cys Asn Gly Ile Gly Ile Gly Glu Phe Lys Asp Ser Leu Ser Ile Asn
             315             320             325

Ala Thr Asn Ile Lys His Phe Lys Asn Cys Thr Ser Ile Ser Gly Asp
             330             335             340
```

```
Leu His Ile Leu Pro Val Ala Phe Arg Gly Asp Ser Phe Thr His Thr
345                 350                 355                 360

Pro Pro Leu Asp Pro Gln Glu Leu Asp Ile Leu Lys Thr Val Lys Glu
                365                 370                 375

Ile Thr Gly Phe Leu Leu Ile Gln Ala Trp Pro Glu Asn Arg Thr Asp
            380                 385                 390

Leu His Ala Phe Glu Asn Leu Glu Ile Ile Arg Gly Arg Thr Lys Gln
        395                 400                 405

His Gly Gln Phe Ser Leu Ala Val Val Ser Leu Asn Ile Thr Ser Leu
    410                 415                 420

Gly Leu Arg Ser Leu Lys Glu Ile Ser Asp Gly Asp Val Ile Ile Ser
425                 430                 435                 440

Gly Asn Lys Asn Leu Cys Tyr Ala Asn Thr Ile Asn Trp Lys Lys Leu
                445                 450                 455

Phe Gly Thr Ser Gly Gln Lys Thr Lys Ile Ile Ser Asn Arg Gly Glu
            460                 465                 470

Asn Ser Cys Lys Ala Thr Gly Gln Val Cys His Ala Leu Cys Ser Pro
        475                 480                 485

Glu Gly Cys Trp Gly Pro Glu Pro Arg Asp Cys Val Ser Cys Arg Asn
    490                 495                 500

Val Ser Arg Gly Arg Glu Cys Val Asp Lys Cys Asn Leu Leu Glu Gly
505                 510                 515                 520

Glu Pro Arg Glu Phe Val Glu Asn Ser Glu Cys Ile Gln Cys His Pro
                525                 530                 535

Glu Cys Leu Pro Gln Ala Met Asn Ile Thr Cys Thr Gly Arg Gly Pro
            540                 545                 550

Asp Asn Cys Ile Gln Cys Ala His Tyr Ile Asp Gly Pro His Cys Val
        555                 560                 565

Lys Thr Cys Pro Ala Gly Val Met Gly Glu Asn Asn Thr Leu Val Trp
    570                 575                 580

Lys Tyr Ala Asp Ala Gly His Val Cys His Leu Cys His Pro Asn Cys
585                 590                 595                 600

Thr Tyr Gly Ser

<210> SEQ ID NO 15
<211> LENGTH: 604
<212> TYPE: PRT
<213> ORGANISM: Homo sapiens

<400> SEQUENCE: 15

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110
```

Met Arg Asn Leu Gln Glu Ile Leu His Gly Ala Val Arg Phe Ser Asn
            115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

-continued

```
Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Ser
            595                 600

<210> SEQ ID NO 16
<211> LENGTH: 405
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: mat_peptide
<222> LOCATION: (25)..(405)

<400> SEQUENCE: 16

Met Arg Pro Ser Gly Thr Ala Gly Ala Ala Leu Leu Ala Leu Leu Ala
                -20                 -15                 -10

Ala Leu Cys Pro Ala Ser Arg Ala Leu Glu Glu Lys Lys Val Cys Gln
            -5                  -1   1               5

Gly Thr Ser Asn Lys Leu Thr Gln Leu Gly Thr Phe Glu Asp His Phe
        10                  15                  20

Leu Ser Leu Gln Arg Met Phe Asn Asn Cys Glu Val Val Leu Gly Asn
 25                  30                  35                  40

Leu Glu Ile Thr Tyr Val Gln Arg Asn Tyr Asp Leu Ser Phe Leu Lys
                45                  50                  55

Thr Ile Gln Glu Val Ala Gly Tyr Val Leu Ile Ala Leu Asn Thr Val
                60                  65                  70

Glu Arg Ile Pro Leu Glu Asn Leu Gln Ile Ile Arg Gly Asn Met Tyr
            75                  80                  85

Tyr Glu Asn Ser Tyr Ala Leu Ala Val Leu Ser Asn Tyr Asp Ala Asn
    90                  95                  100

Lys Thr Gly Leu Lys Glu Leu Pro Met Arg Asn Leu Gln Glu Ile Leu
105                 110                 115                 120

His Gly Ala Val Arg Phe Ser Asn Asn Pro Ala Leu Cys Asn Val Glu
                125                 130                 135

Ser Ile Gln Trp Arg Asp Ile Val Ser Ser Asp Phe Leu Ser Asn Met
                140                 145                 150

Ser Met Asp Phe Gln Asn His Leu Gly Ser Cys Gln Lys Cys Asp Pro
            155                 160                 165

Ser Cys Pro Asn Gly Ser Cys Trp Gly Ala Gly Glu Glu Asn Cys Gln
    170                 175                 180

Lys Leu Thr Lys Ile Ile Cys Ala Gln Gln Cys Ser Gly Arg Cys Arg
185                 190                 195                 200

Gly Lys Ser Pro Ser Asp Cys Cys His Asn Gln Cys Ala Ala Gly Cys
                205                 210                 215

Thr Gly Pro Arg Glu Ser Asp Cys Leu Val Cys Arg Lys Phe Arg Asp
            220                 225                 230

Glu Ala Thr Cys Lys Asp Thr Cys Pro Pro Leu Met Leu Tyr Asn Pro
        235                 240                 245
```

```
Thr Thr Tyr Gln Met Asp Val Asn Pro Glu Gly Lys Tyr Ser Phe Gly
    250                 255                 260

Ala Thr Cys Val Lys Lys Cys Pro Arg Asn Tyr Val Val Thr Asp His
265                 270                 275                 280

Gly Ser Cys Val Arg Ala Cys Gly Ala Asp Ser Tyr Glu Met Glu Glu
                285                 290                 295

Asp Gly Val Arg Lys Cys Lys Lys Cys Glu Gly Pro Cys Arg Lys Val
                300                 305                 310

Cys Asn Gly Ile Gly Ile Gly Glu Phe Lys Asp Ser Leu Ser Ile Asn
                315                 320                 325

Ala Thr Asn Ile Lys His Phe Lys Asn Cys Thr Ser Ile Ser Gly Asp
        330                 335                 340

Leu His Ile Leu Pro Val Ala Phe Arg Gly Asp Ser Phe Thr His Thr
345                 350                 355                 360

Pro Pro Leu Asp Pro Gln Glu Leu Asp Ile Leu Lys Thr Val Lys Glu
                365                 370                 375

Ile Thr Gly Leu Ser
            380

<210> SEQ ID NO 17
<211> LENGTH: 381
<212> TYPE: PRT
<213> ORGANISM: Homo sapiens

<400> SEQUENCE: 17

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
```

```
                    225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
                275                 280                 285

Ala Asp Ser Tyr Glu Met Glu Glu Asp Gly Val Arg Lys Cys Lys Lys
                290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
                355                 360                 365

Asp Ile Leu Lys Thr Val Lys Glu Ile Thr Gly Leu Ser
370                 375                 380

<210> SEQ ID NO 18
<211> LENGTH: 705
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: mat_peptide
<222> LOCATION: (25)..(705)

<400> SEQUENCE: 18

Met Arg Pro Ser Gly Thr Ala Gly Ala Ala Leu Leu Ala Leu Leu Ala
                -20                 -15                 -10

Ala Leu Cys Pro Ala Ser Arg Ala Leu Glu Glu Lys Lys Val Cys Gln
                -5                  -1  1               5

Gly Thr Ser Asn Lys Leu Thr Gln Leu Gly Thr Phe Glu Asp His Phe
10                  15                  20

Leu Ser Leu Gln Arg Met Phe Asn Asn Cys Glu Val Val Leu Gly Asn
25                  30                  35                  40

Leu Glu Ile Thr Tyr Val Gln Arg Asn Tyr Asp Leu Ser Phe Leu Lys
                45                  50                  55

Thr Ile Gln Glu Val Ala Gly Tyr Val Leu Ile Ala Leu Asn Thr Val
                60                  65                  70

Glu Arg Ile Pro Leu Glu Asn Leu Gln Ile Ile Arg Gly Asn Met Tyr
                75                  80                  85

Tyr Glu Asn Ser Tyr Ala Leu Ala Val Leu Ser Asn Tyr Asp Ala Asn
                90                  95                  100

Lys Thr Gly Leu Lys Glu Leu Pro Met Arg Asn Leu Gln Glu Ile Leu
105                 110                 115                 120

His Gly Ala Val Arg Phe Ser Asn Asn Pro Ala Leu Cys Asn Val Glu
                125                 130                 135

Ser Ile Gln Trp Arg Asp Ile Val Ser Ser Asp Phe Leu Ser Asn Met
                140                 145                 150

Ser Met Asp Phe Gln Asn His Leu Gly Ser Cys Gln Lys Cys Asp Pro
                155                 160                 165
```

-continued

Ser Cys Pro Asn Gly Ser Cys Trp Gly Ala Gly Glu Glu Asn Cys Gln
170                 175                 180

Lys Leu Thr Lys Ile Ile Cys Ala Gln Gln Cys Ser Gly Arg Cys Arg
185                 190                 195                 200

Gly Lys Ser Pro Ser Asp Cys Cys His Asn Gln Cys Ala Ala Gly Cys
                205                 210                 215

Thr Gly Pro Arg Glu Ser Asp Cys Leu Val Cys Arg Lys Phe Arg Asp
                220                 225                 230

Glu Ala Thr Cys Lys Asp Thr Cys Pro Pro Leu Met Leu Tyr Asn Pro
            235                 240                 245

Thr Thr Tyr Gln Met Asp Val Asn Pro Glu Gly Lys Tyr Ser Phe Gly
250                 255                 260

Ala Thr Cys Val Lys Lys Cys Pro Arg Asn Tyr Val Val Thr Asp His
265                 270                 275                 280

Gly Ser Cys Val Arg Ala Cys Gly Ala Asp Ser Tyr Glu Met Glu Glu
                285                 290                 295

Asp Gly Val Arg Lys Cys Lys Lys Cys Glu Gly Pro Cys Arg Lys Val
            300                 305                 310

Cys Asn Gly Ile Gly Ile Gly Glu Phe Lys Asp Ser Leu Ser Ile Asn
        315                 320                 325

Ala Thr Asn Ile Lys His Phe Lys Asn Cys Thr Ser Ile Ser Gly Asp
330                 335                 340

Leu His Ile Leu Pro Val Ala Phe Arg Gly Asp Ser Phe Thr His Thr
345                 350                 355                 360

Pro Pro Leu Asp Pro Gln Glu Leu Asp Ile Leu Lys Thr Val Lys Glu
                365                 370                 375

Ile Thr Gly Phe Leu Leu Ile Gln Ala Trp Pro Glu Asn Arg Thr Asp
            380                 385                 390

Leu His Ala Phe Glu Asn Leu Glu Ile Ile Arg Gly Arg Thr Lys Gln
        395                 400                 405

His Gly Gln Phe Ser Leu Ala Val Val Ser Leu Asn Ile Thr Ser Leu
410                 415                 420

Gly Leu Arg Ser Leu Lys Glu Ile Ser Asp Gly Asp Val Ile Ile Ser
425                 430                 435                 440

Gly Asn Lys Asn Leu Cys Tyr Ala Asn Thr Ile Asn Trp Lys Lys Leu
                445                 450                 455

Phe Gly Thr Ser Gly Gln Lys Thr Lys Ile Ile Ser Asn Arg Gly Glu
            460                 465                 470

Asn Ser Cys Lys Ala Thr Gly Gln Val Cys His Ala Leu Cys Ser Pro
        475                 480                 485

Glu Gly Cys Trp Gly Pro Glu Pro Arg Asp Cys Val Ser Cys Arg Asn
490                 495                 500

Val Ser Arg Gly Arg Glu Cys Val Asp Lys Cys Asn Leu Leu Glu Gly
505                 510                 515                 520

Glu Pro Arg Glu Phe Val Glu Asn Ser Glu Cys Ile Gln Cys His Pro
                525                 530                 535

Glu Cys Leu Pro Gln Ala Met Asn Ile Thr Cys Thr Gly Arg Gly Pro
            540                 545                 550

Asp Asn Cys Ile Gln Cys Ala His Tyr Ile Asp Gly Pro His Cys Val
        555                 560                 565

Lys Thr Cys Pro Ala Gly Val Met Gly Glu Asn Asn Thr Leu Val Trp
570                 575                 580

Lys Tyr Ala Asp Ala Gly His Val Cys His Leu Cys His Pro Asn Cys

```
                    585                 590                 595                 600
Thr Tyr Gly Pro Gly Asn Glu Ser Leu Lys Ala Met Leu Phe Cys Leu
                605                 610                 615

Phe Lys Leu Ser Ser Cys Asn Gln Ser Asn Asp Gly Ser Val Ser His
                620                 625                 630

Gln Ser Gly Ser Pro Ala Ala Gln Glu Ser Cys Leu Gly Trp Ile Pro
                635                 640                 645

Ser Leu Leu Pro Ser Glu Phe Gln Leu Gly Trp Gly Gly Cys Ser His
                650                 655                 660

Leu His Ala Trp Pro Ser Ala Ser Val Ile Ile Thr Ala Ser Ser Cys
665                 670                 675                 680

His

<210> SEQ ID NO 19
<211> LENGTH: 681
<212> TYPE: PRT
<213> ORGANISM: Homo sapiens

<400> SEQUENCE: 19

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
```

-continued

```
            275                 280                 285
Ala Asp Ser Tyr Glu Met Glu Glu Asp Gly Val Arg Lys Cys Lys Lys
    290                 295                 300
Cys Glu Gly Pro Cys Arg Lys Val Cys Asn Gly Ile Gly Ile Gly Glu
305                 310                 315                 320
Phe Lys Asp Ser Leu Ser Ile Asn Ala Thr Asn Ile Lys His Phe Lys
                325                 330                 335
Asn Cys Thr Ser Ile Ser Gly Asp Leu His Ile Leu Pro Val Ala Phe
                340                 345                 350
Arg Gly Asp Ser Phe Thr His Thr Pro Pro Leu Asp Pro Gln Glu Leu
                355                 360                 365
Asp Ile Leu Lys Thr Val Lys Glu Ile Thr Gly Phe Leu Leu Ile Gln
            370                 375                 380
Ala Trp Pro Glu Asn Arg Thr Asp Leu His Ala Phe Glu Asn Leu Glu
385                 390                 395                 400
Ile Ile Arg Gly Arg Thr Lys Gln His Gly Gln Phe Ser Leu Ala Val
                405                 410                 415
Val Ser Leu Asn Ile Thr Ser Leu Gly Leu Arg Ser Leu Lys Glu Ile
                420                 425                 430
Ser Asp Gly Asp Val Ile Ile Ser Gly Asn Lys Asn Leu Cys Tyr Ala
            435                 440                 445
Asn Thr Ile Asn Trp Lys Lys Leu Phe Gly Thr Ser Gly Gln Lys Thr
450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Arg Asn Val Ser Arg Gly Arg Glu Cys Val
                500                 505                 510
Asp Lys Cys Asn Leu Leu Glu Gly Glu Pro Arg Glu Phe Val Glu Asn
                515                 520                 525
Ser Glu Cys Ile Gln Cys His Pro Glu Cys Leu Pro Gln Ala Met Asn
            530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
                565                 570                 575
Gly Glu Asn Asn Thr Leu Val Trp Lys Tyr Ala Asp Ala Gly His Val
                580                 585                 590
Cys His Leu Cys His Pro Asn Cys Thr Tyr Gly Pro Gly Asn Glu Ser
            595                 600                 605
Leu Lys Ala Met Leu Phe Cys Leu Phe Lys Leu Ser Ser Cys Asn Gln
            610                 615                 620
Ser Asn Asp Gly Ser Val Ser His Gln Ser Gly Ser Pro Ala Ala Gln
625                 630                 635                 640
Glu Ser Cys Leu Gly Trp Ile Pro Ser Leu Leu Pro Ser Glu Phe Gln
                645                 650                 655
Leu Gly Trp Gly Gly Cys Ser His Leu His Ala Trp Pro Ser Ala Ser
                660                 665                 670
Val Ile Ile Thr Ala Ser Ser Cys His
            675                 680
```

<210> SEQ ID NO 20

```
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (21)..(21)
<223> OTHER INFORMATION: METHYLATION

<400> SEQUENCE: 20

Ala Thr Gly Gln Val Cys His Ala Leu Cys Ser Pro Glu Gly Cys Trp
1               5                   10                  15

Gly Pro Glu Pro Arg
            20
```

DETECTION OF ARGININE METHYLATION OF EGFR FOR PREDICTION OF RESISTANCE TO THERAPY

This application is a divisional of U.S. application Ser. No. 15/036,797, filed May 13, 2016, which is a national phase application under 35 U.S.C. § 371 of International Application No. PCT/US2014/066418, filed Nov. 19, 2014, which claims the benefit of U.S. Provisional Patent Application No. 61/906,150, filed Nov. 19, 2013, each of which is incorporated herein by reference in its entirety.

The sequence listing that is contained in the file names "UTSCP1232USD1.txt", which is 53 KB (as measured in Microsoft Windows) and was created on Dec. 4, 2019, is filed herewith by electronic submission and is incorporated by reference herein.

BACKGROUND OF THE INVENTION

1. Field of the Invention

The present invention relates generally to the field of oncology. More particularly, it concerns the detection of arginine methylation of EGFR to predict resistance to cetuximab therapy and sensitivity to a combination therapy using a PRMT inhibitor plus cetuximab.

2. Description of Related Art

Epidermal growth factor receptor (EGFR)-targeted monoclonal antibody, cetuximab, is one of the most effective ways of controlling colorectal cancer progression (Berg and Soreide, 2012). However, resistance to cetuximab has been observed in the clinic (Custodio and Feliu, 2013; Fabian and Berkovcova, 2011; Messner et al., 2013). Currently, the most accepted predictive marker for poor cetuximab response in colorectal cancer is mutant KRAS status due its association with poor patient survival rate (De Roock et al., 2008; Lievre et al., 2008). Nevertheless, studies show increasing evidence that wild-type KRAS is insufficient to confer sensitivity to cetuximab (Fabian and Berkovcova, 2011; Laurent-Puig et al., 2009; Silvestris et al., 2009) and that patients with mutant KRAS are not necessarily refractory to cetuximab (Custodio and Feliu, 2013; Messner et al., 2013; Mao et al., 2013; Tejpar et al., 2013; De Roock et al., 2010). Therefore, other predictors of cetuximab response are needed.

SUMMARY OF THE INVENTION

In order to address this need, provided herein are biomarkers for the prediction of resistance to cetuximab therapy. Also provided are methods for the selection of patients for combination therapy with cetuximab and PRMT inhibitors. Therefore, in one embodiment, a pharmaceutical composition is provided comprising cetuximab and a protein arginine methyltransferase (PRMT) inhibitor (e.g., sinefungin, S-adenosylhomocysteine, AMI-1, AMI-408, MDL 28,842, methylthioadenosine, C21, Eosin Y, disodium trihydrate, Cpd4, or adenosine dialdehyde) in a pharmaceutically acceptable carrier. In one embodiment, a method is provide for treating cancer comprising administering said pharmaceutical composition to a patient in need thereof.

In one embodiment, a method is provided for treating a patient having cancer comprising administering an effective amount of cetuximab and a protein arginine methyltransferase (PRMT) inhibitor to a patient in need thereof. In some aspects, the PRMT inhibitor may be sinefungin, S-adenosylhomocysteine, AMI-1, AMI-408, MDL 28,842, methylthioadenosine, C21, Eosin Y, disodium trihydrate, Cpd4, or adenosine dialdehyde. In some aspects, cetuximab and the PRMT inhibitor may be administered essentially simultaneously. In certain aspects, cetuximab may be administered prior to the PRMT inhibitor. In other certain aspects, the PRMT inhibitor may be administered prior to cetuximab.

In some aspects, the patient may have been determined to have a cancer cell comprising at least one of (i) methylated Arg at position 198, (ii) methylated Arg at position 200, and/or (iii) an Arg residue at amino acid position 497 of epidermal growth factor receptor (EGFR) protein. In certain aspects, the cancer cell may be from a biopsy sample. In other aspects, the cancer cell may be a circulating tumor cell.

In certain aspects, the presence of (i) methylated Arg at position 198 and/or (ii) methylated Arg at position 200 of EGFR protein may be detected by mass spectrometry, ELISA, flow cytometry, immunohistochemistry, western blot, radioimmunoassay, or immunoprecipitation. In certain aspects, the presence of (i) methylated Arg at position 198 and/or (ii) methylated Arg at position 200 of EGFR protein may be detecting by a method comprising contacting the sample with an antibody that binds specifically to EGFR methylated at Arg198 and/or Arg200. As a control, the overall level of EGFR may be determined by a method comprising contacting the sample with an antibody that binds to EGFR regardless of the presence or absence of any post-translational modifications. In some aspects, the presence of (iii) an Arg residue at amino acid position 497 of EGFR protein may be determined by mass spectrometry or by sequencing a nucleic acid comprising at least a portion of the protein coding sequence of the EGFR protein.

In one embodiment, a method is provided for treating a patient having cancer comprising administering an effective amount of cetuximab to a patient in need thereof, said patient having been determined to have a cancer cell comprising (i) unmethylated Arg at position 198, (ii) unmethylated Arg at position 200, and (iii) a Lys residue at amino acid position 497 of EGFR protein. In certain aspects, the cancer cell may be from a biopsy sample. In other aspects, the cancer cell may be a circulating tumor cell.

In certain aspects, the presence of (i) unmethylated Arg at position 198 and/or (ii) unmethylated Arg at position 200 of EGFR protein may be detected by mass spectrometry, ELISA, flow cytometry, immunohistochemistry, western blot, radioimmunoassay, or immunoprecipitation. In certain aspects, the presence of (i) unmethylated Arg at position 198 and/or (ii) unmethylated Arg at position 200 of EGFR protein may be detecting by a method comprising contacting the sample with an antibody that binds specifically to EGFR methylated at Arg198 and/or Arg200. As a control, the overall level of EGFR may be determined by a method comprising contacting the sample with an antibody that binds to EGFR regardless of the presence or absence of any post-translational modifications. In some aspects, the presence of (iii) a Lys residue at amino acid position 497 of EGFR protein may be determined by mass spectrometry or by sequencing a nucleic acid comprising at least a portion of the protein coding sequence of the EGFR protein.

In one embodiment, a method is provided for predicting resistance of a cancer patient to cetuximab comprising assaying a cancer cell (e.g., from a biopsy sample or a circulating tumor cell) isolated from the patient to determine the presence of at least one of (i) methylated Arg at position 198, (ii) methylated Arg at position 200, and/or (iii) an Arg residue at amino acid position 497 of EGFR protein in the cancer cell. In some aspects, if at least one of (i) methylated Arg at position 198, (ii) methylated Arg at position 200, and/or (iii) an Arg residue at amino acid position 497 of EGFR protein is present, then the cancer may be predicted to be resistant to cetuximab.

In some aspects, the method may further comprise identifying the patient as having a cancer that is resistant to cetuxmiab if at least one of (i) methylated Arg at position 198, (ii) methylated Arg at position 200, and/or (iii) an Arg residue at amino acid position 497 of EGFR protein is present. In some aspects, identifying may comprise reporting (i.e., preparing a written or an oral report) whether the patient has a cancer that is resistant to cetuximab Said reporting may be reporting to the patient, a doctor, a hospital, or an insurance provider.

In some aspects, identifying the patient as having a cancer that is resistant to cetuxmiab may further comprise identifying the patient having the cancer as a candidate for treatment with a combination of cetuximab and a PRMT inhibitor. In some aspects, the method may further comprise treating the patient with cetuximab in combination with a PRMT inhibitor, such as, for example, sinefungin, S-adenosylhomocysteine, AMI-1, AMI-408, MDL 28,842, methylthioadenosine, C21, Eosin Y, disodium trihydrate, Cpd4, or adenosine dialdehyde. In some aspects, cetuximab and the PRMT inhibitor may be administered essentially simultaneously. In certain aspects, cetuximab may be administered prior to the PRMT inhibitor. In other certain aspects, the PRMT inhibitor may be administered prior to cetuximab.

In some aspects, the presence of (i) methylated Arg at position 198 and/or (ii) methylated Arg at position 200 may comprise contacting the sample with an antibody that binds specifically to EGFR methylated at Arg198 and/or Arg200. In some aspects, assaying may comprise performed a Western blot, ELISA, immunoprecipitation, radioimmunoassay, or immunohistochemical assay. In some aspects, assaying may comprise mass spectrometry. In some aspects, the presence of (iii) an Arg residue at amino acid position 497 of EGFR may be determined by mass spectrometry or by sequencing a nucleic acid comprising at least a portion of the protein coding sequence of the EGFR protein.

In one embodiment, a method is provided for characterizing a cancer patient comprising selectively testing a cancer cell having been isolated from the patient to determine the methylation status of amino acids Arg198 and/or Arg200 of EGFR protein in the cancer cell. In some aspects, the method may further comprise obtaining a sample of the cancer or a circulating tumor cell from the cancer patient. In some aspects, a positive determination for methylation of amino acid Arg198 and/or Arg200 of EGFR protein may indicate that the cancer patient will be resistant to cetuximab. In some aspects, the method may further comprise identifying the cancer patient as being eligible for treating with cetuximab in combination with a PRMT inhibitor. In some further aspects, the method may further comprise administering an effective amount of cetuximab in combination with a PRMT inhibitor to the patient.

In certain aspects, the presence of (i) methylated Arg at position 198 and/or (ii) methylated Arg at position 200 of EGFR protein may be detected by mass spectrometry, ELISA, flow cytometry, immunohistochemistry, western blot, radioimmunoassay, or immunoprecipitation. In certain aspects, the presence of (i) methylated Arg at position 198 and/or (ii) methylated Arg at position 200 of EGFR protein may be detecting by a method comprising contacting the sample with an antibody that binds specifically to EGFR methylated at Arg198 and/or Arg200. As a control, the overall level of EGFR may be determined by a method comprising contacting the sample with an antibody that binds to EGFR regardless of the presence or absence of any post-translational modifications.

In one embodiment, a method is provided for selecting a drug therapy for a cancer patient comprising assaying a cancer sample isolated from the patient to determine a methylation status of Arg198 and/or Arg200 of EGFR protein in the sample. In some aspects, the method may further comprise selecting a combination of cetuximab and a PRMT inhibitor if Arg198 and/or Arg200 of EGFR protein is determined to be methylated. In some aspects, the methylation status of Arg198 and/or Arg200 of EGFR protein may be determined by mass spectrometry, ELISA, flow cytometry, immunohistochemistry, western blot, radioimmunoassay, or immunoprecipitation. In some aspects, the methylation status of Arg198 and/or Arg200 of EGFR protein may be determined by a method comprising contacting the sample with an antibody that binds specifically to EGFR methylated at Arg198 and/or Arg200. As a control, the overall level of EGFR may be determined by a method comprising contacting the sample with an antibody that binds to EGFR regardless of the presence or absence of any post-translational modifications.

In one embodiment, a method is provided for sensitizing a cetuximab-resistant cancer to cetuximab comprising administering an effective amount of a PRMT inhibitor to a patient having the cetuximab-resistant cancer. In certain aspects, the method may further comprise administering cetuximab to the patient. In some aspects, the cetuximab may be administered essentially simultaneously with the PRMT inhibitor.

In some aspects of the various embodiments, the patient may be a human. In certain aspects of the various embodiments, the cancer may be a colorectal, breast, prostate, lung, or pancreatic cancer. In various aspects of the present embodiments, methods of treating may further comprises administering a second (or a third in embodiments comprising coadministration) anticancer therapy, such as, for example, surgical therapy, chemotherapy, radiation therapy, cryotherapy, hormonal therapy, toxin therapy, immunotherapy, or cytokine therapy. In some aspects, the patient may have previously undergone at least one round of anticancer therapy.

In one embodiment, a composition is provided comprising an antibody that specifically binds to Arg198- and/or Arg200-methylated EGFR protein. In some aspects, the antibody may be an IgG1 antibody.

In one embodiment, a composition is provided comprising a polypeptide comprising at least eight consecutive amino acids of EGFR protein fused to an immunogen, wherein the at least eight consecutive amino acids of EGFR1 protein includes Arg198 and/or Arg200 and wherein Arg198 and/or Arg200 is dimethylated. In certain aspects, the polypeptide may comprise the sequence QCSGRCRGKSPSDC (SEQ ID NO: 1). In some aspects, one or both of the Arg residues may be methylated.

In one embodiment, a composition is provided comprising cetuximab and a PRMT inhibitor (e.g., sinefungin, S-adenosylhomocysteine, AMI-1, AMI-408, MDL 28,842, methylthioadenosine, C21, Eosin Y, disodium trihydrate, Cpd4, or adenosine dialdehyde) for use in the treatment of a tumor in a subject. In some aspects, the composition may be formulated for intratumoral, intravenous, intradermal, intraarterial, intraperitoneal, intralesional, intracranial, intraarticularly, intraprostatic, intrapleural, intratracheal, intraocular, intranasal, intravitreal, intravaginal, intrarectal, intramuscular, subcutaneous, subconjunctival, intravesicularl, mucosal, intrapericardial, intraumbilical, oral administration. In some aspects, the composition may further comprise at least a third anticancer therapy, such as, for example, chemotherapy, radiation therapy, hormone therapy, immunotherapy or cytokine therapy. In some aspects, the patient may have been determined to have a cancer cell comprising at least one of (i) methylated Arg at position 198, (ii) methylated Arg at position 200, and/or (iii) an Arg residue at amino acid position 497 of epidermal growth factor receptor (EGFR) protein.

In one embodiment, the use of cetuximab and a PRMT inhibitor in the manufacture of a medicament for the treatment of a tumor is provided.

In one embodiment, a method is provided for predicting resistance to cetuximab in a cancer patient comprising (a) obtaining a sample of the patient's cancer; (b) determining the methylation status of R198 or R200 of the epidermal growth factor receptor (EGFR) protein in the sample; and (c) predicting that the patient's cancer is resistant to cetuximab if R198 or R200 of EGFR is determined to be methylated. In one aspect, the method may further comprise treating the patient with cetuximab in combination with a PRMT inhibitor if the patient's cancer is predicted to be resistant to cetuximab.

In another embodiment, a method is provided of treating a cancer is a patient in need thereof comprising (a) obtaining a sample of the cancer; (b) determining the methylation status of R198 or R200 of the epidermal growth factor receptor (EGFR) protein expressed in the cancer; and (c) treating the patient with cetuximab alone if R198 and R200 of EGFR are determined to be unmethylated or treating the patient with cetuximab and a PRMT inhibitor if R198 or R200 of EGFR is determined to be methylated.

In some aspects, the methods of the present embodiments may further comprise determining the methylation status of both R198 and R200.

In one embodiment, a method is provided of treating a cancer in a patient in need thereof comprising (a) obtaining a sample of the cancer: (b) determining the amino acid present at position 497 of the EGFR protein expressed in the cancer; and (c) treating the patient with cetuximab alone if a lysine is present at position 497 of EGFR or treating the patient with cetuximab and a PRMT inhibitor if an arginine is present at position 497 of EGFR. In one aspect, the method may further comprise determining the methylation status of an arginine present at position 497 of EGFR.

In some aspects, a methylation status may be determined by mass spectrometry, immunohistochemistry, western blotting, or ELISA. Antibody-dependent methods may use either monoclonal or polyclonal antibodies specific for the methylation status of a particular amino acid to be determined. In some aspects, the amino acid present at position 497 of the EGFR protein may be determined by mass spectrometry or sequencing a nucleic acid comprising at least a portion of the protein coding sequence of the EGFR gene.

In some aspects, a cancer may be metastatic, recurrent, or multi-drug resistant. In some aspects, the patient may be treated at least a second time. In some aspects, the patient may be treated over a period of 1 week to 6 months.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Cell proliferation assay of SKCO1 (left) and GEO (right) cells exogenously expressing PRMT1, PRMT1 shRNA, and control vector. In the top graphs, the top lines represent PRMT1 and the bottom lines represent Vector. In the bottom graphs, the top lines represent Vector and the bottom lines represent PRMT1 shRNA. P<0.05, t-test. FIG. 1B. Soft agar assay of SKCO1 cells exogenously expressing PRMT1, PRMT1 shRNA and control vector. Representative images from the anchorage-independent growth assay are shown above. *P<0.05, P<0.005, t-test. FIG. 1C. Cell proliferation assay of SKCO1 (top) and GEO (bottom) cells expressing PRMT1 or vector control with or without gefitinib treatment. In both graphs, the top solid lines represent PRMT1 and the bottom solid lines represent Vector. In the top graph, the top dashed line represents PRMT1+gefitinib and the bottom dashed line represents Vector+gefitinib. P<0.05, t-test. FIG. 1D. Soft agar assay of SKCO1 exogenously expressing PRMT1 and control vector with or without gefitinib treatment. P<0.005, t-test. FIG. 1E. Immunoblots comparing pEGFR, pERK, and pAKT levels upon EGF stimulation for the indicated time in SKCO1 (left) and GEO (right) cells expressing PRMT1 or control vector. FIG. 1F. Immunoblots evaluating pEGFR, pERK, and pAKT levels upon EGF stimulation for the indicated time in SKCO1 cells expressing two different PRMT1 shRNAs or control vector. All quantitative data were generated from a minimum of three replicates. Data are expressed as mean±s.d.

FIGS. 2A-H. PRMT1 interacts with EGFR and methylates the EGFR extracellular domain at Arg198 and Arg200. FIG. 2A. Top: Reciprocal coimmunoprecipitation of SKCO1 cells using the indicated antibodies. Bottom: Duolink® assay of SKCO1 cells expressing control vector or PRMT1 shRNA. Red spots represent the interaction between PRMT1 and EGFR. FIG. 2B. Illustration of EGFR extracellular and intracellular domains that were individually subcloned with GST tags and were purified for in vitro methylation assays. FIG. 2C. In vitro methylation assays showing methylation signals from each GST-tagged EGFR domain after incubation with purified GST-tagged PRMT1.

Methylation signals were examined by fluorography. FIG. 2D. Sequence alignment of PRMT1 substrates along with EGFR showing a potential GAR motif on EGFR extracellular domain 2. FIG. 2E. In vitro methylation assay of wild-type EGFR and methylation-site mutant. FIG. 2F. Mass spectrum analysis of endogenous EGFR immunopurified from SKCO1 cells. FIG. 2G. Dot blot showing specificity of EGFR me-R198/200 Ab. H3R4: Histone H4 arginine 3 asymmetric dimethylated peptide. Asymdi: EGFR asymmetric dimethylated R198/200 peptide. Symdi: EGFR symmetric dimethylated R198/200 peptide. Mono: EGFR monomethylated R198/200 peptide. FIG. 2H. Immunoblots comparing the EGFR methylation level of SKCO1 exogenously expressing PRMT1 (left), PRMT1 shRNA (right), and control vector by EGFR methylation antibody. Methylated peptide competition showed antibody specificity for EGFR methylation signal.

FIG. 3A. Immunoblot comparing EGFR and downstream ERK activation level of GEO cells expressing control vector, wild-type, and methylation-site mutant (R198/200K) EGFR upon EGF stimulation. FIG. 3B. Cell proliferation (left) and anchorage-independent assay (right) of GEO cells expressing control vector, wild-type, and methylation-site mutant EGFR. In the graph of the cell proliferation assay, at the 4-day time point, the top line represents EGFR (wt), the middle line represents Vector, and the bottom line represents EGFR (R198/200K). Representative images of colonies are shown above the quantitative chart. *P<0.05, t-test. FIG. 3C. Dimerization assay of SKCO1 cells exogenously expressing vector control, PRMT1 (left), PRMT1 shRNA (middle), or GEO cells expressing wild-type and methylation-site mutant EGFR (right). FIG. 3D. In vivo orthotopic colon tumor growth of GEO cells expressing vector control, wild-type, and methylation sites mutant EGFR (n=5 per group, *P<0.05, t-test). Top: Representative tumors from each group in the fourth week after inoculation. FIG. 3E. Kaplan-Meier plot of overall survival of 215 colorectal cancer cases with low or high methyl-EGFR level detected by me-R198/200 Ab. Low methylation level: methylation level lower than median; High: methylation level higher than median. P<0.05. FIG. 3F. Kaplan-Meier plot of recurrence rate of 120 colorectal cancer cases with low or high methyl-EGFR level detected by me-R198/200 Ab. P<0.05. All quantitative data were generated from a minimum of three replicates. Data are expressed as mean±s.d.

FIG. 4A. Top: immunoblot showing expression level of PRMT1. Bottom: cell proliferation assay of GEO cells expressing control vector, PRMT1 or PRMT1 shRNA under cetuximab treatment (n=5). Data are expressed as mean±s.d. *P<0.05, t-test. FIG. 4B. Flow cytometric analysis of GEO cells expressing wild-type (top) or methylation-site mutant (middle) EGFR showing binding affinity between APC-conjugated EGF and EGFR in the presence or absence of cetuximab. Bottom: Quantitative results are shown in the bar graph. FIG. 4C. Top: immunoblot showing expression level of PRMT1. Bottom: cell proliferation assay of SW48 cells expressing control vector, PRMT1, or PRMT1 shRNA under cetuximab treatment (n=5). Data are expressed as mean±s.d. *P<0.05, t-test. FIG. 4D. Flow cytometry analysis of SW48 cells expressing control vector or PRMT1 showing binding affinity between APC-conjugated EGF and EGFR in the presence or absence of cetuximab. Bottom: Quantitative results are shown in the bar graph. FIG. 4E. Left: Inactive 'tethered' conformation of EGFR. The structure was prepared based on the crystal structure of the inactive human EGFR (PDB accession 1IVO). Domains I-IV are differentially shaded. Arginines 198 and 200 are highlighted. Right: Active dimerized form of EGFR (based on the crystal structure of human EGFR, PDB accession 1NQL). The second EGFR and EGF molecules are shown in gray and black, respectively. FIGS. 4F-G. Zoom onto Arg198 (FIG. 4F) and Arg200 (FIG. 4G), shown as stick figures. Domains I and II are indicated on the surfaces, as is the location of Asp206. FIG. 4H. Immunoblot assessing EGFR, ERK, and AKT activation levels of SW48 cells expressing control vector or PRMT1 upon EGF stimulation in the presence or absence of cetuximab.

FIGS. 5A-B. Knock down of PRMT1 reduces the cell proliferation rate of various cancer cell lines and PRMT1-mediated cell growth is correlated with EGFR signaling. MTT assays in the presence or absence of gefitinib of breast cancer cell line, MDA-MB-231 (FIG. 5A), and pancreatic cancer cell line, MIA PaCa-2 (FIG. 5B). In both graphs, the top solid lines represent Vector and the bottom solid lines represent PRMT1 shRNA. In the bottom graph, the top dashed line represents Vector+gefitinib and the bottom dashed line represents PRMT1 shRNA+gefitinib.

FIG. 7A. Immunoblots of the indicated proteins after cell fractionation of SKCO1 cells. FIG. 7B. Immunoblots of the indicated proteins after ER isolation of SKCO1 cells expressing control vector or PRMT1 shRNA.

FIG. 9A. Scatchard plot and binding curves (insert) measuring EGFR-EGF binding affinity of HT29 cells expressing WT or R198/200K mutant EGFR with or without cetuximab treatment. FIG. 9B. Scatchard plot and binding curves (insert) measuring EGFR-EGF binding affinity of HT29 cells expressing WT or R198/200K mutant EGFR with or without knock down of PRMT1. FIG. 9C. Scatchard plot and binding curves (insert) measuring EGFR-EGF binding affinity of SW48 cells expressing WT or R198/200K mutant EGFR with or without knock down of PRMT1.

FIGS. 10A-B. EGFR methylation does not affect its cell surface expression level. Biotinylated cell surface EGFR from SKCO1 (FIG. 10A) and GEO (FIG. 10B) cells were captured on streptavidin-agarose beads and detected by immunoblot.

DESCRIPTION OF ILLUSTRATIVE EMBODIMENTS

Figure 1A:
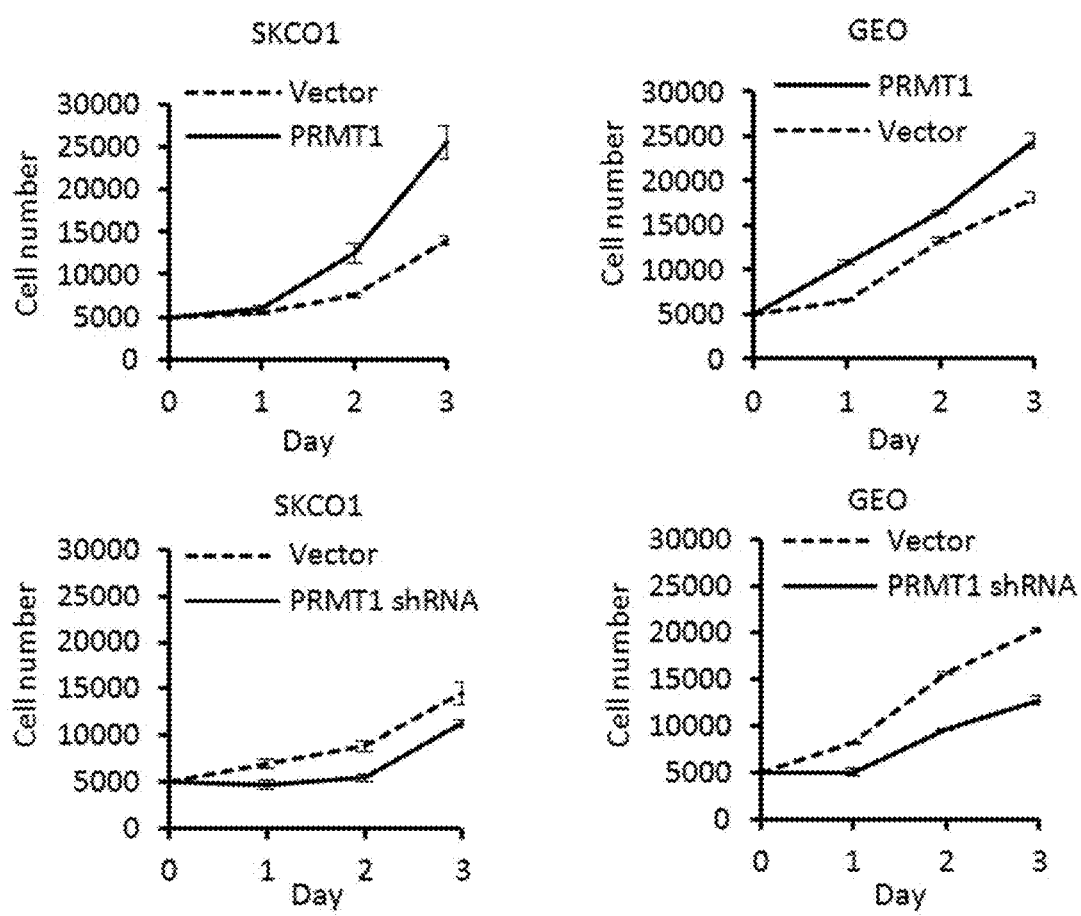
FIGS. 1A-F. PRMT1-mediated cell proliferation and colony formation are EGFR signaling dependent.

This invention provides methods for the identification of subsets of patients who are likely to be either sensitive or resistant to cetuximab therapy. For example, this invention provides biomarkers (e.g., methylation of R198 or R200 of EGFR or the presence of an arginine at position 497 of EGFR) for the prediction of resistance to cetuximab therapy. This invention also provides methods for the selection of patients for combination therapy with cetuximab and PRMT inhibitors. Patients who have arginine methylation on the extracellular domain of EGFR, specifically on residues R198 and R200, or have an arginine at position 497 are likely to be resistant to cetuximab therapy; thus, this invention will help in determining the treatment strategy for this subset of patients. Additionally, for those patients who do have the arginine methylations on EGFR, the present invention provides a combination therapy of cetuximab plus a PRMT inhibitor. The ability to predict patients' response prior to treatment, will allow for a rational treatment strategy either for use of cetuximab alone in the subset of patients without EGFR arginine methylation or use of combination therapy in the patients with EGFR arginine methylation to overcome resistance to cetuximab.

Without being bound by theory, the inventors provide a mechanism contributing to cetuximab resistance in which protein arginine methyltransferase 1 (PRMT1) methylates the extracellular domain of EGFR at R198 and R200, leading to an increase in the binding affinity between EGF and methylated EGFR, and subsequently receptor dimerization, downstream signaling activation, and cell proliferation in vitro. Meanwhile, R/K mutation of the EGFR methylation sites reduces tumor growth in mouse orthotopic xenograft model. Moreover, EGFR methylation level is correlated with poor patient outcomes. Importantly, methylated EGFR retains its signaling activation and cell proliferation in the presence of cetuximab, suggesting that the methylation status of EGFR has the potential to predict resistance to cetuximab treatment in cancer patients.

I. ANTIBODIES

It will be understood that polyclonal or monoclonal antibodies specific for R198/200 methylated EGFR will have utility in several applications. These include the production of diagnostic kits for use in detecting and diagnosing cancer as well as selecting patients for treatment.

1. Polyclonal Antibodies

Polyclonal antibodies generally are raised in animals by multiple subcutaneous or intraperitoneal injections of antigen and adjuvant. Animals are immunized against the immunogenic composition or derivatives. Animals are boosted until the titer plateaus. The animals are usually bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

2. Monoclonal Antibodies

The methods for generating monoclonal antibodies (mAbs) generally begin along the same lines as those for preparing polyclonal antibodies. Rodents, such as mice and rats, are preferring animals; however, the use of rabbit, sheep, goat, and monkey cells also is possible. The use of rats may provide certain advantages (Goding, 1986), but mice are preferred, with the BALB/c mouse being most preferred as this is most routinely used and generally gives a higher percentage of stable fusions.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

The animals are injected with antigen, generally as described above for polyclonal antibodies. The antigen may be coupled to carrier molecules, such as keyhole limpet hemocyanin, if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the mAb generating protocol. These cells may be obtained from biopsied spleens or lymph nodes. Spleen cells and lymph node cells are preferred, the former because they are a rich source of antibody producing cells that are in the dividing plasmablast stage.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma-producing fusion procedures preferably are non-antibody producing, have high fusion efficiency, and have enzyme deficiencies that render them incapable of growing in certain selective media that support the growth of only the desired fused cells (hybridomas).

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Köhler and Milstein (1976), and those using polyethylene glycol (PEG), such as 37% (v/v) PEG. The use of electrically induced fusion methods also is appropriate (Goding, 1986).

Fusion procedures usually produce viable hybrids at low frequencies, about $1 \times 10^6$ to $1 \times 10^8$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single clone dilution in microtiter plates, followed by testing the individual clonal supernatants (after about two to three weeks) for the desired reactivity. The assay should be sensitive, simple, and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide mAbs. The cell lines may be exploited for mAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils, such as pristane (tetramethylpentadecane), prior to injection. The injected animal develops tumors secreting the specific monoclonal antibody produced by the fused cell hybrid. The body fluids of the animal, such as serum or ascites fluid, can then be tapped to provide mAbs in high concentration.

The individual cell lines could also be cultured in vitro, where the mAbs are naturally secreted into the culture medium from which they can be readily obtained in high concentrations.

mAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods that include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells, e.g., normal versus tumor cells. The advantages of this approach over conventional hybridoma techniques are that approximately $10^4$ times as many antibodies can be produced and screened in a single round, and that new specificities are generated by H and L chain combination, which further increases the chance of finding appropriate antibodies.

II. BIOMARKER DETECTION

In certain embodiments, the method comprises the steps of obtaining a biological sample from a mammal to be tested and detecting the presence of Arg198/200 EGFR methylation or the presence of an arginine at amino acid position 497 of EGFR in the sample. The EGFR gene is alternative spliced resulting in the production of four protein isoforms. All four precursor isoforms (see SEQ ID NOs: 12, 14, 16, and 18) comprise a 24 amino acid signal peptide that is cleaved to produce the mature protein. The numbering system used herein (i.e., regarding positions 198, 200, and 497) refers to the mature protein sequence (see SEQ ID NOs: 13, 15, 17, and 19). Note that the mature isoform C (SEQ ID NO: 17) does not comprise a position 497, but does comprise Arg198 and Arg200.

In one embodiment, the biological sample is a cell sample from a tumor in the mammal. In another embodiment, the biological sample is a circulating tumor cell isolated from the mammal. As used herein the phrase "selectively measuring" refers to methods wherein only a finite number of protein or nucleic acid (e.g., mRNA) markers are measured rather than assaying essentially all proteins or nucleic acids in a sample. For example, in some aspects "selectively measuring" nucleic acid or protein markers can refer to measuring no more than 100, 75, 50, 25, 15, 10, 5, or 2 different nucleic acid or protein markers.

The assays can identify a biomarker for predicting therapy response to a therapeutic regimen, such as anti-EGFR therapy. Assays for response prediction may be run before start of therapy and patients showing levels of a biomarker above or below a threshold level of the biomarker are eligible to receive anti-EGFR therapy.

A. Biological Samples

The sample obtained from an individual may contain cells affected by the disease, meaning that the cells express the disease-associated protein. Thus, where the protein is expressed in a cell-specific manner, the sample will contain the cell type in which the disease protein is expressed. In terms of antigen detection, the sample analyzed may be any body fluid sample that is suspected of containing the antigen, such as, for example, blood serum, cerebrospinal fluid, mucus, saliva, vaginal secretion, and urine, or may be a sample of the diseased tissue itself.

1. Tumor Cell Sample

The method includes collecting samples from a cancer patient for assessment of biomarker levels. The method can use a patient tissue sample of any type or a derivative thereof, including peripheral blood, serum or plasma fraction from peripheral blood, tumor or suspected tumor tissues (including fresh frozen and fixed or paraffin embedded tissue), cell isolates such as circulating epithelial cells separated or identified in a blood sample, lymph node tissue, bone marrow and fine needle aspirates. The sample suitable for use in the method can comprise any tissue type or cell isolates from any tissue type, including a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a serum or plasma fraction of a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample. For example, a patient peripheral blood sample can be initially processed to extract an epithelial cell population, a plasma fraction or a serum fraction, and this extract, plasma fraction or serum fraction can then be assayed. A microdissection of the tissue sample to obtain a cellular sample enriched with suspected tumor cells can also be used. The tissue sample can be processed by any desirable method for performing protein-based assays.

2. Circulating Tumor Cells

Circulating tumor cells (CTCs) from any suitable sample type may be used to detect the biomarkers of the present embodiments. As used herein, the term "sample" refers to any sample suitable for the methods provided by the present invention. The sample may be any sample that includes CTCs suitable for detection of a biomarker. Sources of samples include whole blood, serum, bone marrow, pleural fluid, peritoneal fluid, central spinal fluid, urine, saliva and bronchial washes. In one aspect, the sample is a blood sample, including, for example, whole blood or any fraction or component thereof. A blood sample, suitable for use with the present invention may be extracted from any source known that includes blood cells or components thereof, such as venous, arterial, peripheral, tissue, cord, and the like. For example, a sample may be obtained and processed using well known and routine clinical methods (e.g., procedures for drawing and processing whole blood). In one aspect, an exemplary sample may be peripheral blood drawn from a subject with cancer.

The total number of CTCs in a CTC population is dependent, in part, on the initial sample volume. In various aspects, detection of biomarkers in CTCs from a wide range of initial sample volumes is sufficient to provide clinically significant results. As such, the initial sample volume may be less than about 25 µl, 50 µl, 75 µl, 100 µl, 125 µl, 150 µl, 175 µl, 200 µl, 225 µl, 250 µl, 300 µl, 400 µl, 500 µl, 750 µl, 1 ml, 2 ml, 3 ml, 4 ml, 5 ml, 6 ml, 7 ml, 8 ml, 9 ml or greater than about 10 ml. In an exemplary aspect, the initial sample volume is between about 100 and 200 µl. In another exemplary aspect, a sample processed as described herein includes greater than about 1, 2, 5, 7, 10, 15, 20, 30, 40, 50, 100, 200, 300, 400, 500, 600, 700, 800, 900, or even 1000 CTCs.

As used herein, biomarker detection analysis includes any method that allows direct or indirect isolation of CTCs and may be in vivo or ex vivo. For example, analysis may include, but not limited to, ex vivo microscopic or cytometric detection and visualization of cells bound to a solid substrate, flow cytometry, fluorescent imaging, and the like. In an exemplary aspect, CTCs are isolated using antibodies directed to CTC-specific cell surface markers.

In another embodiment, the CTCs are captured by techniques commonly used to enrich a sample for CTCs, for example those involving immunospecific interactions, such as immunomagnetic capture Immunomagnetic capture, also known as immunomagnetic cell separation, typically involves attaching antibodies directed to proteins found on a particular cell type to small paramagnetic beads. When the antibody-coated beads are mixed with a sample, such as blood, they attach to and surround the particular cell. The sample is then placed in a strong magnetic field, causing the beads to pellet to one side. After removing the blood, captured cells are retained with the beads. Many variations of this general method are well known in the art and suitable for use to isolate CTCs.

Isolation of CTCs and characterization of biomarkers therein, using the methods of the invention, is useful in assessing cancer prognosis and in monitoring therapeutic efficacy for early detection of treatment failure that may lead to disease relapse. This is because the presence of CTCs has been associated and/or correlated with tumor progression and spread, poor response to therapy, relapse of disease, and/or decreased survival over a period of time. Thus, enumeration of CTCs and characterization of biomarkers therein provide methods to stratify patients for baseline characteristics that predict initial risk and subsequent risk based upon response to therapy.

Accordingly, in another embodiment, the invention provides a method for diagnosing or prognosing cancer in a subject. CTCs isolated according to the methods disclosed herein may be analyzed to diagnose or prognose cancer in the subject. As such, the methods of the present invention may be used, for example, to evaluate cancer patients and those at risk for cancer. In any of the methods of diagnosis or prognosis described herein, either the presence or the absence of one or more indicators of cancer, such as a R198/200 EGFR methylation event, may be used to generate a diagnosis or prognosis.

In one aspect, a blood sample is drawn from the patient and CTCs are analyzed as described herein. Using the method of the invention, the number of CTCs in the blood sample may be determined and the CTCs subsequently analyzed. For example, the cells may be labeled with one or more antibodies that bind to a CTC-specific cell surface marker, such as, for example, cytokeratin or EpCAM, and the antibodies may have a covalently bound fluorescent label. Analysis may then be performed to characterize the CTCs in the sample, and from this measurement.

B. Detection Methods

In one embodiment, the methods described herein provide for detecting the presence a posttranslational modification of a protein (e.g., R198, R200, and/or R497 methylation of EGFR) or a sequence alteration of a gene (e.g., the presence of an arginine at amino acid position 497 of EGFR) in a biological sample obtained from an individual.

In some embodiment of the methods described herein, detecting the presence a biomarker in a biological sample obtained from an individual comprises determining the presence of a modified polypeptide in the sample. A polypeptide can be detected by any of a number of means known to those of skill in the art, including analytical biochemical methods, such as electrophoresis, capillary electrophoresis, high performance liquid chromatography ("HPLC"), thin layer chromatography ("TLC"), hyperdiffusion chromatography, and the like, or various immunological methods, such as fluid or gel precipitation reactions, immunodiffusion (single or double), immunoelectrophoresis, radioimmunoassay ("RIA"), enzyme-linked immunosorbent assay ("ELISA"), immunofluorescent assays, flow cytometry, FACS, western blotting, and the like.

Techniques for detecting arginine 497 in EGFR in a sample include reverse transcription of mRNA, followed by PCR amplification with primers specific for EGFR mRNA (e.g., RT-PCR or quantitative RT-PCR), and finally sequencing of the amplification product. Alternatively, the mRNA may be sequenced directly without the need for amplification.

1. Immunological Methods

The presence of a modified polypeptide can be determined by contacting the sample with an antibody that specifically binds to the modified polypeptide product (e.g., R198/200 methylated EGFR) and detecting or measuring the formation of the complex between the antibody and the modified polypeptide. An antibody can be labeled (e.g., radioactive, fluorescently, biotinylated or HRP-conjugated) to facilitate detection of the complex. Appropriate assay systems for detecting polypeptides include, but are not limited to, flow cytometry, enzyme-linked immunosorbent assay (ELISA), competition ELISA assays, radioimmunoassays (RIA), immunofluorescence, gel electrophoresis, western blot, chemiluminescent assays, bioluminescent assays, and immunohistochemical assays using antibodies having specificity for the modified polypeptide. Numerous methods and devices are well known to the skilled artisan for the detection and analysis of the instant invention. With regard to polypeptides or proteins in test samples, immunoassay devices and methods are often used. These devices and methods can utilize labeled molecules in various sandwich, competitive, or non-competitive assay formats, to generate a signal that is related to the presence or amount of a biomarker of interest. Additionally, certain methods and devices, such as but not limited to, biosensors and optical immunoassays, may be employed to determine the presence or amount of biomarkers without the need for a labeled molecule.

In general, immunological methods include obtaining a sample suspected of containing an antigen, contacting the sample with a first monoclonal antibody that binds the antigen, and contacting the sample with a composition capable of selectively binding or detecting the complex, e.g., a labeled second antibody, under conditions effective to allow immune complex (antigen/antibody) formation. Examples of compositions capable of selectively binding or detecting the antigen include, but are not limited to, antibodies, aptamers, or other ligands that can be labeled using a variety of markers, e.g., biotin/avidin ligand binding arrangement, as is known in the art. One skilled in the art may also use a labeled third antibody.

"Under conditions effective to allow immune complex (antigen/antibody) formation" means that the conditions preferably include diluting the antigens and/or antibodies with solutions such as BSA, bovine gamma globulin (BGG), or phosphate buffered saline (PBS)/Tween. These agents tend to assist in the reduction of nonspecific background. The "suitable" conditions also means that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Contacting the patient sample with the first antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present, i.e., methylated EGFR. After this time, the sample-antibody composition, such as an ELISA plate, dot blot, or western blot, will generally be washed to remove any non-specifically bound antibody species, allowing only those antibodies specifically bound with the antigen to be detected.

The antigen, antibody, or antigen:antibody complex employed in the detection may itself be linked to a detectable label, wherein one would then simply detect this label, thereby allowing the amount of the antigen in the sample to be determined. Alternatively, the first antibody that becomes bound within the antigen may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of a primary immune complex by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Immunohistochemical staining may be used to detect the presence of a biomarker. This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the biomarker.

An enzyme-linked immunosorbent assay, or ELISA, may be used to measure the expression of a plurality of biomarkers. There are many variations of an ELISA assay. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

The western blot is a method of assaying for the presence of a particular protein within a biological sample. The general methodology of the western blot is comprised of applying the sample to a polyacrylamide gel and separating the proteins through the technique of gel electrophoresis. The proteins, which have been separated into discrete bands, are subsequently transferred to a sheet (e.g., nitrocellulose or PVDF) by way of a blotting chamber. Once the protein bands have been transferred, the blot is treated with antibody specific to the particular antigen of interest; if the antigen is present, the antibody will bind to the antigen. Free antibody is washed away, the blot is treated with a second antibody which is capable of binding to a site on the first antibody, and the blot is rinsed again to remove excess antibody. In order to detect binding, the second antibody may carry a radiolabel or fluorescent label or may be linked to an enzyme as in the ELISA technique. The enzyme linked to the antibody may then in turn react with a substrate applied to the blot which, for example, generates a colored product. In the case of a radiolabel, the bands may be visualized through the technique of autoradiography, where the radioactive blot is exposed to photographic film for a time sufficient to visualize the protein band or bands of interest. In the case of a fluorescent label, the bands may be visualized using an Odyssey imaging system (LI-COR). The presence of very small quantities of antigen may be detected due to the highly sensitive nature of the western blotting technique.

An antibody microarray may also be used to measure the differential expression of a plurality of biomarkers. For this, a plurality of antibodies is arrayed and covalently attached to the surface of the microarray or biochip. A protein extract containing the biomarker proteins of interest is generally labeled with a fluorescent dye. The labeled biomarker proteins are incubated with the antibody microarray. After washes to remove the unbound proteins, the microarray is scanned. The raw fluorescent intensity data may be converted into expression values using means known in the art.

As detailed above, immunoassays, in their most simple and/or direct sense, are binding assays. Certain preferred immunoassays are the various types of enzyme-linked immunosorbent assays (ELISAs) and/or radioimmunoassays (RIA) known in the art. Immunohistochemical detection using tissue sections is also particularly useful. However, it will be readily appreciated that detection is not limited to such techniques, and western blotting, dot blotting, FACS analyses, and/or the like may also be used.

2. Analytical Biochemical Methods

Alternatively, the presence of methylated EGFR polypeptide may be detected using analytical biochemical methods, such as, for example, techniques including gel electrophoresis, isoelectric focusing (IEF), cation exchange HPLC, or mass spectrometry. Mass spectrometric analysis has been used for the detection of proteins in serum samples. Mass spectroscopy methods include Surface Enhanced Laser Desorption Ionization (SELDI) mass spectrometry (MS), SELDI time-of-flight mass spectrometry (TOF-MS), Maldi Qq TOF, MS/MS, TOF-TOF, ESI-Q-TOF and ION-TRAP.

In one embodiment of the method, mass spectrometry methods are used to identify proteolytic disease peptides derived from mutant or modified disease proteins. Such methods are efficient, accurate methods to isolate and identify biomolecules and are well suited to separation and identification of proteolytic disease peptides having a disease mutation that may differ by a single amino acid or that may differ with respect to post-translational modifications as compared to a proteolytic non-disease peptide which may be contained in the same sample of a heterozygous individual.

Thus, techniques such as MALDI-TOF mass spectrometry, LC/MS/MS (MRM) or high resolution LC/MS may be used. Preparation of the sample fraction containing the proteolytic peptides may be done in accordance with routine methods. For example, the fraction of the sample containing the proteolytic peptides may be mixed with a UV-absorbing matrix prior to laser irradiation in a mass spectrometer or injected for LC/MS.

Techniques such as tandem mass spectroscopy (MS/MS) and liquid chromatography/mass spectroscopy (LC/MS and LC/MS/MS) can be used to obtain the sequence of individual peptides in the sample. Briefly, in LC/MS, different peptides are separated by a reverse phase column according to their hydrophobicity and sprayed into a mass spectrometer for mass measurement. In LC/MS/MS, the peptide is further fragmented in the mass spectrometer to generate fragments, and one, a few, or all of the fragments can be measured in the mass spectrometer to increase specificity.

Thus, for example, the use of selected reaction monitoring (SRM) mode and multiple reaction monitoring mode (MRM) can be performed using tandem MS methods in order to identify the sequences of the particular peptides contained within the sample.

As indicated above, mass spectroscopy methods can also be used to identify differences in post-translational modification between proteolytic peptides containing a disease mutation and non-disease peptides.

If desired, the results obtained with the sample from the individual to be diagnosed may be compared with samples containing known non-disease proteolytic peptides without any mutation/modification and/or with samples containing known disease proteolytic peptides containing known disease mutations/modifications.

III. TREATMENT OF NEOPLASTIC CONDITIONS

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an EGFR-targeted therapeutic (e.g., EGFR-targeted monoclonal antibody) either alone or in combination with a PRMT inhibitor.

The term "therapeutic benefit" or "therapeutically effective" as used throughout this application refers to anything that promotes or enhances the well-being of the subject with respect to the medical treatment of the condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

The term "subject," as used herein, refers to any individual or patient to which the subject methods are performed. Generally the subject is human, although as will be appreciated by those skilled in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "cancer," as used herein, includes a variety of cancer types that are well known in the art, including but not limited to, dysplasias, hyperplasias, solid tumors and hematopoietic cancers. Many types of cancers are known to metastasize and shed circulating tumor cells or be metastatic, for example, a secondary cancer resulting from a primary cancer that has metastasized. Tumors for which the present treatment methods are useful include any malignant cell type, such as those found in a solid tumor or a hematological tumor. Exemplary solid tumors can include, but are not limited to, a tumor of an organ or organ system selected from the group consisting of cardiac, genitourinary tract, reproductive, liver, bone, nervous system, skin, pancreas, colon, cecum, stomach, adrenal gland, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, vascular cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; moles dysplastic nevi; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; lipoma; angioma; dermatofibroma; keloids; mammary cancer; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; osteoblastic osteocarcinoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; uterine leiomyomas; pinealoma, malignant; chordoma; choroid plexus carcinoma; glioma, malignant; Schwannoma; medulloblastoma; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

An effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Treatment outcomes can be predicted and monitored and/or patients benefiting from such treatments can be identified or selected via the methods described herein.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, the patient's clinical history and response to the agent, and the discretion of the attending physician. The agent is suitably administered to the patient at one time or over a series of treatments.

IV. PHARMACEUTICAL PREPARATIONS

It is contemplated that pharmaceutical preparations can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with other anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, solid carriers, diluents, or excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particular requirements of individual subjects.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more EGFR-targeting antibody or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition comprising an EGFR-targeting antibody and/or optionally a PRMT inhibitor as disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

Further in accordance with certain aspects of the present invention, the composition suitable for administration may be provided in a pharmaceutically acceptable carrier with or without an inert diluent. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., fats, oils, polyol (for example, glycerol, propylene glycol, and liquid polyethylene glycol, and the like), vegetable oil, and injectable organic esters, such as ethyloleate), lipids, liposomes, dispersion media, coatings (e.g., lecithin), surfactants, antioxidants, preservatives (e.g., antibacterial or antifungal agents, anti-oxidants, chelating agents, inert gases, parabens (e.g., methylparabens, propylparabens), chlorobutanol, phenol, sorbic acid, thimerosal or combinations thereof), isotonic agents (e.g., sugars and sodium chloride), absorption delaying agents (e.g., aluminum monostearate and gelatin), salts, drugs, drug stabilizers, gels, resins, fillers, binders, excipients, disintegration agents, lubricants, sweetening agents, flavoring agents, dyes, fluid and nutrient replenishers, such like materials and combinations thereof, as would be known to one of ordinary skill in the art. The carrier should be assimilable and includes liquid, semi-solid, i.e., pastes, or solid carriers. In addition, if desired, the compositions may contain minor amounts of auxiliary substances, such as wetting or emulsifying agents, stabilizing agents, or pH buffering agents. The pH and exact concentration of the various components in a pharmaceutical composition are adjusted according to well-known parameters. The proper fluidity can be maintained, for example, by the use of a coating, such as lecithin, by the maintenance of the required particle size in the case of dispersion, and by the use of surfactants.

A pharmaceutically acceptable carrier is particularly formulated for administration to a human, although in certain embodiments it may be desirable to use a pharmaceutically acceptable carrier that is formulated for administration to a non-human animal but that would not be acceptable (e.g., due to governmental regulations) for administration to a human. Except insofar as any conventional carrier is incompatible with the active ingredient (e.g., detrimental to the recipient or to the therapeutic effectiveness of a composition contained therein), its use in the therapeutic or pharmaceutical compositions is contemplated. In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The therapeutics may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid and the like. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine and the like. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition comprising one or more lipids and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man) However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the therapeutic agent may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present invention administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

V. COMBINATION TREATMENTS

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

An anti-EGFR therapeutic may be administered before, during, after, or in various combinations relative to an anti-cancer treatment, such as a PRMT inhibitor. The administrations may be in intervals ranging from concurrently to minutes to days to weeks. In embodiments where an anti-EGFR therapeutic is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with an anti-EGFR therapeutic and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an anti-EGFR therapeutic either alone or in combination with a PRMT inhibitor is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

VI. KITS

Certain aspects of the present invention may provide kits, such as diagnostic or therapeutic kits. For example, a kit may comprise one or more pharmaceutical compositions as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of an anti-EGFR therapeutic and a PRMT inhibitor, optionally formulated as a pharmaceutical, or lyophilized, for use with a delivery device.

It also is contemplated that the above reagents maybe packaged in a kit that may be produced commercially for detecting a biomarker, e.g., a methylated EGFR polypeptide, described herein. Such a kit can be prepared from readily available materials and reagents and housed in a sealed container. For example, such a kit can comprise any one or more of the following materials: reaction tubes, buffers, detergent, antibodies, and labeled probes (e.g., labeled antibodies). In a preferred embodiment, a kit of the present invention would allow a practitioner to detect the presence of methylated EGFR in a patient sample. Instructions for performing the assays can also be included in the kit.

Kits may comprise a container with a label. Suitable containers include, for example, bottles, vials, and test tubes. The containers may be formed from a variety of materials, such as glass or plastic. The container may hold a composition that includes an anti-EGFR therapeutic and/or a PRMT inhibitor that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Constructs, Reagents, Peptides and Antibodies.

EGFR and PRMT1 constructs were prepared as described previously (Hsu et al., 2011). Four extracellular domains, juxtamembrane domain, kinase domain and C-terminal tail of EGFR were further subcloned into pGEX vector for the preparation of truncated EGFR recombinant proteins. EGFR (R198/200K) mutagenesis was generated using the Quick-Change® Site-Directed Mutagenesis Kit according to the manufacturer's protocol (Stratagene). Epidermal growth factor (EGF; Sigma) was prepared according to the manufacturers' instructions. Unmodified (Ac-QCSGRCRGK-SPSD-C; SEQ ID NO: 1), asymmetric dimethylated (Ac-QCSG(asymmetric dimethyl-R)C(asymmetric dimethyl-R) GKSPSD-C), symmetric dimethylated (Ac-QCSG (symmetric dimethyl-R)C(symmetric dimethyl-R) GKSPSD-C), and monomethylated (Ac-QCSG (monomethyl-R)C(monomethyl-R)GKSPSD-C) EGFR peptides were chemically synthesized by Lifetein for antibody production in mice and dot blot and peptide competition assays. Anti-EGFR antibody (06-847, 1:2,000; Millipore) was used to detect full-length EGFR. Antibodies against phospho-Tyr 1086 and -Tyr 1148 (Abcam) were used for detection of EGFR activation. Antibodies to ERK (1:5,000; Millipore) and phospho-ERK (1:5,000; Cell Signaling) were used to detect the EGFR downstream signaling activation. Anti-PRMT1 (Cell Signaling) was used to detect PRMT1 level after overexpression or knockdown. Anti-tubulin antibody was purchased from Sigma.

Cell Culture.

SKCO1 and SW48 were purchased form ATCC. GEO cell was a kindly gift from Dr. Zhen Fan (MD Anderson cancer center). GEO and SW48 cells were cultured in DMEM/F-12 with 10% fetal calf serum. SKCO1 cell were cultured in MEM with 10% fetal calf serum. All cell lines were characterized as *mycoplasma* negative. Before EGF stimulation, 80% confluent cells were serum-starved for 20 h, and then stimulated with 50 ng/ml EGF for indicated time.

shRNA Construct and Transfection.

Lentiviral-based pLKO.1 PRMT1 shRNA vector was obtained from Academia Sinica (Taipei, Taiwan). The pLKO.1 scrambled shRNA vector was purchased from Addgene. (Cambridge, Mass.). The PRMT1-targeting shRNA #1 sequence used in lentivirus construct was: 5'-CCGGCCGGCAGTACAAAGACTA-CAACTCGAGTTGTAGTCTTTGTACTGCCGGTTT TTG-3' (SEQ ID NO: 2). The PRMT1-targeting shRNA #2 was: 5'-CCGGGCAAGTGAAGCGGAATGAC-TACTCGAGTAGTCATTCCGCTTCACTTGCTTT TTG-3' (SEQ ID NO: 3). For lentiviral production, PLKO.1 PRMT1 shRNA vector, packaging (pCMV-dr8.Z dvpr) and envelope (pCMV-VSV-G) plasmids were co-transfected into 293T cells using Lipofectamine® Reagent (Invitrogen, Carlsbad, Calif.). After 48-hr transfection, colon cancer cell lines were infected with viral particles. Stable knockdown clones were selected by culturing cells in medium with 4 µg/ml puromycin for 1 month.

Cell Proliferation Assay.

Cells were seeded in 6-well plates (triplicate), and fresh medium (with or without gefitinib or cetuximab) were added every day. Cells were then trypsinized and cell numbers counted on a daily basis.

Anchorage-Independent Growth Assay for Colony Formation.

The base layer of cell growth matrix containing DMEM/F12 medium, 10% FBS, and 0.5% agar was paved in 6-well plates (1.5 ml per well). After solidification of the base layer, the top layer (1.5 ml per well) containing DMEM/F12 medium, 10% FBS, and 0.35% agarose and 1,000 cells was plated. Culture medium (1 ml) was added to each well and changed every 3 days. After 4-week culture, colonies were stained by 0.005% crystal violet. Colonies with a diameter larger than 0.5 mm were counted.

In Vitro Methylation Assay.

GST-tagged PRMT1 and GST-tagged EGFR fragments were expressed in $E.\ coli$ individually and purified using Glutathione Sepharose 4B. They were then incubated together in the presence of 2.2 Ci S-adenosyl-L-[methyl-$^3$H] methionine (85 Ci/mmol from a 0.55 mCi/ml stock solution; MP Biomedicals) for 1 h at 30° C. in a final volume of 50 µl of phosphate-buffered saline. After reaction, samples were separated by SDS-PAGE and transferred to PVDF membrane. Methylation levels were examined by fluorography.

Mass Spectrometry.

EGFR was isolated by immunoprecipitation with anti-EGFR antibody and then was analyzed by SDS-PAGE. The protein band corresponding to EGFR was excised and subjected to in-gel digestion with trypsin. After isolation by immobilized metal affinity chromatography, the enriched methyl-peptides were analyzed by micro-liquid chromatography/tandem MS.

In Vivo Protein Interaction by Duolink® Assay.

Cells were seeded in 8-well chamber slides. When harvesting cells, cells were washed with cold PBS twice and fixed with 4% paraformadehyde at 4° C. for 2 h. After two more PBS washes, cells were permeabilized by cold 0.2% Triton® X-100 for 30 min at room temperature and subjected to Doulink assay (Olink Bioscience) according to the manufacturers' instructions.

Dimerization Assay.

Cells were starved in serum free medium for 24 h. After starvation, cold PBS containing 50 ng/ml EGF was added onto plates for 30 min at 4° C. Then, cells were washed with cold PBS (137 mM NaCl, 0.67 mM KCl, 8 mM $Na_2HPO_4$, 1.4 mM $KH_2PO_4$) three times and incubated for 2 h at 4° C. with 5 mM cross linker $BS^3$ (bis[sulfosuccinimidyl] suberate; Thermo scientific) in PBS. After washing three times with cold PBS, cross linking reactions were stopped by incubating cells in 50 mM Tris buffer (pH 7.5) for 15 min at ambient temperature. Cells were subsequently lysed and cell lysates analyzed by Western blotting.

Clonogenic Assay.

Cells (500 cells per well, 12 wells per cell type) were seeded in 6-well plates. Culture medium was changed every three days. After 2 weeks of cell culture, cells were washed by cold PBS twice and fixed by 4% paraformadehyde for 1 h. Cells then were stained by 0.005% crystal violet at 4° C. overnight. After washed by dd$H_2O$, colonies with a diameter larger than 0.5 mm were counted.

Orthotopic Colon Cancer Mouse Model.

All animal experiments were carried out in accordance with approved protocol from Institutional Animal Care and Use Committee (IACUC) at MD Anderson Cancer Center. Nude female mice at 4-5 weeks of age were maintained at the MD Anderson Animal Facility for 1 week prior to injection of cancer cells. The cecum was exteriorized through a small midline laparotomy and $10^7$ GEO cells expressing wild-type EGFR, EGFR methylation-site mutant, or vector control were injected into the cecal wall. After injection, the abdominal wall was closed by wound clips. One month after surgery, tumors were harvested and tumor weight measured.

Immunohistochemical Staining (IHC).

IHC of methylated EGFR was performed using homemade me-R198/200 antibody. Colorectal cancer tissue microarrays were purchased from National Cancer Institute Cancer Diagnosis Program. Samples were deparaffinized and rehydrated. Antigen retrieval was done by using 0.01 M sodium-citrate buffer (pH 6.0) in a microwave oven. The sections were treated with 1% hydrogen peroxide in methanol for 30 min to block endogenous peroxidase activity. After 1 h preincubation in 10% normal serum to prevent nonspecific staining, the samples were incubated with primary antibodies at 4° C. overnight. The sections were then treated with biotinylated secondary antibody, followed by incubations with avidinbiotin peroxidase complex solution for 1 h at room temperature. Color was developed with the 3-amino-9-ethylcarbazole solution. Counterstaining was carried out using Mayer's hematoxylin. All immunostained slides were scanned on the Automated Cellular Image System III (ACIS® III) (Dako, Denmark) for quantification by digital image analysis. A total score of protein expression was calculated automatically from the percentage of immunopositive cells and immunostaining intensity.

Example 1—PRMT1 Regulates EGFR Signaling and Cetuximab Response in Colorectal Cancer Epidermal growth factor receptor (EGFR)-targeted monoclonal antibody, cetuximab, has been shown to be effective in many cancer types including colon cancer. However, resistance to cetuximab has been observed in clinical setting for colon cancer. Even-more, the outcomes from clinical trials in breast and pancreatic cancer were not satisfactory, suggesting that resistance mechanisms exist. As a result, cetuximab has not been approved for treatment of breast and pancreatic cancer. The inventors have identified arginine methylations of the extracellular domain of EGFR that induce resistance to the cetuximab. Specifically, the inventors found that protein arginine methyltransferase 1 (PRMT 1) methylates the extracellular domain of EGFR at R198 and R200 leading to an increase in the binding affinity between EGF and methylated EGFR, and subsequently receptor dimerization, downstream signaling activation, and cell proliferation in vitro. Meanwhile, R/K mutation of the EGFR methylation sites reduces tumor growth in a mouse orthotopic xenograft model. Moreover, EGFR methylation level is correlated with poor patient outcomes. Importantly, the increased EGFR methylation retains its signaling activation and cell proliferation in the presence of cetuximab, suggesting that the methylation status of EGFR has the potential to predict resistance to cetuximab treatment. Thus, the arginine methylation of EGFR R198 and R200 may serve as biomarkers to predict resistance to cetuximab therapy. In addition, the combination of cetuximab plus a PRMT inhibitor may be a therapeutic strategy able to overcome resistance to cetuximab therapy. Another EGFR arginine site (R497) was also shown to have arginine/lysine polymorphism, in which the presence of the arginine amino acid leads to resistance to cetuximab, while with the lysine amino acid it is more sensitive to cetuximab. Thus, EGFR R497 methylation is also likely to cause resistance to cetuximab and combination with a PRMT inhibitor may be a potential strategy for overcoming this resistance.

Figure 1B:
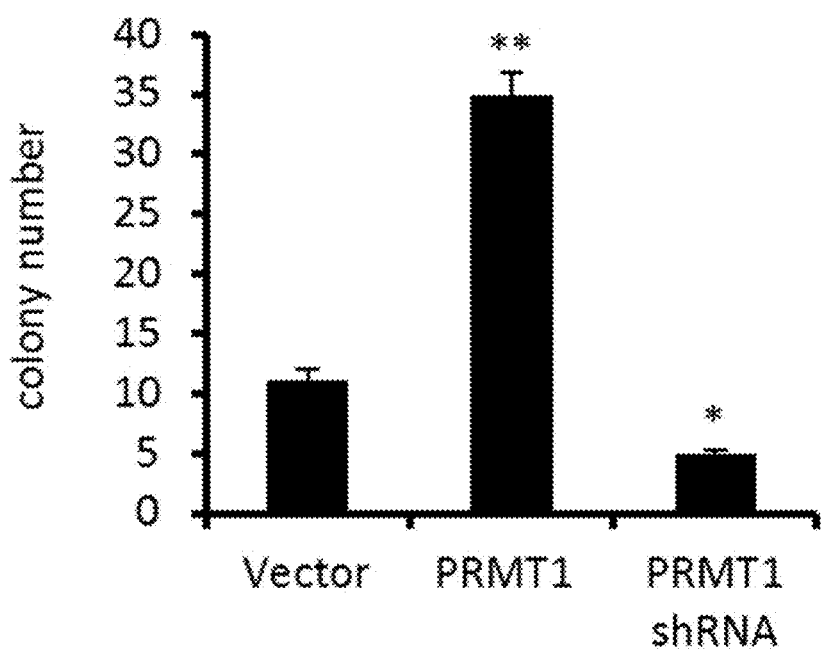
Figure 1C:
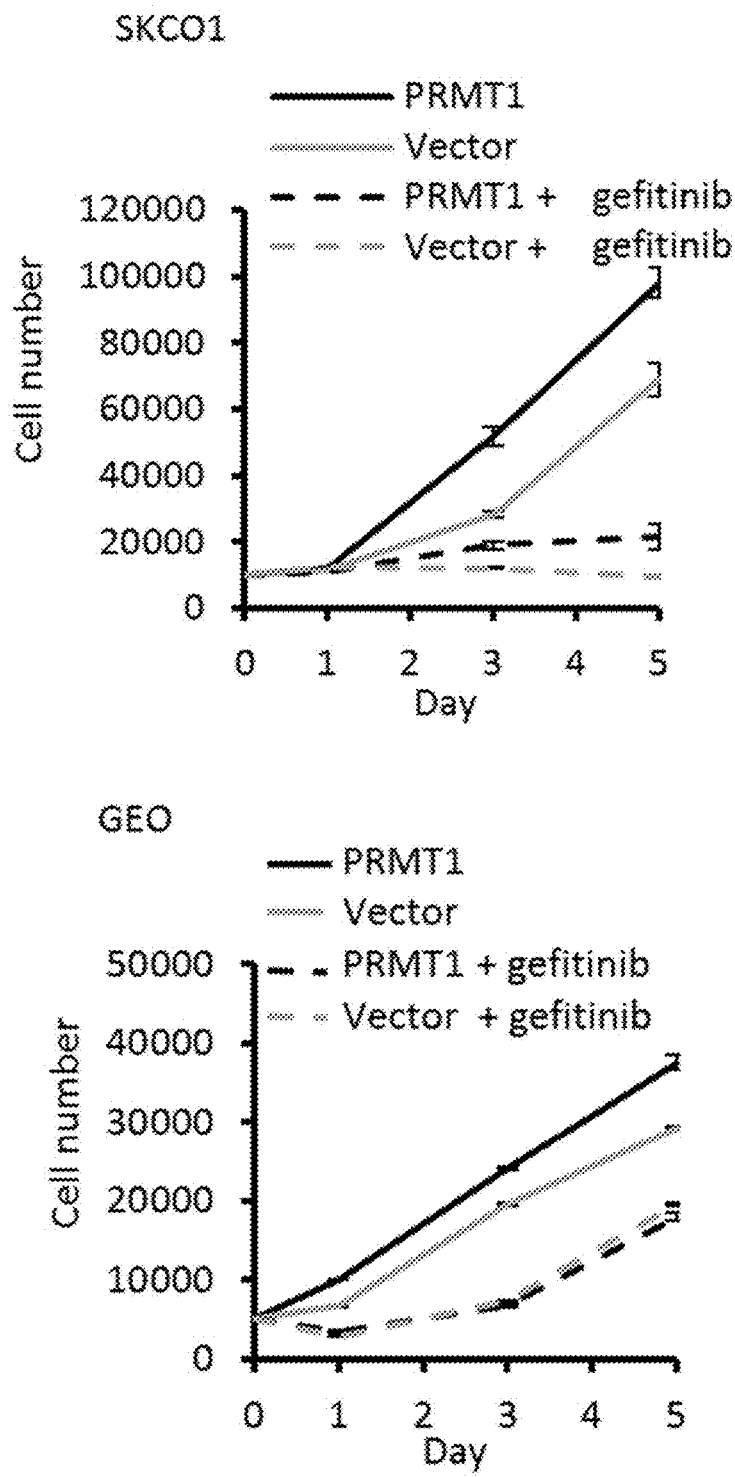
Figure 1D:
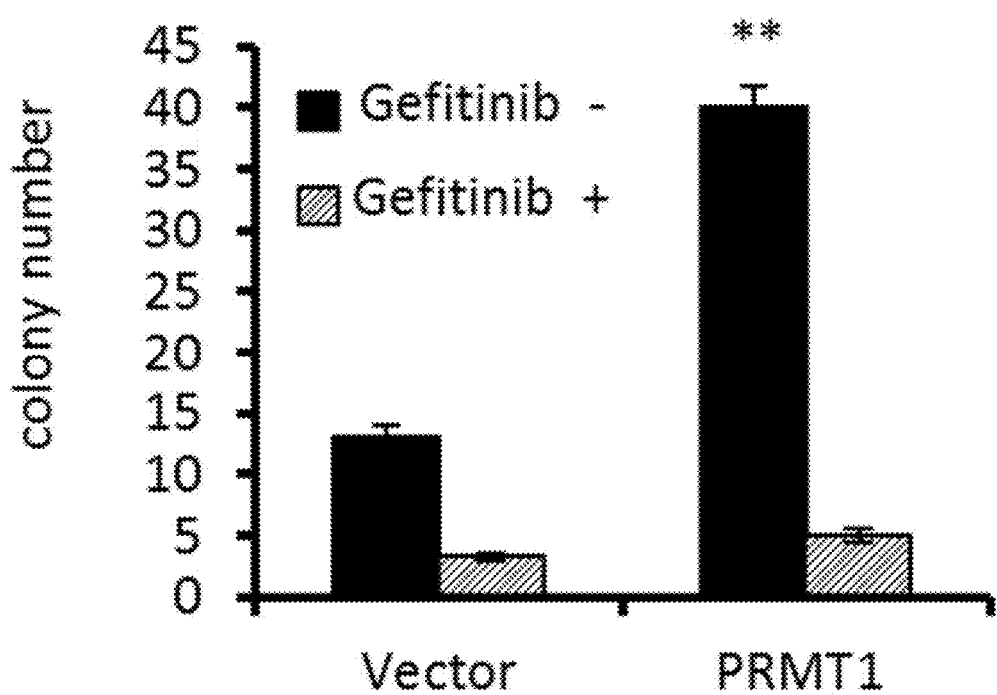
Figure 1E:
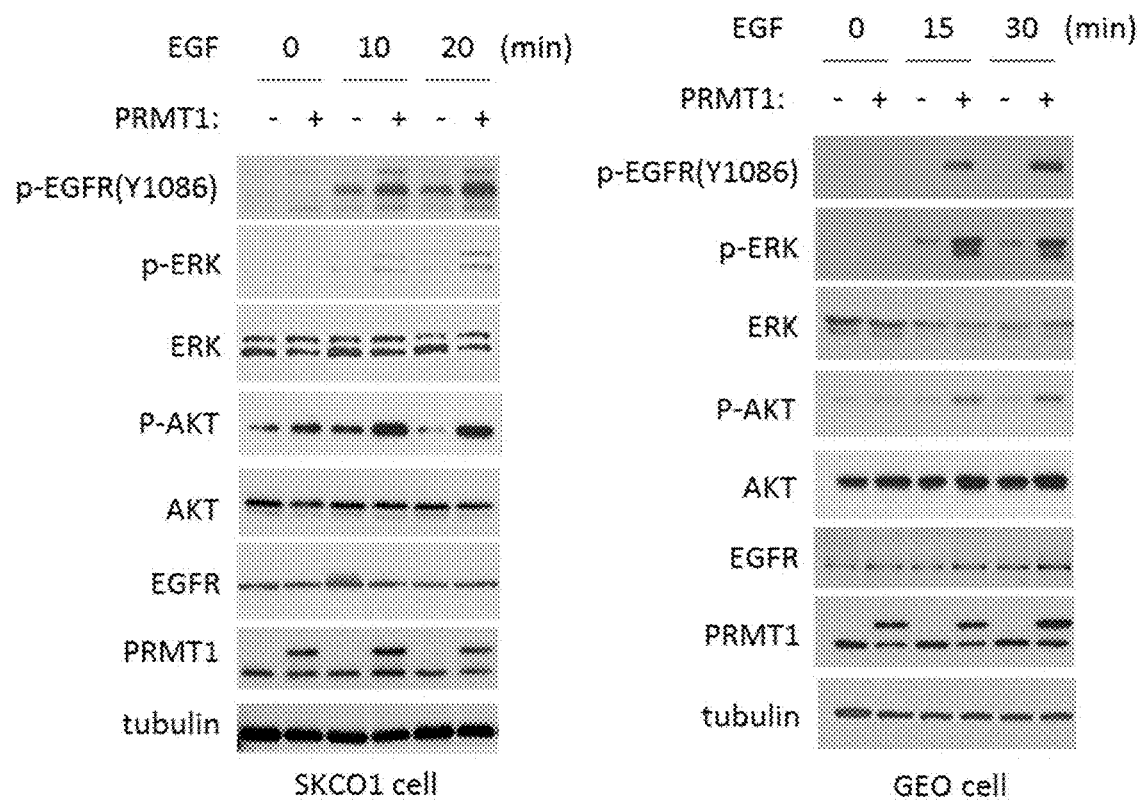
Figure 1F:
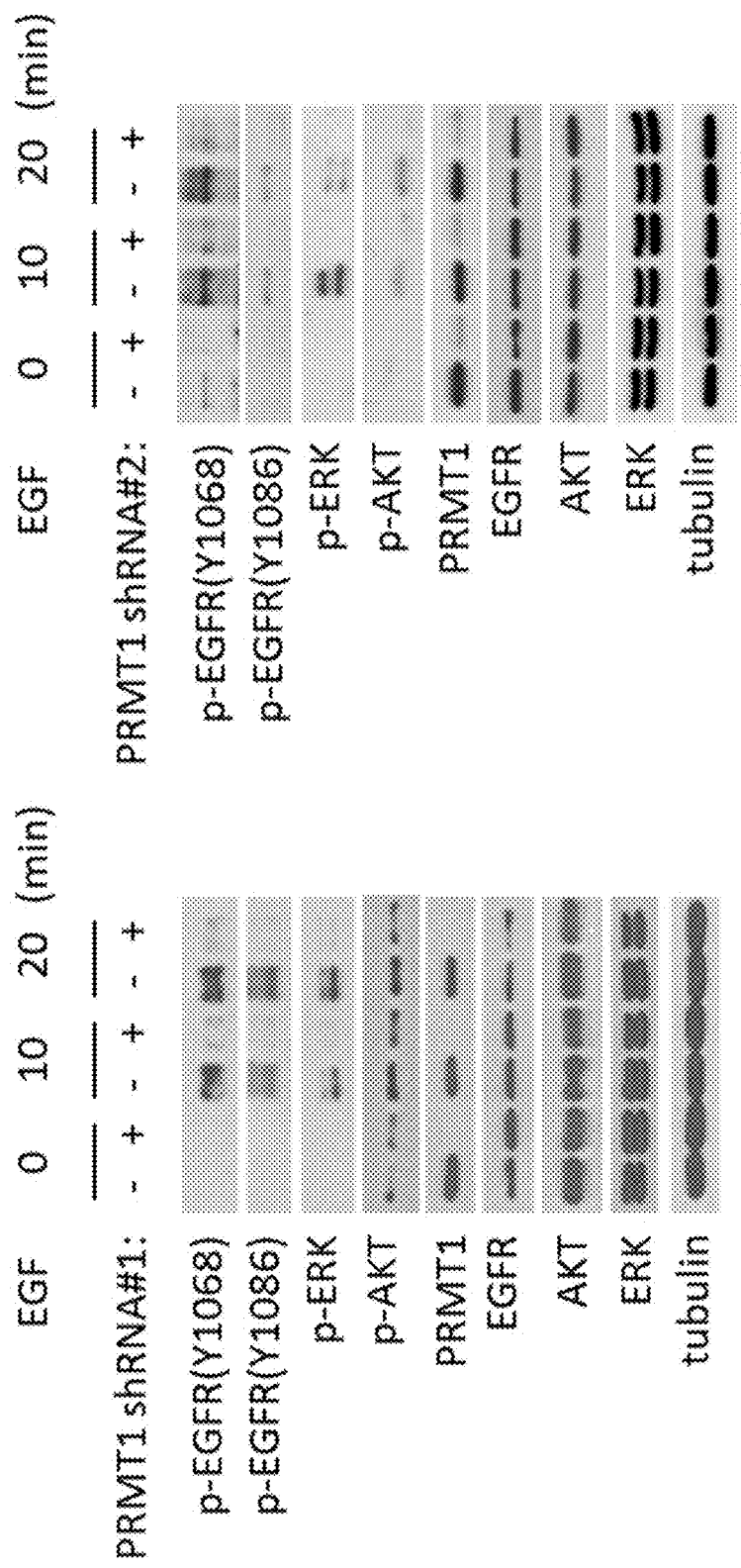

Protein arginine methylation is involved in many biological processes, including cancer development. Among the ten mammalian protein arginine methyltransferases (PRMTs), PRMT1 is the best characterized (Bedford and Richard, 2005; Le Romancer et al., 2008). In particular, aberrant high expression of PRMT1 has been observed in colorectal, breast, prostate, and lung cancers and suggested as a predictive marker for poor clinical outcomes (Yang and Bedford, 2013; Papdokostopoulou et al., 2009). Although PRMT1 appears to play a crucial role during colorectal cancer tumorigenesis, how it is involved in colorectal cancer pathophysiology remains obscure. Given that high PRMT1 expression has been observed to correlate with colorectal cancer patient progression (Mathioudaki et al., 2008), whether this contributes to cancer cell proliferation was examined Indeed, stable transfectants that ectopically expressed PRMT1 had higher cell proliferation rates (FIG. 1A) and anchorage-independent colony formation ability (FIG. 1B) than control cells in both SKCO1 and GEO colorectal cancer cell lines, while knockdown of PRMT1 attenuated these effects. Interestingly, addition of gefitinib, an EGFR tyrosine kinase inhibitor, significantly inhibited cell proliferation (FIG. 1C) and colony formation (FIG. 1D) in both PRMT1-overexpressing and vector control (expressing endogenous PRMT1) cells. These phenomena were also observed in other non-colorectal cancer cell lines (FIG. 5), raising an interesting possibility that PRMT1-mediated cell growth is dependent on EGFR signaling. Interestingly, the activation status of EGFR and two main downstream signaling, ERK and AKT were stronger in PRMT1-overexpressing than vector control cells (FIG. 1E) upon EGF stimulation, and knockdown of PRMT1 severely blocked EGF-induced EGFR, ERK and AKT activation (FIG. 1F). Collectively, these results suggest that PRMT1 enhances EGFR signaling in response to EGF stimulation.

Figure 2A:
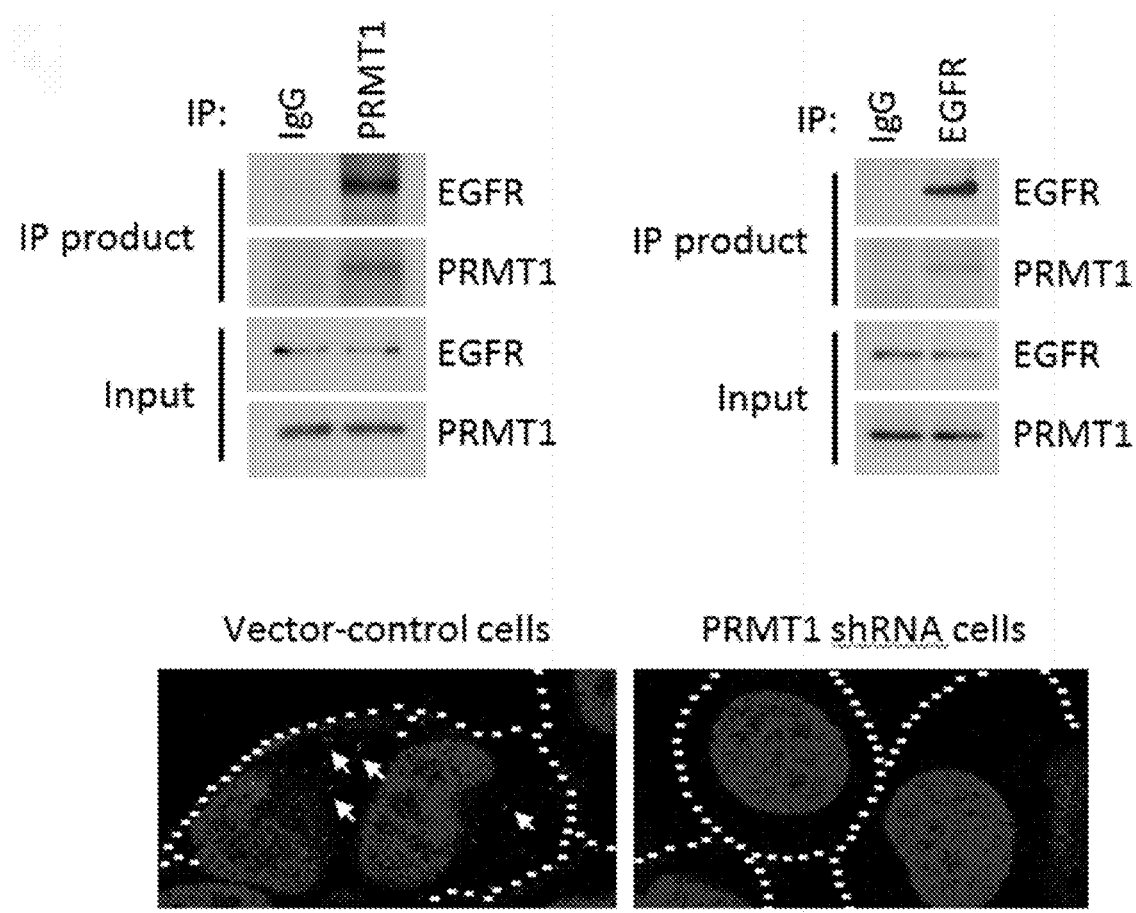
Figure 2B:
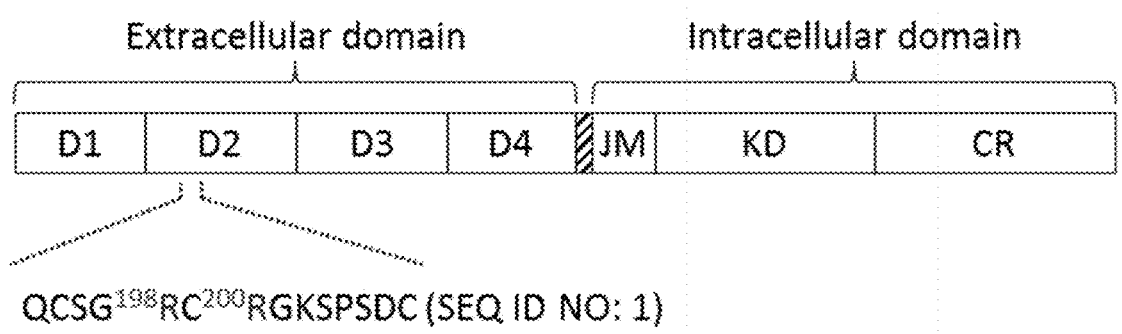
Figure 2C:
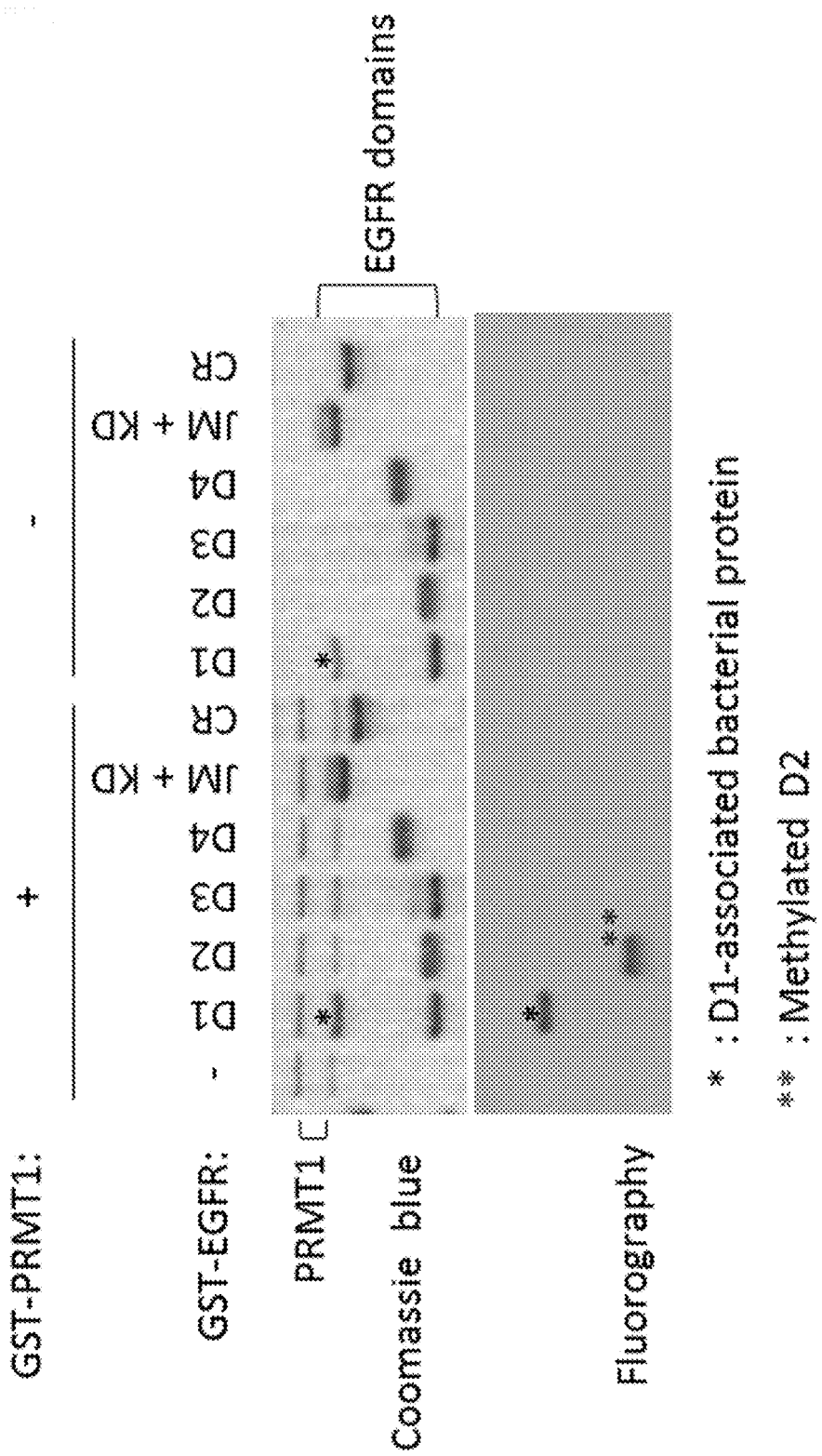
Figure 2E:
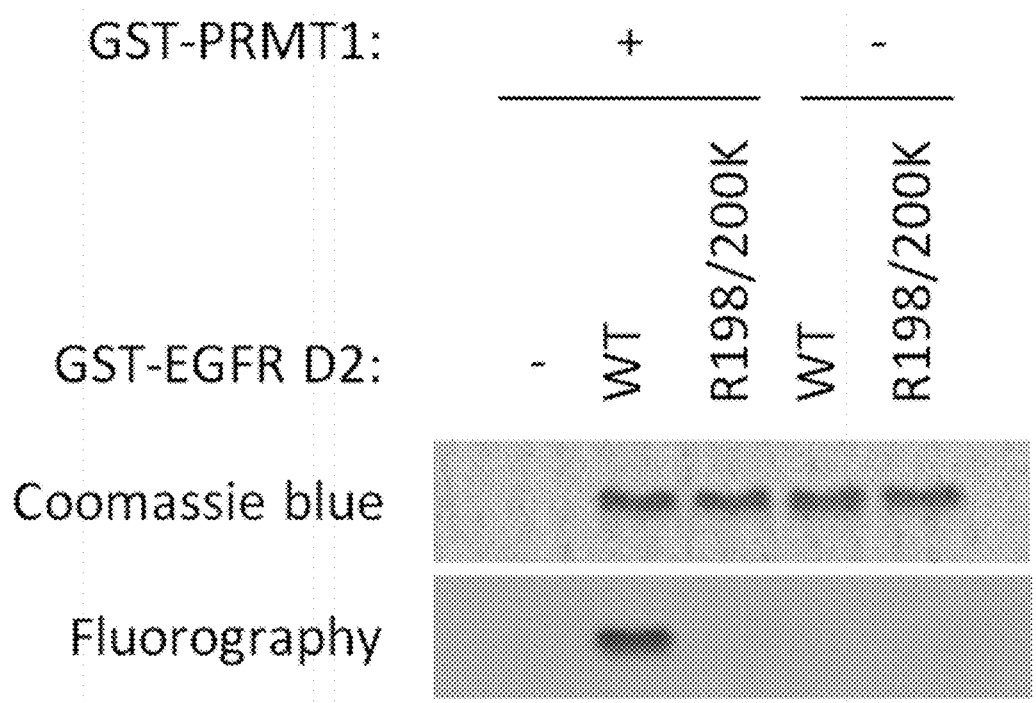
Figure 2F:
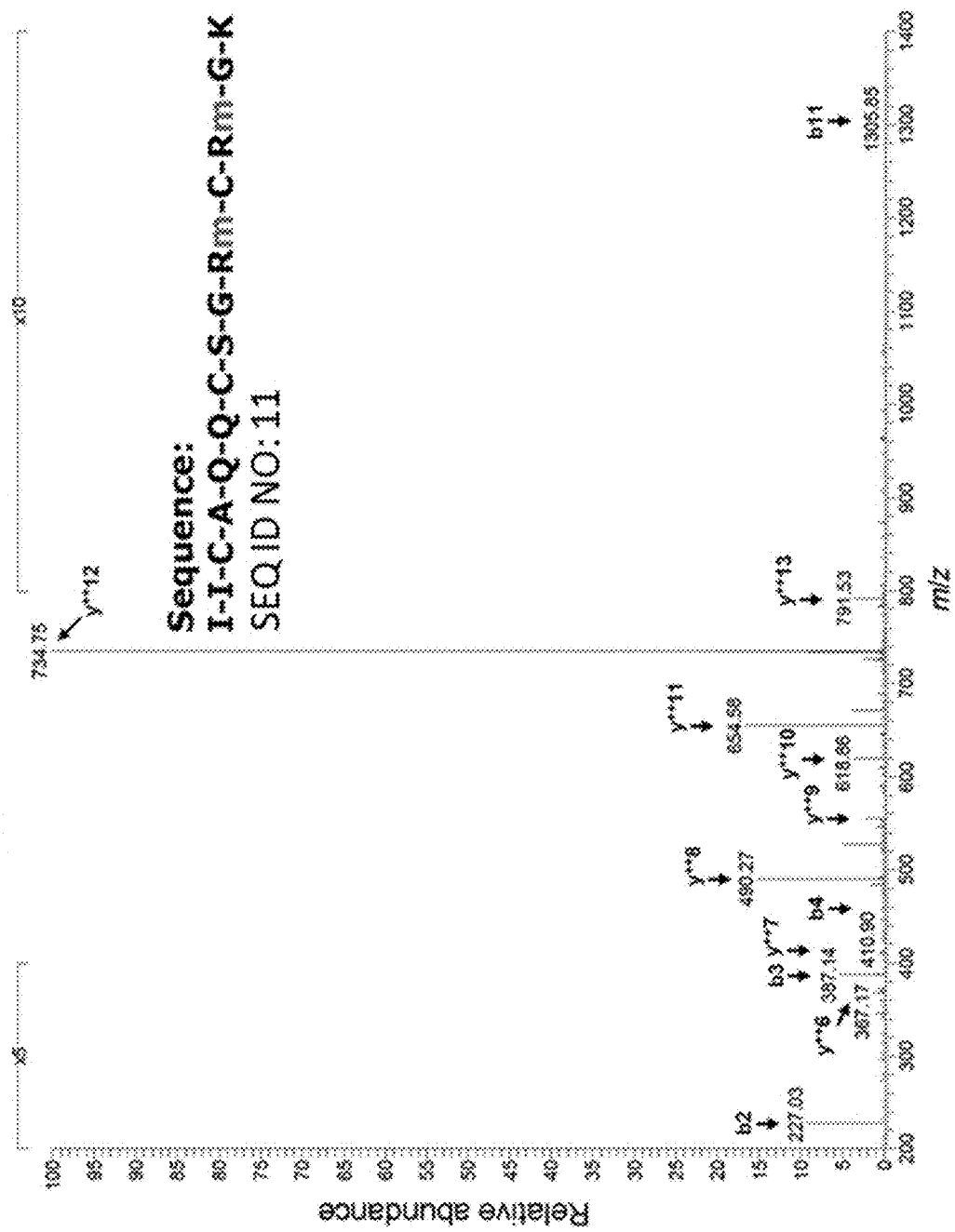
Figure 2G:
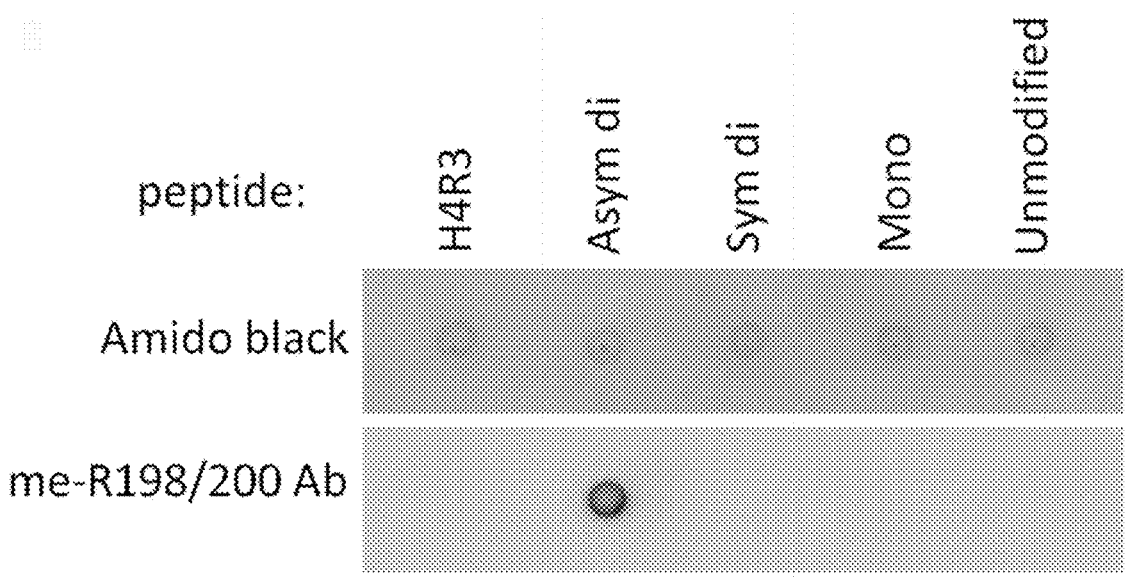
Figure 2H:
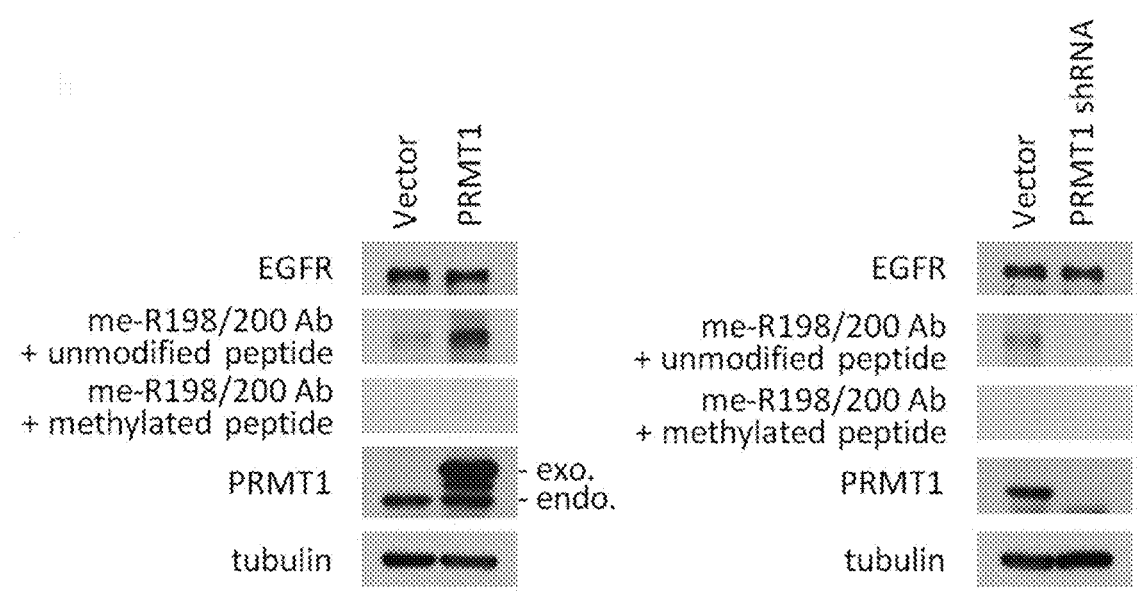

Next, whether PRMT1 affects EGFR signaling through protein arginine methylation of EGFR was determined. Results from reciprocal coimmunoprecipitation (FIG. 2A, top) and Duolink® assay (FIG. 2A, bottom) demonstrated a physiological association between endogenous PRMT1 and EGFR. Among various functional domains of EGFR (FIG. 2B), PRMT1 specifically methylated the extracellular domain 2 (D2) of EGFR (FIG. 2C). PRMT1 frequently methylates arginine residues found within glycine-arginine rich (GAR) domains (Boisvert et al., 2005; Yu et al., 2012) and generates asymmetric dimethylated arginine. Sequence alignment between the GAR domains of known PRMT1 substrates and D2 of EGFR revealed a putative GAR domain with two arginine residues, R198 and R200 (FIG. 2D). PRMT1 methylated wild-type but not R198/200K D2 mutant EGFR (FIG. 2E), indicating that these two arginine residues are the major targets of PRMT1-mediated EGFR methylation. In addition, mass spectrum analysis of immuno-purified endogenous EGFR proteins indicated R198 and R200 of EGFR were dimethylated (FIG. 2F). A specific anti-me-R198/200 antibody was generated by using a synthesized asymmetric dimethylated EGFR peptide. Dot blot assays showed that this me-R198/200 antibody recognized asymmetric dimethylated EGFR peptide but not unmodified peptide or other methylation forms (FIG. 2G). The antibody was then used to analyze the methylation status of endogenous EGFR in SKCO1 cells. Indeed, the level of EGFR methylation was proportional to PRMT1 expression and could be competed off by methylated but not by unmodified peptide (FIG. 2H), indicating a positive regulatory role of PRMT1 on EGFR R198/200 methylation Immunochemistry staining of colon cancer tissue using the EGFR methylation antibody, me-R198/200, showed that the antibody competed with synthesized methylated EGFR peptide, but not unmodified EGFR peptide or histone H4R3 methylated peptide, showing the capability of the EGFR methylation antibody to detect methylation signals in tumor tissue. The me-R198/200 antibody was also used in immunohistochemistry studies of GEO cells expressing either wild-type EGFR or R198/200K D2 mutant EGFR. Positive staining was seen with wild-type EGFR expression but not R198/200K D2 mutant EGFR. Furthermore, the staining seen with wild-type EGFR expression was eliminated by the presence of an asymmetric dimethylated R198/200 EGFR peptide competitor, but not by an unmodified R198/200 EGFR peptide competitor or asymmetric dimethylated histone H4R3 peptide competitor. Taken together, these results indicate that PRMT1 interacts with and methylates R198 and R200 of EGFR.

Figure 3A:
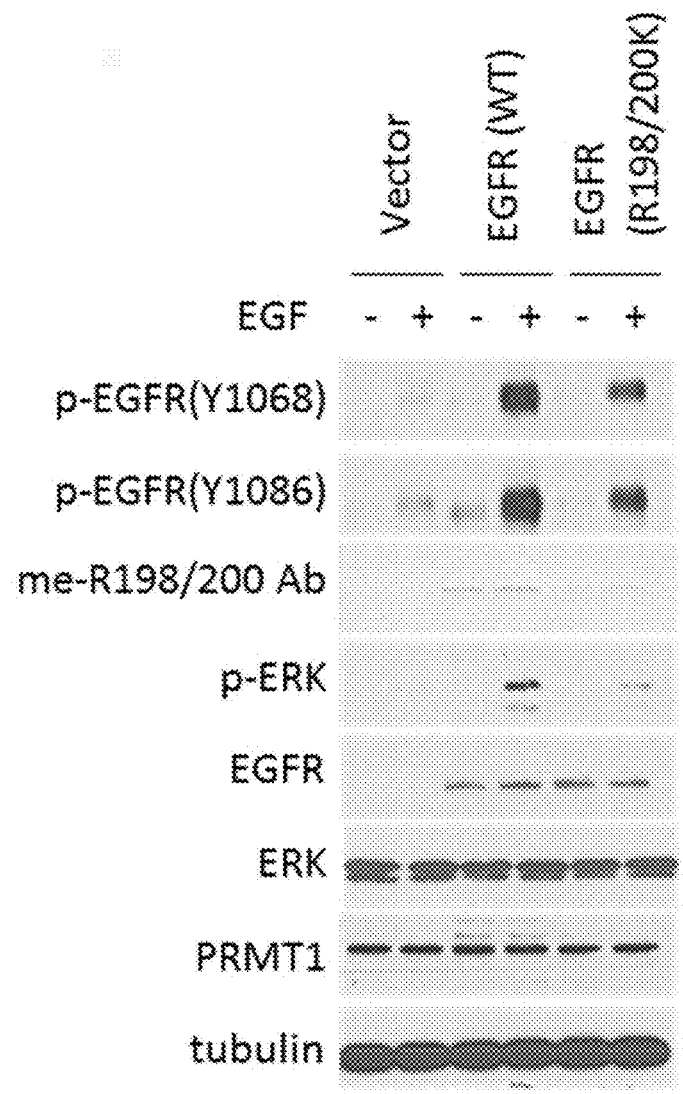
FIGS. 3A-F. PRMT1-mediated R198/200 methylation upregulates EGFR dimerization and activation and is correlated with poor patient outcome.
Figure 3B:
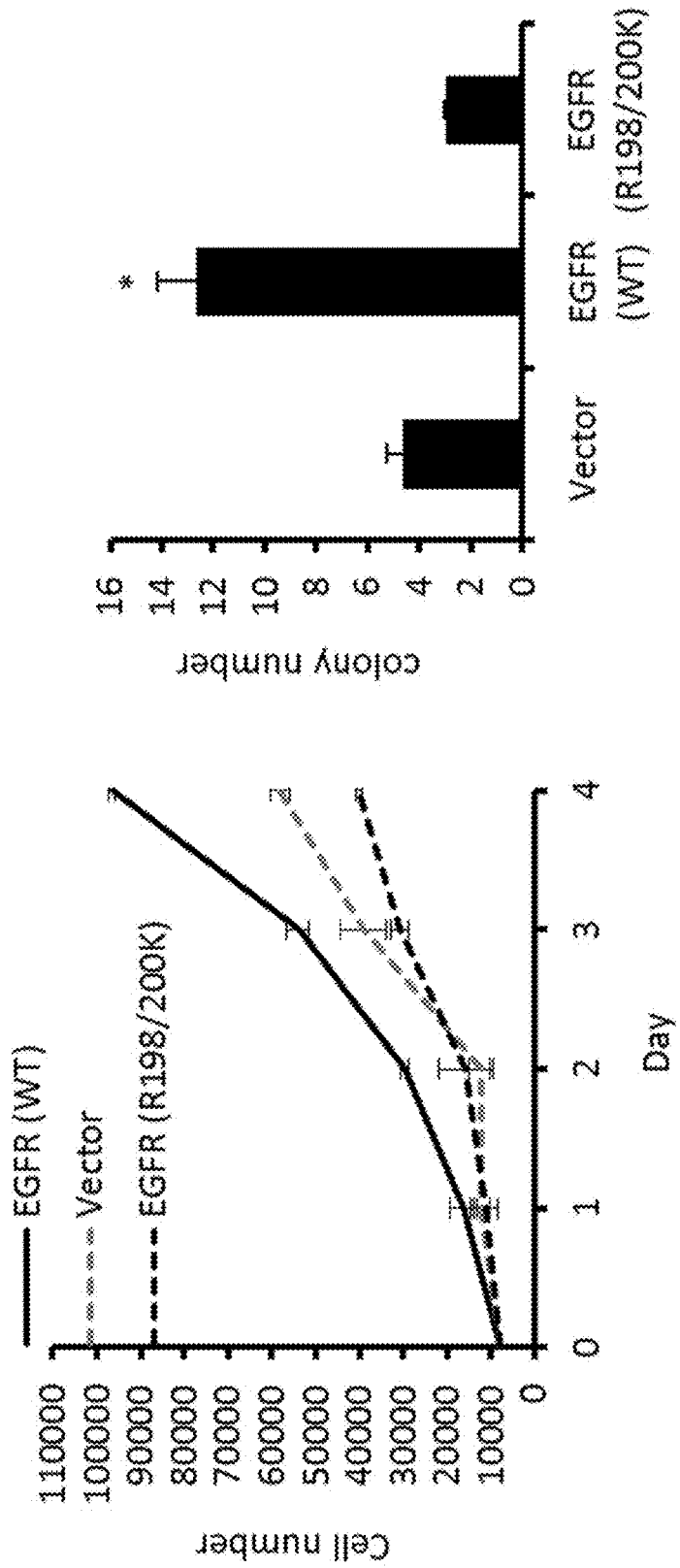
Figure 3C:
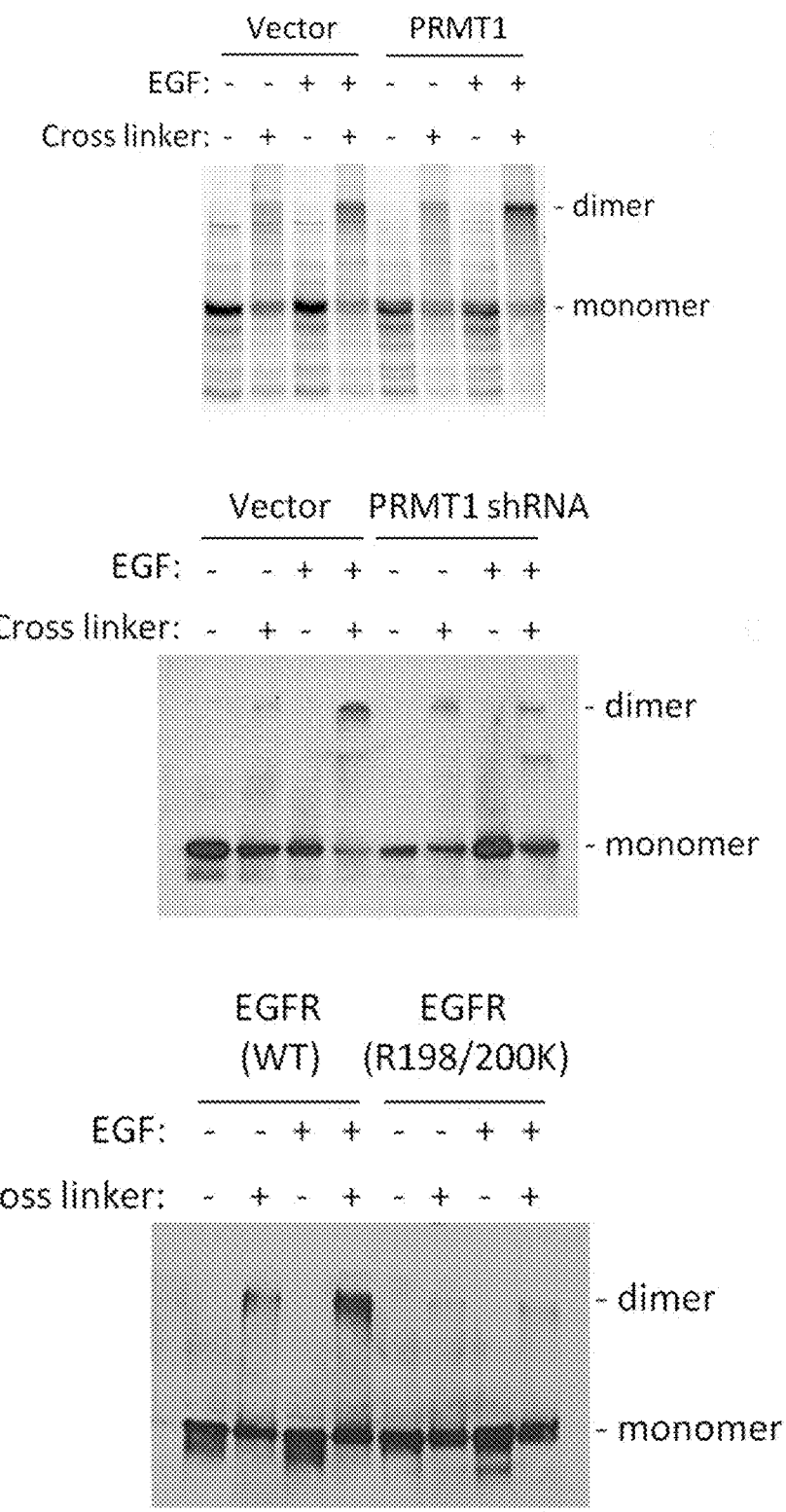
Figure 8:
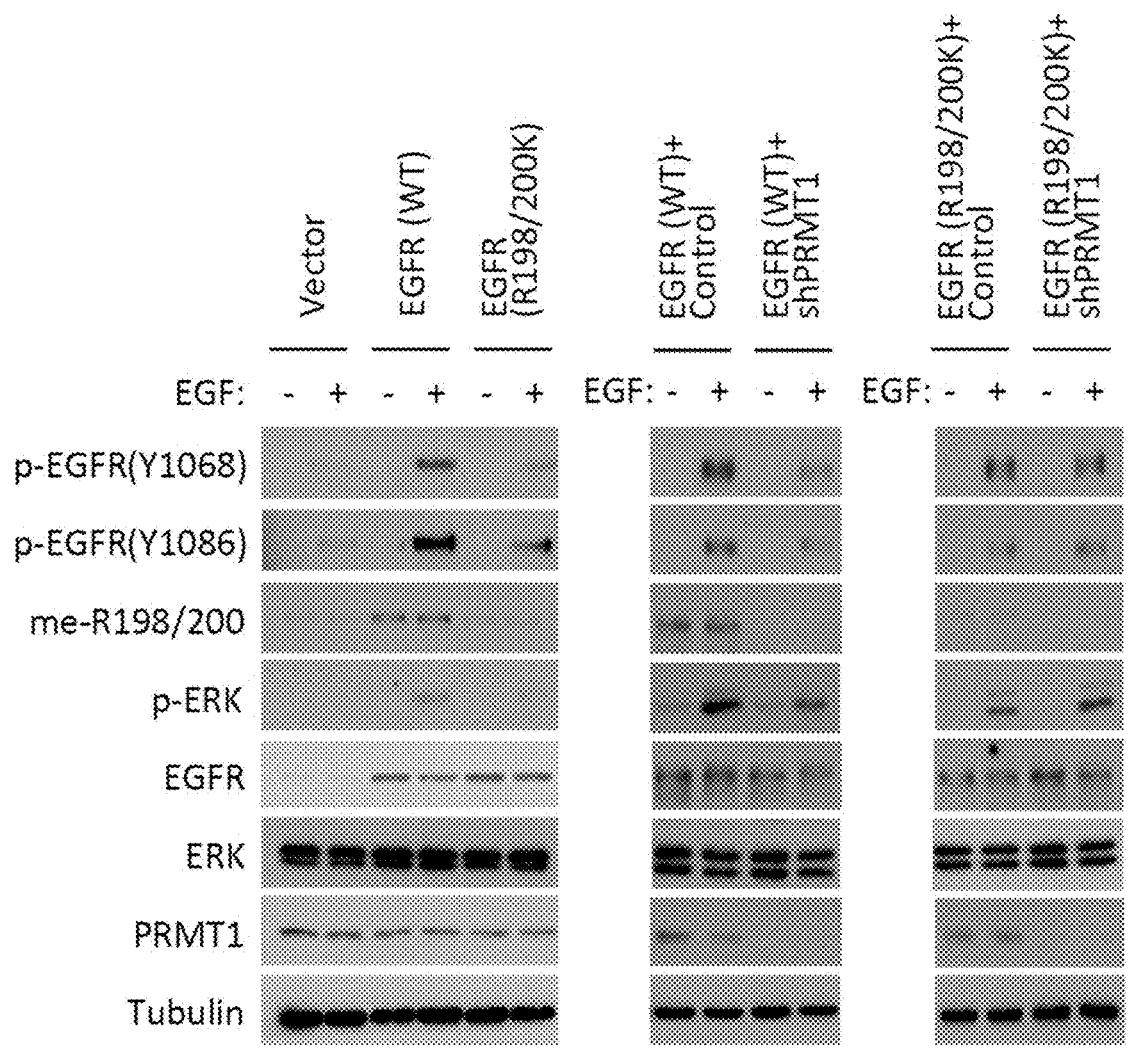
FIG. 8. PRMT1 upregulates EGFR activation Immunoblot comparing EGFR and downstream ERK activation levels in HT29 cells expressing control vector, WT, and R198/200K mutant EGFR with or without PRMT1 knock down upon EGF stimulation.

To determine the role of EGFR R198/200 methylation in EGFR signaling, a full-length EGFR R198/200K mutant that cannot be methylated by PRMT1 was constructed for comparison with wild-type EGFR. Since both pEGFR and pERK were significantly changed by overexpression or knockdown of PRMT1 (FIGS. 1E and 1F), they used as markers to monitor EGFR signaling. Notably, the phosphorylation of EGFR and ERK (FIGS. 3A and 8), cell proliferation rate (FIG. 3B, left), as well as anchorage-independent colony formation ability (FIG. 3B, right) were significantly reduced in cells expressing the R198/200K mutant compared with those expressing the wild-type EGFR. The effect of EGFR R198/200 methylation by PRMT1 on EGFR signaling and subsequent cell growth prompted an investigation into how this modification leads to these changes. Interestingly, upon EGF stimulation, endogenous EGFR of PRMT1-expressing SKCO1 cells showed higher receptor dimerization ability, which is partially regulated by the D2 of EGFR (Chung et al., 2010), than cells expressing control vector (FIG. 3C, top). In contrast, EGFR in PRMT1 shRNA-expressing cells had lower dimer formation than cells expressing control vector (FIG. 3C, middle). Consistently, loss of methylation of EGFR R198/200K mutant significantly reduced its dimerization ability compared with wild-type EGFR in GEO cells (FIG. 3C, bottom). These results support a model that methylation at R198/200 of EGFR by PRMT1 enhances its dimerization ability, and provide an explanation for PRMT1-upregulated EGFR signaling and cell proliferation.

Figure 3D:
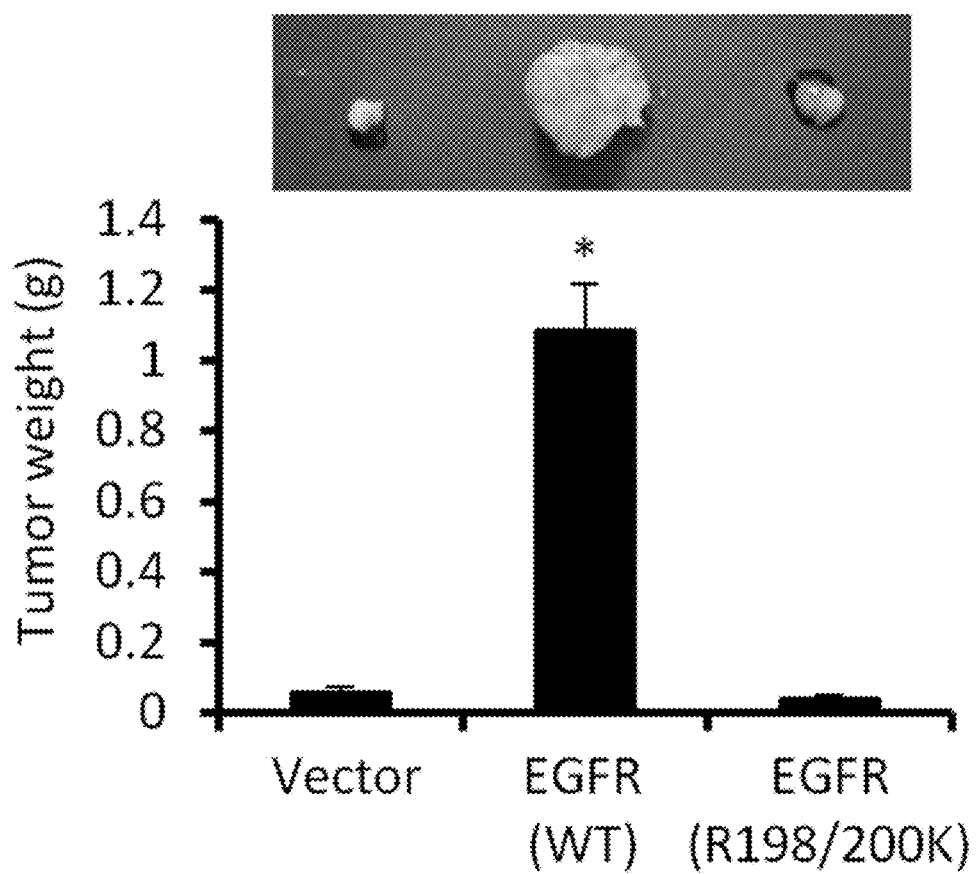
Figure 3E:
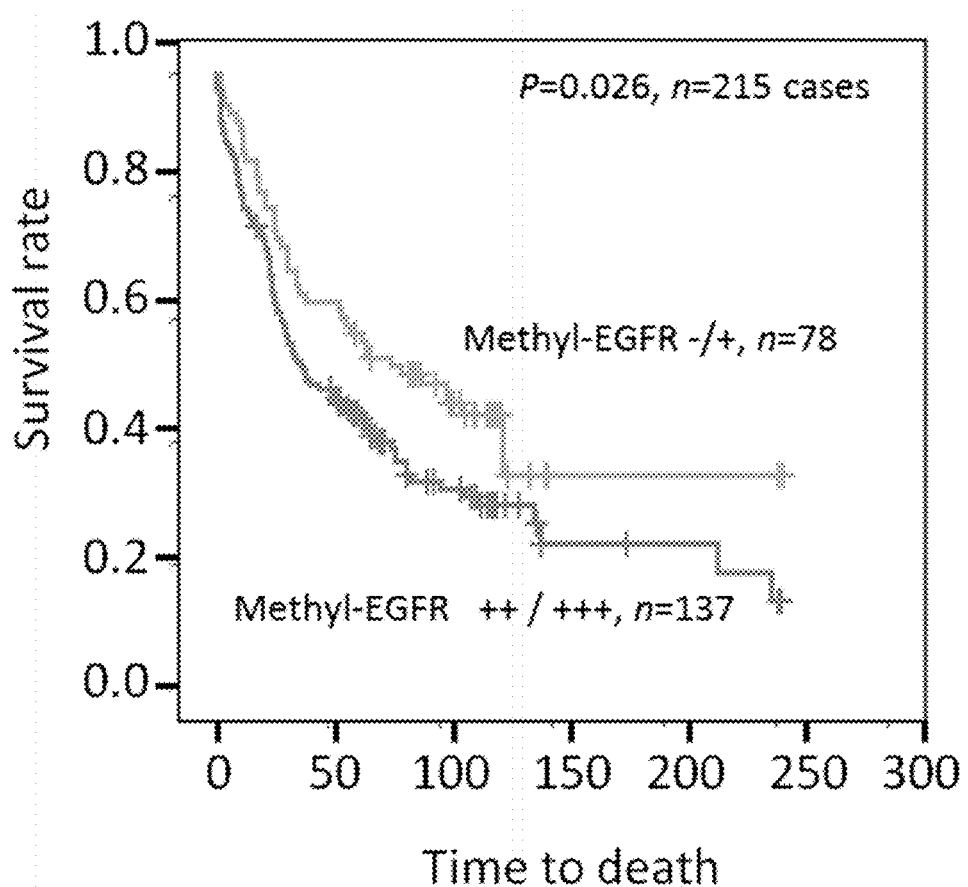
Figure 3F:
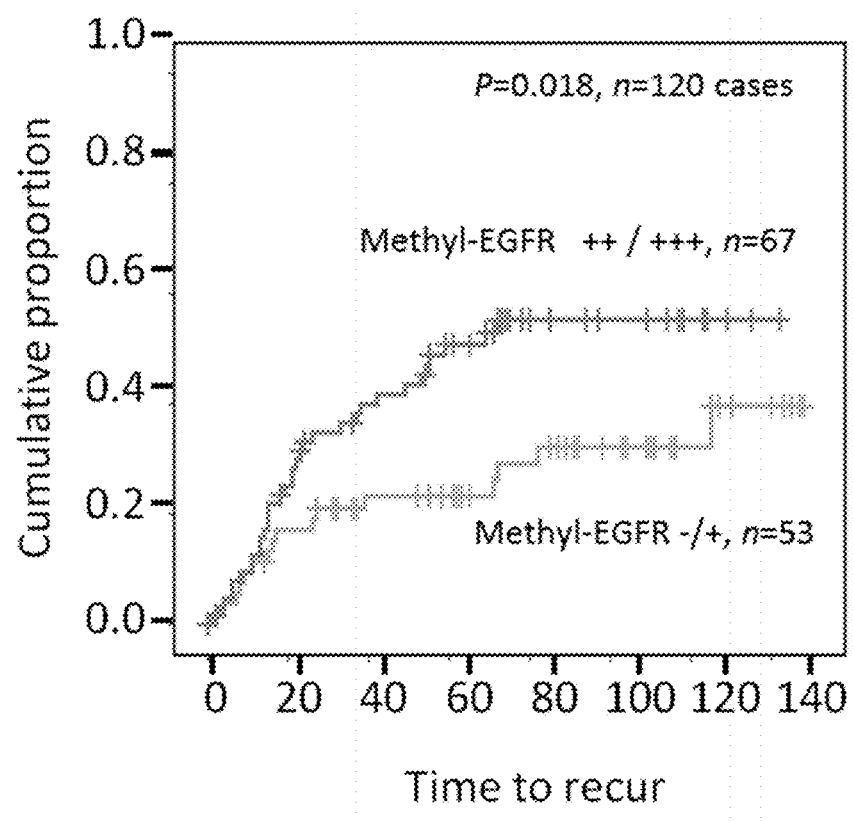

Whether PRMT1-mediated EGFR methylation contributes to tumorigenesis in an orthotopic colon cancer mouse model was further examined One month after injection, cells expressing wild-type EGFR generated significantly larger tumors than those expressing R198/200K EGFR or vector control (FIG. 3D). A retrospective study of clinical colorectal cancer specimens further indicated that EGFR R198/200 methylation level as detected by me-R198/200 Ab correlated significantly with poor patient survival (FIG. 3E) and higher recurrence rate (FIG. 3F). Collectively, these results suggest that the methylation status of EGFR has the potential to serve as a predictive marker for patient prognosis.

Figure 4A:
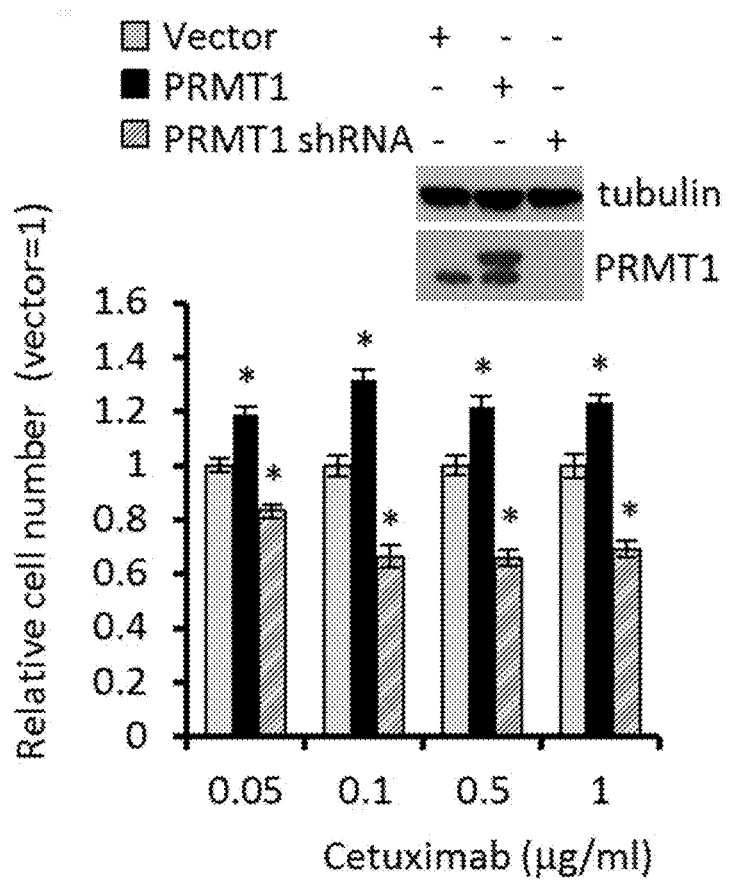
FIGS. 4A-H. PRMT1 enhances EGF binding to EGFR and increases cetuximab resistance in colon cancer cells.
Figure 4B:
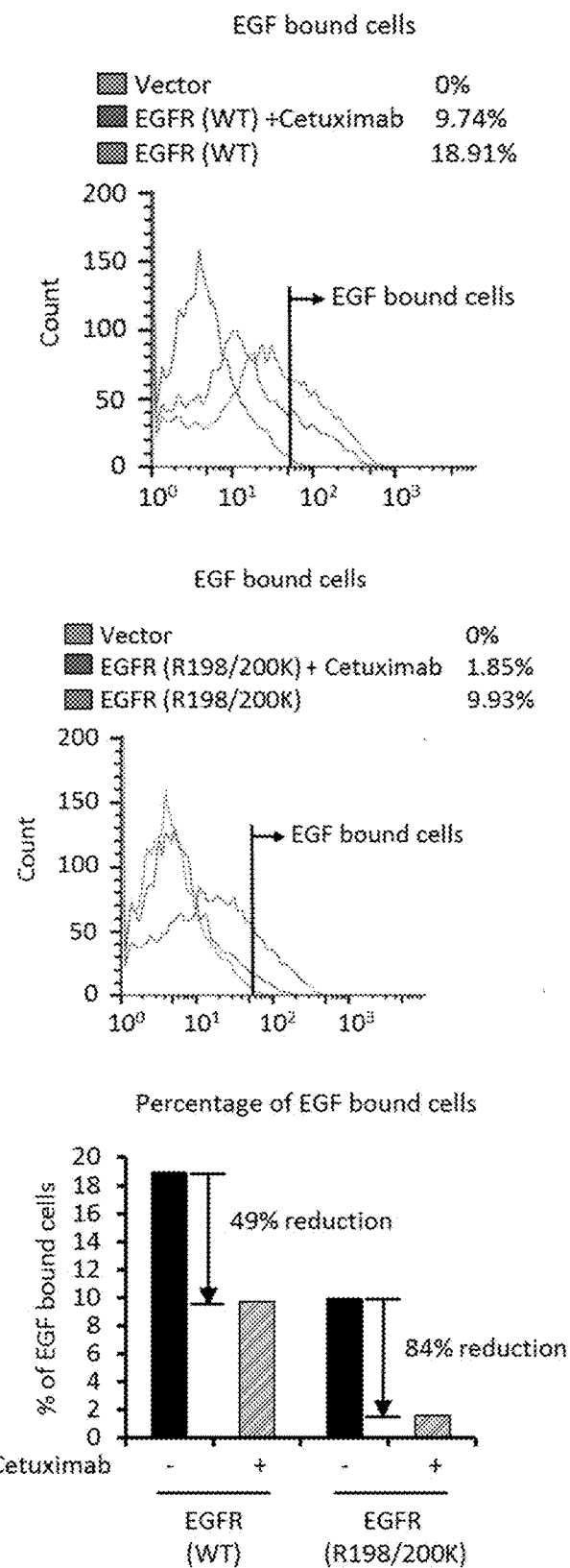
Figure 4C:
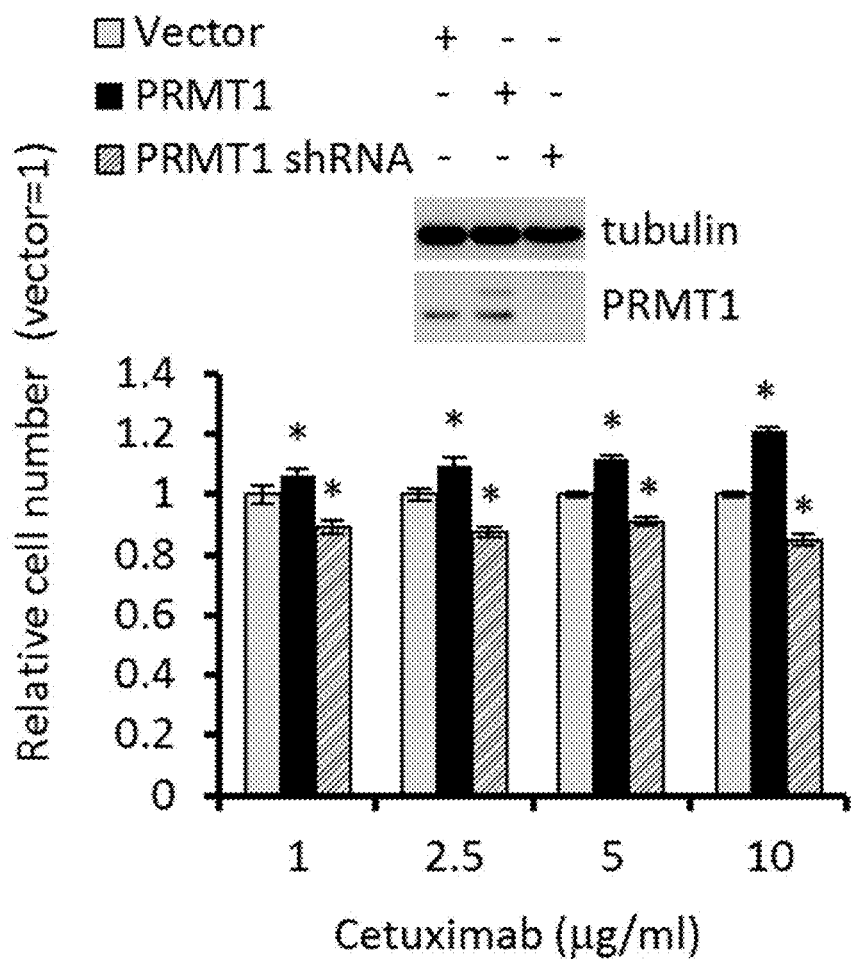
Figure 4D:
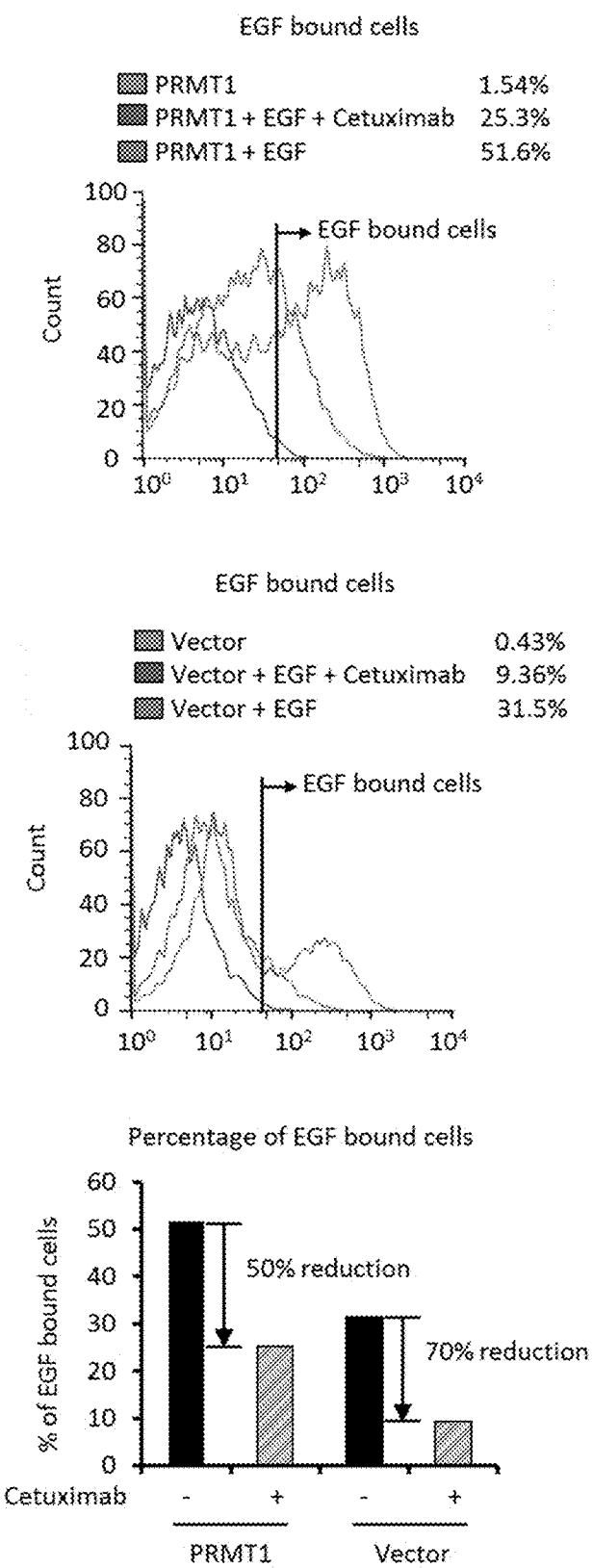
Figure 4E:
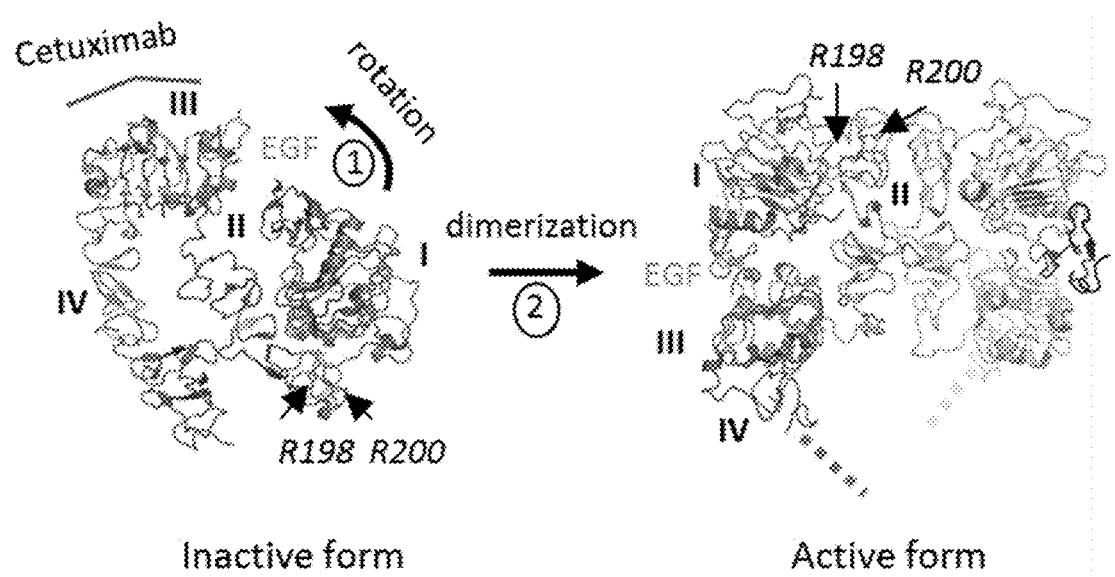
Figure 4F:
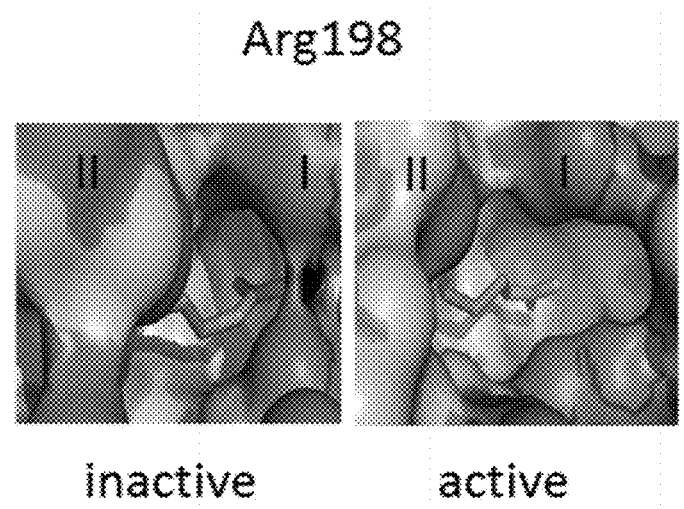
Figure 4G:
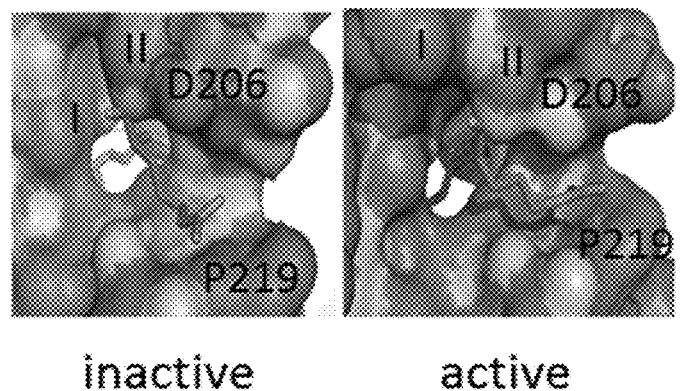
Figure 4H:
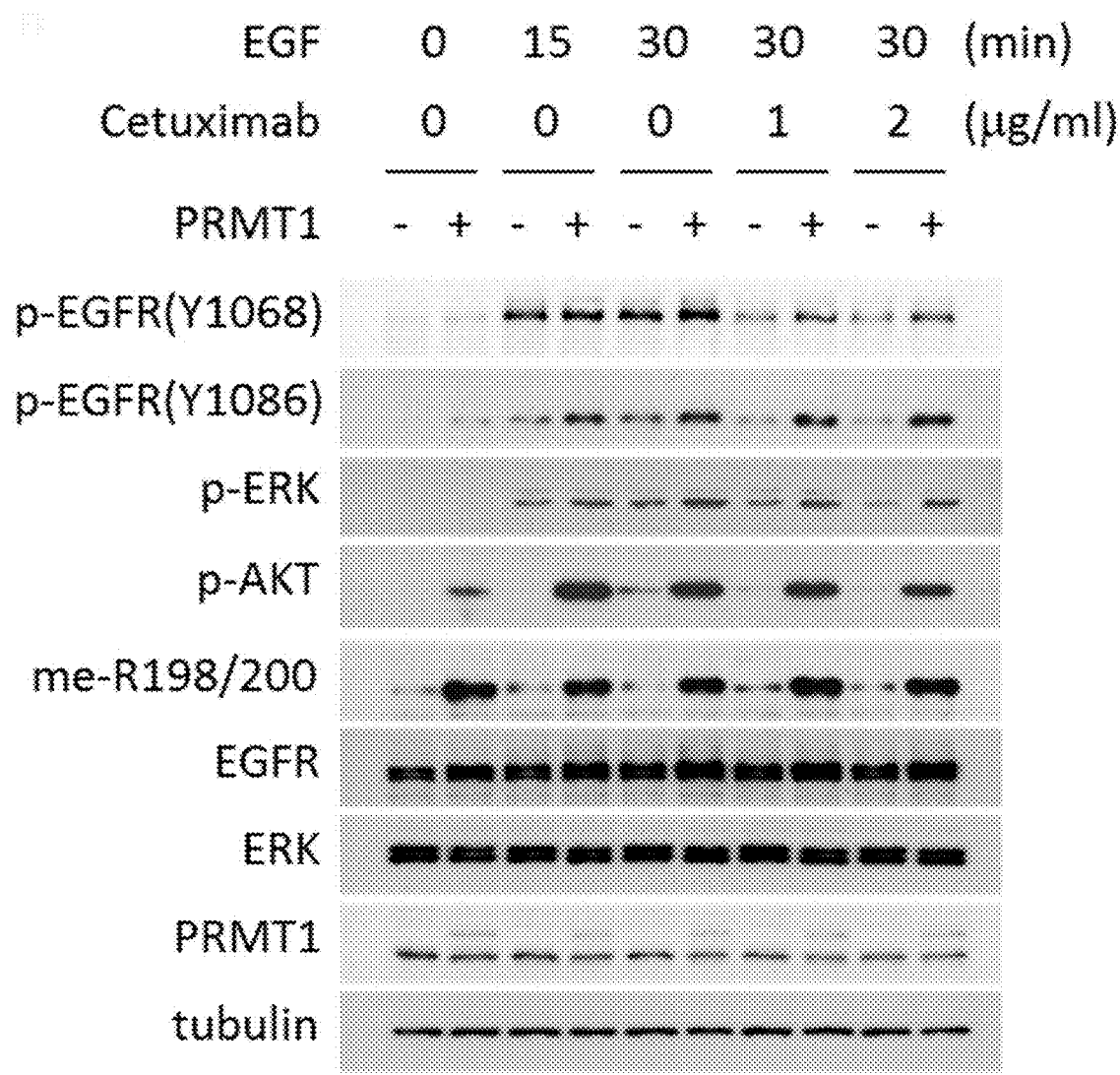

Clinically, cetuximab is used to treat metastatic colorectal cancer by disabling the interaction between EGF ligand and EGFR and attenuating EGFR signaling (Gill et al., 1984; Li et al., 2005). Given that the extracellular domain of EGFR is the target of cetuximab, whether R198/200 methylations affect the efficacy of cetuximab was examined. In GEO cells expressing exogenous PRMT1, cell growth rate in the presence of cetuximab was higher than vector control cells while knockdown of PRMT1 sensitized cells to cetuximab (FIG. 4A). To further determine how R198/200 methylation affects cetuximab response, the binding affinity between EGFR and EGF was evaluated in the presence or absence of cetuximab by flow cytometry. As shown in FIG. 4B, GEO cells expressing wild-type EGFR (left) had higher binding affinity (18.91%) to APC-conjugated EGF than those expressing the R198/200K mutant (9.93%; middle). Moreover, cetuximab was more effective in reducing the number of EGF-bound cells in cells expressing R198/200K mutant than in those expressing wild-type EGFR (84% versus 49%; FIG. 4B, bottom), suggesting that methylated EGFR responds better to EGF binding and is more resistant to cetuximab treatment (FIG. 10A). Because only patients with wild-type KRAS are recommended to receive cetuximab therapy for current colorectal cancer treatment (Morton and Hammond, 2009), the cell growth of SW48 cells, a wild-type KRAS cell line, expressing exogenous PRMT1, PRMT1 shRNA, or control vector under cetuximab treatment was investigated. Similar to KRAS G12A mutant GEO cells, SW48 cells expressing exogenous PRMT1 had higher growth rate than vector control cells in the presence of cetuximab while cells expressing PRMT1 shRNA had lower growth rate (FIG. 4C). Consistently, cells expressing PRMT1 (FIG. 4D, top; FIGS. 10B-C) had higher EGF binding affinity (51.6% versus 31.5%) and lower cetuximab response than vector control cells (50% versus 70% reduction; FIG. 4D, middle and bottom; FIGS. 10B-C). These observations are further supported by structural analysis of the extracellular portion of EGFR dynamically transitioning between a monomeric inactive, 'tethered' conformation and an active, dimeric conformation (FIG. 4E). Arginines 198 and 200 are situated in the hinge region between domains I and II (Ogiso et al., 2002; Ferguson et al., 2003). In the inactive conformation, EGFR domain I only provides a narrow pocket for Arg 198 (FIG. 4F, left). Asymmetric dimethylation by PRMT1 would increase the volume of the Arg198 side chain sufficiently to cause unfavorable steric clashes with domain I, and hence disfavor the inactive conformation. In the active form, the same binding pocket is substantially enlarged (FIG. 4F, right) and would provide sufficient space and some hydrophobic surface patches to accommodate asymmetric dimethylation. Meanwhile, in the inactive form, Arg200 compensates for the charge of Asp206 (FIG. 4G, left), and the backbone carbonyl of Asp206 binds to the backbone nitrogen of Arg200. In the active form, the side chain of Asp206 is rotated away and exposed to the solvent, and the Asp206 carbonyl forms a hydrogen bond with Arg200. Due to these rearrangements, Arg200 is positioned close to the hydrophobic surface provided by Pro219 (FIG. 4G, right). Asymmetric dimethylation of Arg200 appears more favorable in the active conformation, because it provides a more hydrophobic environment for Arg200. Cetuximab binds exclusively to the domain III of the extracellular portion of EFGR in its inactive ('tethered') conformation (FIG. 4E). In doing so, cetuximab partially hides the ligand-binding site and sterically prevents EGFR from adopting the active ('open') conformation required for ligand binding and dimerization (Li et al., 2005). By favoring the active dimeric conformation and ligand binding, methylation of arginines 198 and 200 would oppose the interactions of EGFR with cetuximab. In line with the higher EGF binding affinity and higher EGFR methylation level, PRMT1-expressing SW48 cells demonstrated higher EGFR and ERK activation after EGF stimulation, and the upregulated pEGFR and pERK remained relatively strong even in the presence of cetuximab in comparison to vector control cells (FIG. 4H). Together, the results suggest that PRMT1-mediated R198/200 methylation of EGFR favors EGF ligand binding and results in resistance to cetuximab.

Figure 6:
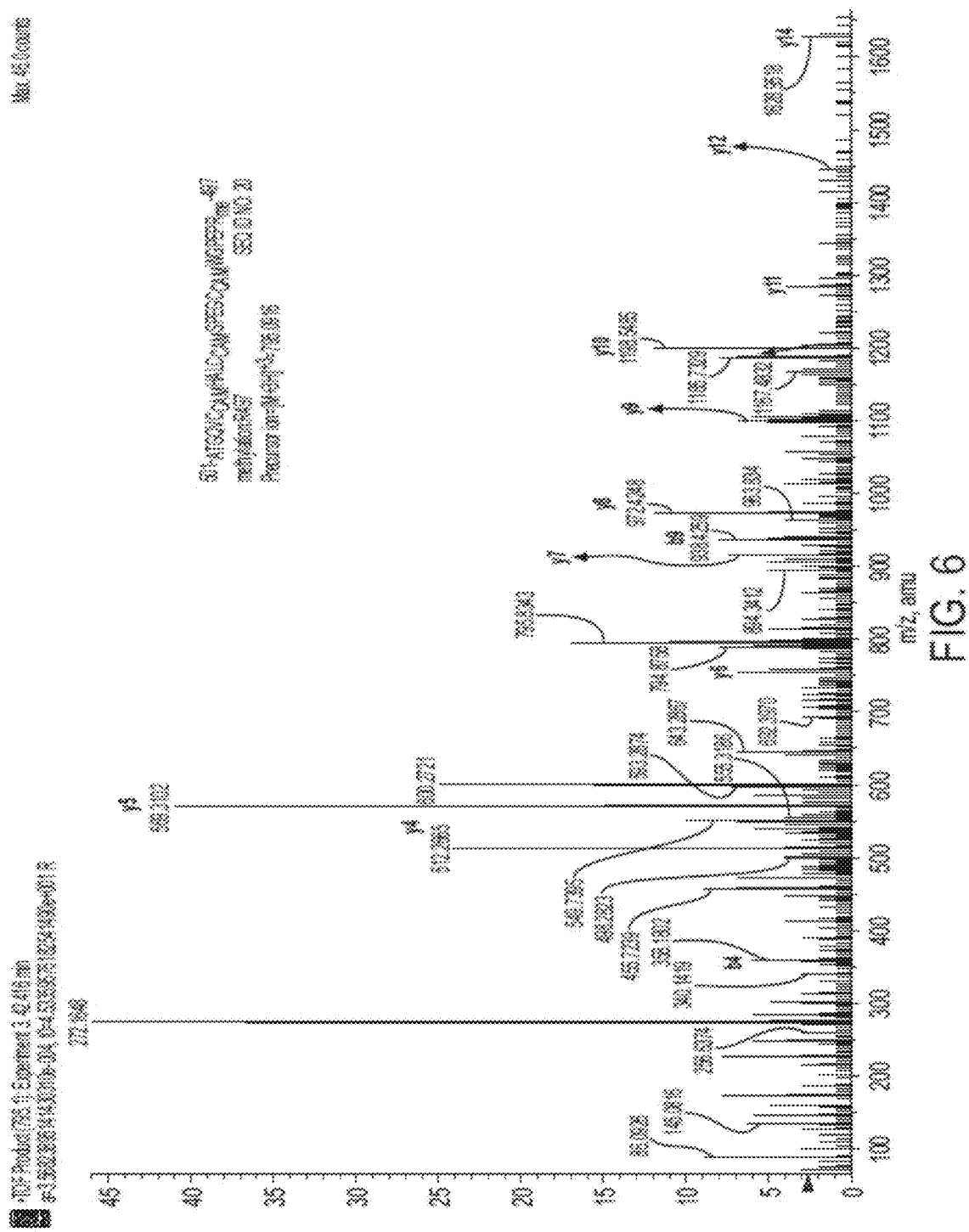
FIG. 6. Mass spectrum analysis showing R497 methylation on immunopurified endogenous EGFR. CLAM stands for S-carbamidomethylcysteine.

Interestingly, although some studies have shown that mutant KRAS leads to constitutive activation of ERK and bypasses EGFR signaling (van Houdt et al., 2010), ERK activation was still regulated by EGF stimulation in two KRAS mutant cell lines, GEO (KRAS G12A) and SKCO1 (KRAS G12V). Moreover, knockdown of PRMT1 sensitized cells to cetuximab treatment regardless of KRAS mutation status (FIGS. 4A and 4C), implying that EGFR R198/200 methylation has the potential to serve as a predictive marker for cetuximab resistance in clinical colorectal cancer therapy. It is noteworthy to mention that colorectal cancer patients carrying R497 polymorphism on EGFR extracellular domain 4 exhibit more unfavorable responses to cetuximab than those carrying K497 (Hsieh et al., 2012). Although endogenous EGFR R497 methylation was also observed from mass spectrum analysis (FIG. 6), indicating that this arginine methylation event may be another factor that contributes to cetuximab resistance, PRMT1 is not the methyltransferase for R497 methylation, at least from the present in vitro methylation assay (FIG. 2C). Further work will be performed to identify the PRMT that methylates R497.

Figure 7:
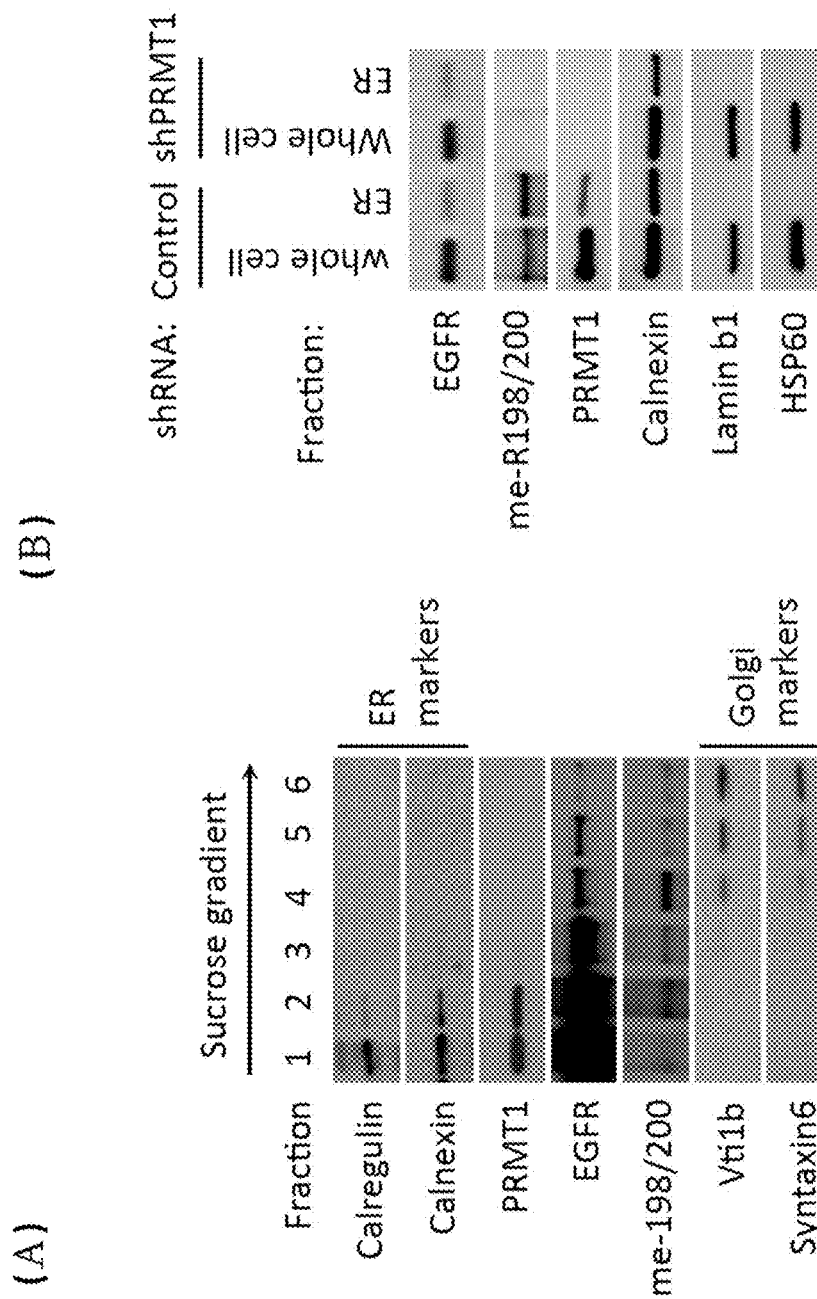
FIGS. 7A-B. PRMT1 interacts with and methylates EGFR during protein synthesis.
Figure 9A:
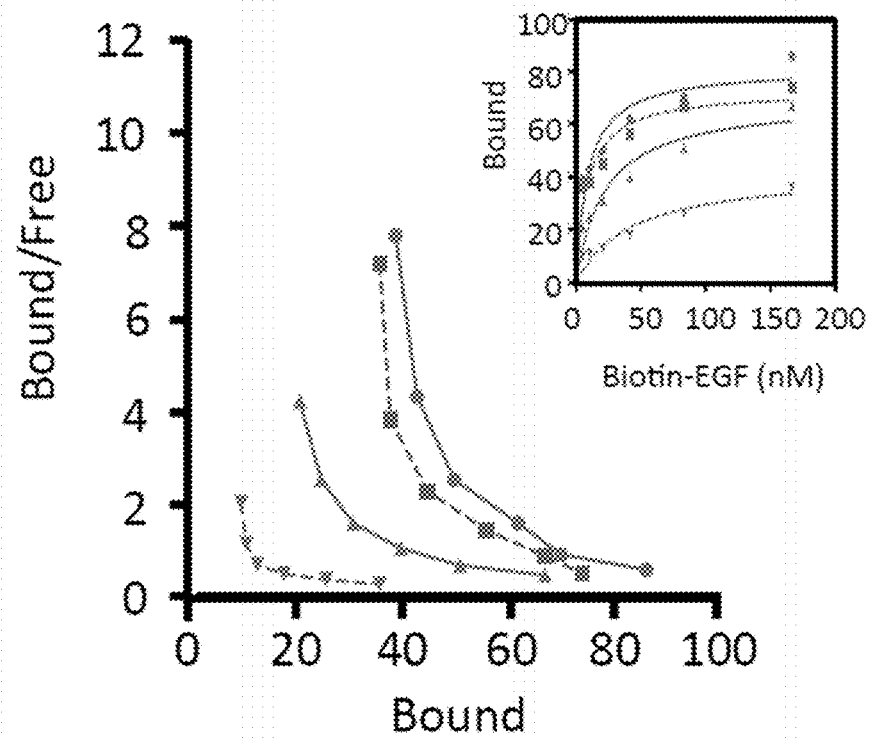
FIGS. 9A-C. EGFR methylation regulates EGF binding to EGFR.
Figure 9B:
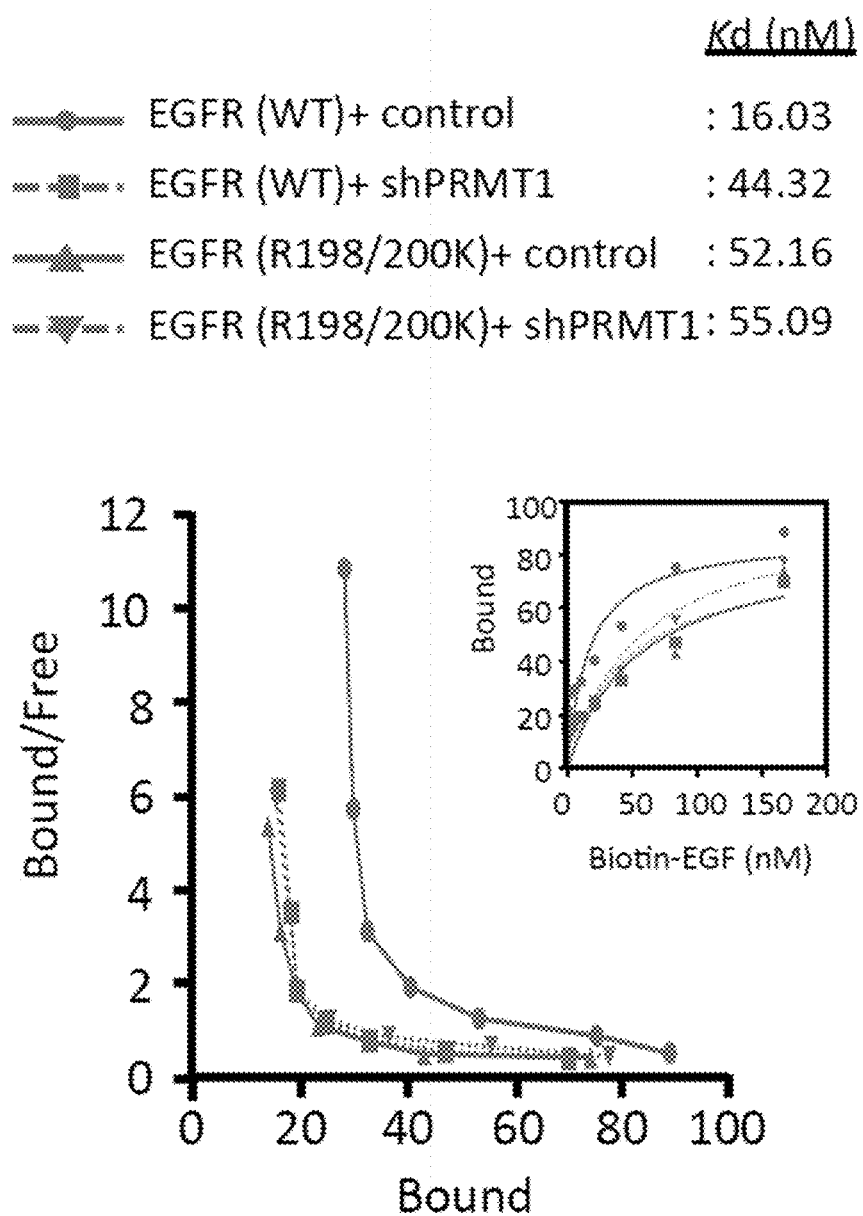
Figure 9C:
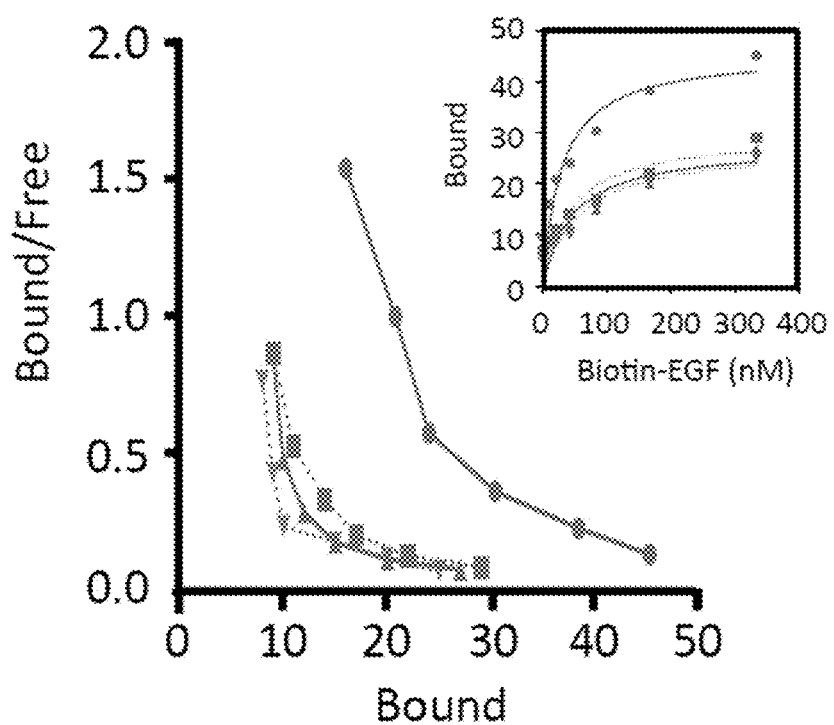

EGFR methylation is relatively new (Hsu et al., 2011) and not well characterized. The extracellular domain of tyrosine kinase receptor can also be methylated in addition to glycosylation. EGFR extracellular domain methylation, similar to glycosylation, occurs during protein synthesis (FIGS. 7A-B) and therefore cannot be regulated by EGF stimulation. Indeed, the PRMT1-EGFR interaction was found to occur on the endoplasmic reticulum surface, where protein syntheses occurs. Duolink® assays of SKCO1 cells found that PRMT1, EGFR, and the endoplasmic reticulum marker calnexin all co-localize. Furthermore, PRMT1 interacts with and methylates EGFR during protein synthesis (FIGS. 7A-B) without affecting the level of EGFR cell surface expression (FIGS. 10A-B). However, the signal that triggers PRMT1-mediated EGFR methylation is still unknown and needs further investigation. Overall, the role of PRMT1-mediated EGFR methylation in colorectal cancer tumorigenesis and its correlation with poor patient outcomes and cetuximab response by affecting the EGF-EGFR binding affinity (FIGS. 9A-C) provide an insight into the response to EGFR-targeted therapy and also open an avenue toward the understanding of how arginine methylation regulates the function of receptor tyrosine kinases.

Example 2—Combination Therapy with a PRMT Inhibitor and Cetuximab

The arginine methylation status of EGFR in patient samples treated with cetuximab will be determined in order to compare the status in those that respond to cetuximab with those that do not respond. PRMT inhibitors for use in combination with cetuximab will be identified, the effectiveness of the combination will be tested in vitro and in vivo. Additionally, studies will be performed to show that EGFR R198 and R200 methylation occurs in and induces resistance in other cancer types besides colorectal cancer.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945

Bedford and Richard, Arginine methylation an emerging regulator of protein function. *Mol. Cell,* 18:263-272, 2005.

Berg and Soreide, EGFR and downstream genetic alterations in KRAS/BRAF and PI3K/AKT pathways in colorectal cancer: implications for targeted therapy. *Discov. Med.,* 14:207-214, 2012.

Boisvert et al., The GAR motif of 53BP1 is arginine methylated by PRMT1 and is necessary for 53BP1 DNA binding activity. *Cell Cycle,* 4:1834-1841, 2005.

Bukowski et al., *Clinical Cancer Res.,* 4(10):2337-2347, 1998.

Christodoulides et al., *Microbiology,* 144(Pt 11):3027-3037, 1998.

Chung et al., Spatial control of EGF receptor activation by reversible dimerization on living cells. *Nature,* 464:783-787, 2010.

Custodio and Feliu, Prognostic and predictive biomarkers for epidermal growth factor receptor-targeted therapy in colorectal cancer: beyond KRAS mutations. *Crit. Rev. Oncol. Hematol.,* 85:45-81, 2013

Davidson et al., *J. Immunother.,* 21(5):389-398, 1998.

De Roock et al., KRAS wild-type state predicts survival and is associated to early radiological response in metastatic colorectal cancer treated with cetuximab. *Ann. Oncol.,* 19:508-515, 2008.

De Roock et al., Association of KRAS p.G13D mutation with outcome in patients with chemotherapy-refractory metastatic colorectal cancer treated with cetuximab. *JAMA,* 304:1812-1820, 2010.

Fabian and Berkovcova, Molecular predictive markers of EGFR-targeted therapy in metastatic colorectal cancer. *Cesk. Patol.,* 47:154-158, 2011.

Ferguson et al., EGF activates its receptor by removing interactions that autoinhibit ectodomain dimerization. *Mol. Cell,* 11:507-517, 2003.

Gill et al., Monoclonal anti-epidermal growth factor receptor antibodies which are inhibitors of epidermal growth factor binding and antagonists of epidermal growth factor binding and antagonists of epidermal growth factor-stimulated tyrosine protein kinase activity. *J. Biol. Chem.,* 259:7755-7760, 1984.

Goding, "Monoclonal antibodies: Principles and practice." Second Edition, Academic Press, London, England, 1986.

Hanibuchi et al., *Int. J. Cancer,* 78(4):480-485, 1998.

Hellstrand et al., *Acta Oncologica,* 37(4):347-353, 1998.

Hollander, *Front. Immun.,* 3:3, 2012.

Hsieh et al., Epidermal growth factor receptor R521K polymorphism shows favorable outcomes in KRAS wild-type colorectal cancer patients treated with cetuximab-based chemotherapy. *Cancer Sci.,* 103:791-796, 2012.

Hsu et al., Crosstalk between Arg 1175 methylation and Tyr 1173 phosphorylation negatively modulates EGFR-mediated ERK activation. *Nat. Cell Biol.,* 13:174-181, 2011.

Hui and Hashimoto, *Infection Immun.,* 66(11):5329-5336, 1998.

Köhler and Milstein, Derivation of specific antibody-producing tissue culture and tumor lines by cell fusion. *Eur. J. Immunol.,* 6:511-519, 1976.

Laurent-Puig et al. Analysis of PTEN, BRAF, and EGFR status in determining benefit from cetuximab therapy in wild-type KRAS metastatic colon cancer. *J. Clin. Oncol.,* 27:5924-5930, 2009.

Le Romancer et al., Regulation of estrogen rapid signaling through arginine methylation by PRMT1. *Mol. Cell,* 31:212-221, 2008.

Li et al., Structural basis for inhibition of the epidermal growth factor receptor by cetuximab. *Cancer Cell,* 7:301-311, 2005.

Lievre et al., KRAS mutations as an independent prognostic factor in patients with advanced colorectal cancer treated with cetuximab. *J. Clin. Oncol.,* 26:374-379, 2008.

Mao et al., KRAS p.G13D mutation and codon 12 mutations are not created equal in predicting clinical outcomes of cetuximab in metastatic colorectal cancer: A systematic review and meta-analysis. *Cancer,* 119:714-721, 2013.

Mathioudaki et al., The PRMT1 gene expression pattern in colon cancer. *Br. J. Cancer,* 99:2094-2099, 2008.

Messner et al., KRAS p.G13D mutations are associated with sensitivity to anti-EGFR antibody treatment in colorectal cancer cell lines. *J. Cancer Res. Clin. Oncol.,* 139:201-209, 2013.

Morton and Hammond, ASCO Provisional Clinical Opinion: KRAS, Cetuximab, and Panitumumab-Clinical Implications in Colorectal Cancer. *J. Oncol. Pract.,* 5:71-72, 2009.

Ogiso et al., Crystal structure of the complex of human epidermal growth factor and receptor extracellular domains. *Cell,* 110:775-787, 2002.

Papadokostopoulou et al., Colon cancer and protein arginine methyltransferase 1 gene expression. *Anticancer Res.,* 29:1361-1366, 2009.

Qin et al., *Proc. Natl. Acad. Sci. USA,* 95(24):14411-14416, 1998.

Remington's Pharmaceutical Sciences, 18th Ed., A. R. Gennaro et al. (eds.), Mack Publishing Co., Easton, Pa., 1990.

Silvestris et al., KRAS mutations and sensitivity to anti-EGFR monoclonal antibodies in metastatic colorectal carcinoma: an open issue. *Expert Opin. Biol. Ther.,* 9:565-577, 2009.

Tejpar et al., Association of KRAS G13D tumor mutations with outcome in patients with metastatic colorectal cancer treated with first-line chemotherapy with or without cetuximab. *J. Clin. Oncol.,* 30:3570-3577, 2012.

van Houdt et al., Oncogenic KRAS desensitizes colorectal tumor cells to epidermal growth factor receptor inhibition and activation. *Neoplasia,* 12:443-452, 2010.

Yang and Bedford, Protein arginine methyltransferases and cancer. *Nat. Rev. Cancer,* 13:37-50, 2013.

Yu et al., The MRE11 GAR motif regulates DNA double-strand break processing and ATR activation. *Cell Res.,* 22:305-320, 2012.

The invention claimed is:

1. A method of treating a patient having cancer comprising administering an effective amount of cetuximab and a PRMT inhibitor to a patient in need thereof, said patient having been determined to have a cancer cell comprising (i) methylated Arg at position 198, (ii) methylated Arg at position 200, and/or (iii) an Arg residue at position 497 of a EGFR protein expressed in the cancer cell.

2. The method of claim 1, wherein the presence of (i) methylated Arg at position 198 and/or (ii) methylated Arg at position 200 of EGFR protein is detected by mass spectrometry, ELISA, flow cytometry, immunohistochemistry, western blot, radioimmunoassay, or immunoprecipitation.

3. The method of claim 1, further comprising determining the methylation status of an arginine present at position 497 of EGFR.

4. The method of claim 3, wherein the methylation status is determined by mass spectrometry, immunohistochemistry, western blotting, or ELISA.

5. The method of claim 1, wherein the amino acid present at position 497 of the EGFR protein is determined by mass spectrometry or sequencing a nucleic acid comprising at least a portion of the protein coding sequence of the EGFR protein.

6. The method of claim 1, wherein the patient is a human patient.

7. The method of claim 1, wherein the PRMT inhibitor is sinefungin, S-adenosylhomocysteine, AMI-1, AMI-408, MDL 28,842, methylthioadenosine, C21, Eosin Y, disodium trihydrate, Cpd4, or adenosine dialdehyde.

8. The method of claim 1, wherein the cancer is a colorectal, breast, prostate, lung, or pancreatic cancer.

9. The method of claim 1, wherein the cancer is metastatic, recurrent, or multi-drug resistant.

10. The method of claim 1, wherein the patient is treated at least a second time.

11. The method of claim 1, wherein the patient is treated over a period of 1 week to 6 months.

12. The method of claim 1, further comprising administering a third anticancer therapy.

13. The method of claim 12, wherein the third anticancer therapy is a surgical therapy, chemotherapy, radiation therapy, cryotherapy, hormonal therapy, toxin therapy, immunotherapy, or cytokine therapy.

14. The method of claim 1, wherein the cancer cell is from a biopsy sample.

15. The method of claim 1, wherein the cancer cell is a circulating tumor cell.

* * * * *